(12) United States Patent    (10) Patent No.: US 9,027,552 B2
Angelico et al.    (45) Date of Patent: May 12, 2015

(54) VENTILATOR-INITIATED PROMPT OR SETTING REGARDING DETECTION OF ASYNCHRONY DURING VENTILATION

(75) Inventors: Phyllis Angelico, Carlsbad, CA (US); Peter R. Doyle, Vista, CA (US); Gardner Kimm, Carlsbad, CA (US); Gary Milne, Louisville, CO (US)

(73) Assignee: Covidien LP, Manfield, MA (US)

( * ) Notice: Subject to any disclaimer, the term of this patent is extended or adjusted under 35 U.S.C. 154(b) by 454 days.

(21) Appl. No.: 13/562,991

(22) Filed: Jul. 31, 2012

(65) Prior Publication Data

US 2014/0034054 A1    Feb. 6, 2014

(51) Int. Cl.
*A61M 11/00*    (2006.01)
*A61M 15/00*    (2006.01)
*A61M 16/00*    (2006.01)

(52) U.S. Cl.
CPC ... *A61M 15/0051* (2013.01); *A61M 2016/0027* (2013.01); *A61M 2016/0036* (2013.01); *A61M 2205/13* (2013.01); *A61M 2205/14* (2013.01); *A61M 2205/18* (2013.01); *A61M 2205/505* (2013.01); *A61M 2230/46* (2013.01); *A61M 2230/60* (2013.01)

(58) Field of Classification Search
USPC .............. 128/204.18–204.26; 600/529, 538
See application file for complete search history.

(56) References Cited

U.S. PATENT DOCUMENTS

| | | | |
|---|---|---|---|
| 1,202,125 | A | 10/1916 | Tullar |
| 1,202,126 | A | 10/1916 | Tullar |
| 1,241,056 | A | 9/1917 | Tullar |
| 2,914,067 | A | 11/1959 | Meidenbauer |
| 3,339,545 | A | 9/1967 | Barnett |
| 3,584,618 | A | 6/1971 | Reinhard et al. |

(Continued)

FOREIGN PATENT DOCUMENTS

| | | |
|---|---|---|
| WO | WO 95/16484 | 6/1995 |
| WO | WO 9829790 | 7/1998 |

(Continued)

OTHER PUBLICATIONS

U.S. Appl. No. 12/775,550, Office Action mailed Sep. 26, 2012, 32 pgs.

(Continued)

*Primary Examiner* — Steven Douglas

(57) ABSTRACT

This disclosure describes systems and methods for monitoring and evaluating ventilatory parameters, analyzing those parameters and providing useful notifications and recommendations to clinicians. That is, modern ventilators monitor, evaluate, and graphically represent multiple ventilatory parameters. However, many clinicians may not easily recognize data patterns and correlations indicative of certain patient conditions, changes in patient condition, and/or effectiveness of ventilatory treatment. Further, clinicians may not readily determine appropriate ventilatory adjustments that may address certain patient conditions and/or the effectiveness of ventilatory treatment. Specifically, clinicians may not readily detect or recognize the presence of asynchrony during ventilation. According to embodiments, a ventilator may be configured to monitor and evaluate diverse ventilatory parameters to detect asynchrony and may issue notifications and recommendations suitable for a patient to the clinician when asynchrony is implicated. The suitable notifications and recommendations may further be provided in a hierarchical format.

20 Claims, 7 Drawing Sheets

(56) References Cited

U.S. PATENT DOCUMENTS

| | | |
|---|---|---|
| 3,628,531 A | 12/1971 | Harris |
| 3,643,652 A | 2/1972 | Beltran |
| 3,722,510 A | 3/1973 | Parker |
| 3,739,776 A | 6/1973 | Bird et al. |
| 3,759,249 A | 9/1973 | Fletcher et al. |
| 3,911,899 A | 10/1975 | Hattes |
| 3,952,739 A | 4/1976 | Cibulka |
| 3,957,044 A | 5/1976 | Fletcher et al. |
| 3,968,794 A | 7/1976 | O'Neill |
| 3,968,795 A | 7/1976 | O'Neill et al. |
| 3,985,131 A | 10/1976 | Buck et al. |
| 3,991,304 A | 11/1976 | Hillsman |
| 4,258,718 A | 3/1981 | Goldman |
| 4,281,651 A | 8/1981 | Cox |
| 4,284,075 A | 8/1981 | Krasberg |
| 4,294,242 A | 10/1981 | Cowans |
| 4,299,236 A | 11/1981 | Poirier |
| 4,316,182 A | 2/1982 | Hodgson |
| 4,366,821 A | 1/1983 | Wittmaier et al. |
| 4,433,693 A | 2/1984 | Hochstein |
| 4,440,166 A | 4/1984 | Winkler et al. |
| 4,442,835 A | 4/1984 | Carnegie |
| 4,459,982 A | 7/1984 | Fry |
| 4,498,471 A | 2/1985 | Kranz et al. |
| 4,503,850 A | 3/1985 | Pasternak |
| 4,506,667 A | 3/1985 | Ansite |
| 4,522,639 A | 6/1985 | Ansite et al. |
| 4,546,770 A | 10/1985 | Schlessinger et al. |
| 4,550,726 A | 11/1985 | McEwen |
| 4,606,340 A | 8/1986 | Ansite |
| 4,630,605 A | 12/1986 | Pasternack |
| 4,648,407 A | 3/1987 | Sackner |
| 4,653,493 A | 3/1987 | Hoppough |
| 4,752,089 A | 6/1988 | Carter |
| 4,870,960 A | 10/1989 | Hradek |
| 4,917,080 A | 4/1990 | Bayerlein |
| 4,921,642 A | 5/1990 | LaTorraca |
| 4,954,799 A | 9/1990 | Kumar |
| 4,984,158 A | 1/1991 | Hillsman |
| 4,990,894 A | 2/1991 | Loescher et al. |
| 5,022,393 A | 6/1991 | McGrady et al. |
| 5,048,515 A | 9/1991 | Sanso |
| 5,057,822 A | 10/1991 | Hoffman |
| 5,072,737 A | 12/1991 | Goulding |
| 5,107,831 A | 4/1992 | Halpern et al. |
| 5,150,291 A | 9/1992 | Cummings et al. |
| 5,156,145 A | 10/1992 | Flood et al. |
| 5,161,525 A | 11/1992 | Kimm et al. |
| 5,165,397 A | 11/1992 | Arp |
| 5,237,987 A | 8/1993 | Anderson et al. |
| 5,271,389 A | 12/1993 | Isaza et al. |
| 5,273,031 A | 12/1993 | Olsson et al. |
| 5,279,549 A | 1/1994 | Ranford |
| 5,299,568 A | 4/1994 | Forare et al. |
| 5,301,921 A | 4/1994 | Kumar |
| 5,319,540 A | 6/1994 | Isaza et al. |
| 5,322,059 A | 6/1994 | Walther |
| 5,325,861 A | 7/1994 | Goulding |
| 5,333,606 A | 8/1994 | Schneider et al. |
| 5,335,654 A | 8/1994 | Rapoport |
| 5,339,807 A | 8/1994 | Carter |
| 5,343,857 A | 9/1994 | Schneider et al. |
| 5,351,522 A | 10/1994 | Lura |
| 5,357,946 A | 10/1994 | Kee et al. |
| 5,368,019 A | 11/1994 | LaTorraca |
| 5,383,449 A | 1/1995 | Forare et al. |
| 5,385,142 A | 1/1995 | Brady et al. |
| 5,390,666 A | 2/1995 | Kimm et al. |
| 5,398,682 A | 3/1995 | Lynn |
| 5,401,135 A | 3/1995 | Stoen et al. |
| 5,402,796 A | 4/1995 | Packer et al. |
| 5,407,174 A | 4/1995 | Kumar |
| 5,413,110 A | 5/1995 | Cummings et al. |
| 5,429,123 A | 7/1995 | Shaffer et al. |
| 5,438,980 A | 8/1995 | Phillips |
| 5,443,075 A | 8/1995 | Holscher |
| 5,477,860 A | 12/1995 | Essen Moller |
| 5,485,833 A | 1/1996 | Dietz |
| 5,490,502 A | 2/1996 | Rapoport et al. |
| 5,513,631 A | 5/1996 | McWilliams |
| 5,517,983 A | 5/1996 | Deighan et al. |
| 5,520,071 A | 5/1996 | Jones |
| 5,520,192 A | 5/1996 | Kitney et al. |
| 5,524,615 A | 6/1996 | Power |
| 5,524,616 A | 6/1996 | Smith et al. |
| 5,531,221 A | 7/1996 | Power |
| 5,540,218 A | 7/1996 | Jones et al. |
| 5,542,415 A | 8/1996 | Brady |
| 5,544,674 A | 8/1996 | Kelly |
| 5,549,106 A | 8/1996 | Gruenke et al. |
| 5,582,182 A | 12/1996 | Hillsman |
| 5,596,984 A | 1/1997 | O'Mahony et al. |
| 5,598,838 A | 2/1997 | Servidio et al. |
| 5,605,151 A | 2/1997 | Lynn |
| 5,608,647 A | 3/1997 | Rubsamen et al. |
| 5,630,411 A | 5/1997 | Holscher |
| 5,632,270 A | 5/1997 | O'Mahoney et al. |
| 5,645,048 A | 7/1997 | Brodsky et al. |
| 5,660,171 A | 8/1997 | Kimm et al. |
| 5,662,099 A | 9/1997 | Tobia et al. |
| 5,664,560 A | 9/1997 | Merrick et al. |
| 5,664,562 A | 9/1997 | Bourdon |
| 5,669,379 A | 9/1997 | Somerson et al. |
| 5,671,767 A | 9/1997 | Kelly |
| 5,672,041 A | 9/1997 | Ringdahl et al. |
| 5,673,689 A | 10/1997 | Power |
| 5,678,539 A | 10/1997 | Schubert et al. |
| 5,685,318 A | 11/1997 | Elghazzawi |
| 5,692,497 A | 12/1997 | Schnitzer et al. |
| 5,715,415 A | 2/1998 | Dazey et al. |
| 5,715,812 A | 2/1998 | Deighan et al. |
| 5,730,121 A | 3/1998 | Hawkins, Jr. et al. |
| 5,752,509 A | 5/1998 | Lachmann et al. |
| 5,762,480 A | 6/1998 | Adahan |
| 5,771,884 A | 6/1998 | Yarnall et al. |
| 5,791,339 A | 8/1998 | Winter |
| 5,794,986 A | 8/1998 | Gansel et al. |
| 5,803,066 A | 9/1998 | Rapoport et al. |
| 5,810,741 A | 9/1998 | Essen Moller |
| 5,813,399 A | 9/1998 | Isaza et al. |
| 5,826,575 A | 10/1998 | Lall |
| 5,829,441 A | 11/1998 | Kidd et al. |
| 5,832,916 A | 11/1998 | Lundberg |
| 5,832,919 A | 11/1998 | Kano et al. |
| 5,860,418 A | 1/1999 | Lundberg |
| 5,864,938 A | 2/1999 | Gansel et al. |
| 5,865,168 A | 2/1999 | Isaza |
| 5,876,353 A | 3/1999 | Riff |
| 5,881,717 A | 3/1999 | Isaza |
| 5,881,723 A | 3/1999 | Wallace et al. |
| 5,884,623 A | 3/1999 | Winter |
| 5,891,023 A | 4/1999 | Lynn |
| 5,909,731 A | 6/1999 | O'Mahony et al. |
| 5,915,379 A | 6/1999 | Wallace et al. |
| 5,915,380 A | 6/1999 | Wallace et al. |
| 5,915,382 A | 6/1999 | Power |
| 5,918,597 A | 7/1999 | Jones et al. |
| 5,921,238 A | 7/1999 | Bourdon |
| 5,921,920 A | 7/1999 | Marshall et al. |
| 5,927,274 A | 7/1999 | Servidio et al. |
| 5,931,160 A | 8/1999 | Gilmore et al. |
| 5,934,274 A | 8/1999 | Merrick et al. |
| 5,957,129 A | 9/1999 | Tham et al. |
| 5,964,218 A | 10/1999 | Smith et al. |
| 5,964,220 A | 10/1999 | Boussignac et al. |
| 5,996,580 A | 12/1999 | Swann |
| 6,024,089 A | 2/2000 | Wallace et al. |
| 6,029,660 A | 2/2000 | Calluaud et al. |
| 6,041,780 A | 3/2000 | Richard et al. |
| 6,047,860 A | 4/2000 | Sanders |
| 6,067,022 A | 5/2000 | Laswick et al. |
| 6,076,523 A | 6/2000 | Jones et al. |
| 6,109,259 A | 8/2000 | Fitzgerald |
| 6,112,744 A | 9/2000 | Hognelid |

(56) References Cited

U.S. PATENT DOCUMENTS

| | | | |
|---|---|---|---|
| 6,116,240 | A | 9/2000 | Merrick et al. |
| 6,116,464 | A | 9/2000 | Sanders |
| 6,123,073 | A | 9/2000 | Schlawin et al. |
| 6,135,106 | A | 10/2000 | Dirks et al. |
| 6,139,506 | A | 10/2000 | Heinonen |
| 6,142,150 | A | 11/2000 | O'Mahony et al. |
| 6,148,814 | A | 11/2000 | Clemmer et al. |
| 6,158,430 | A | 12/2000 | Pfeiffer et al. |
| 6,158,432 | A | 12/2000 | Biondi et al. |
| 6,161,539 | A | 12/2000 | Winter |
| 6,168,568 | B1 | 1/2001 | Gavriely |
| 6,192,876 | B1 | 2/2001 | Denyer et al. |
| 6,206,001 | B1 | 3/2001 | Garber et al. |
| 6,206,837 | B1 | 3/2001 | Brugnoli |
| 6,213,120 | B1 | 4/2001 | Block et al. |
| 6,216,690 | B1 | 4/2001 | Keitel et al. |
| 6,220,245 | B1 | 4/2001 | Takabayashi et al. |
| 6,223,064 | B1 | 4/2001 | Lynn et al. |
| 6,227,197 | B1 | 5/2001 | Fitzgerald |
| 6,240,920 | B1 | 6/2001 | Ström |
| 6,258,039 | B1 | 7/2001 | Okamoto et al. |
| 6,269,812 | B1 | 8/2001 | Wallace et al. |
| 6,273,088 | B1 | 8/2001 | Hillsman |
| 6,273,444 | B1 | 8/2001 | Power |
| 6,283,119 | B1 | 9/2001 | Bourdon |
| 6,305,372 | B1 | 10/2001 | Servidio |
| 6,305,373 | B1 | 10/2001 | Wallace et al. |
| 6,321,748 | B1 | 11/2001 | O'Mahoney |
| 6,322,502 | B1 | 11/2001 | Schoenberg et al. |
| 6,325,785 | B1 | 12/2001 | Babkes et al. |
| 6,341,604 | B1 | 1/2002 | Kellon |
| 6,342,039 | B1 | 1/2002 | Lynn et al. |
| 6,357,438 | B1 | 3/2002 | Hansen |
| 6,360,745 | B1 | 3/2002 | Wallace et al. |
| 6,369,838 | B1 | 4/2002 | Wallace et al. |
| 6,397,838 | B1 | 6/2002 | Zimlich, Jr. et al. |
| 6,398,728 | B1 | 6/2002 | Bardy |
| 6,412,483 | B1 | 7/2002 | Jones et al. |
| 6,439,229 | B1 | 8/2002 | Du et al. |
| 6,446,630 | B1 | 9/2002 | Todd, Jr. |
| 6,457,472 | B1 | 10/2002 | Schwartz et al. |
| 6,463,930 | B2 | 10/2002 | Biondi et al. |
| 6,467,477 | B1 | 10/2002 | Frank et al. |
| 6,467,478 | B1 | 10/2002 | Merrick et al. |
| 6,467,481 | B1 | 10/2002 | Eswarappa |
| 6,536,433 | B1 | 3/2003 | Cewers |
| 6,546,930 | B1 | 4/2003 | Emerson et al. |
| 6,551,243 | B2 | 4/2003 | Bocionek et al. |
| 6,553,991 | B1 | 4/2003 | Isaza |
| 6,557,553 | B1 | 5/2003 | Borrello |
| 6,564,797 | B1 | 5/2003 | Mechlenburg et al. |
| 6,569,095 | B2 | 5/2003 | Eggers |
| 6,571,795 | B2 | 6/2003 | Bourdon |
| 6,577,884 | B1 | 6/2003 | Boas |
| 6,578,575 | B1 | 6/2003 | Jonson |
| 6,584,973 | B1 | 7/2003 | Biondi et al. |
| 6,607,481 | B1 | 8/2003 | Clawson |
| 6,609,016 | B1 | 8/2003 | Lynn |
| 6,622,726 | B1 | 9/2003 | Du |
| 6,644,310 | B1 | 11/2003 | Delache et al. |
| 6,644,312 | B2 | 11/2003 | Berthon-Jones et al. |
| 6,655,383 | B1 | 12/2003 | Lundberg |
| 6,668,824 | B1 | 12/2003 | Isaza et al. |
| 6,668,829 | B2 | 12/2003 | Biondi et al. |
| 6,675,801 | B2 | 1/2004 | Wallace et al. |
| 6,679,258 | B1 | 1/2004 | Ström |
| 6,709,405 | B2 | 3/2004 | Jonson |
| 6,717,589 | B2 | 4/2004 | Grillo et al. |
| 6,718,974 | B1 | 4/2004 | Moberg |
| 6,718,975 | B2 | 4/2004 | Blomberg |
| 6,725,447 | B1 | 4/2004 | Gilman et al. |
| 6,739,337 | B2 | 5/2004 | Isaza |
| 6,743,172 | B1 | 6/2004 | Blike |
| 6,745,764 | B2 | 6/2004 | Hickle |
| 6,748,252 | B2 | 6/2004 | Lynn et al. |
| 6,752,150 | B1 | 6/2004 | Remmers et al. |
| 6,760,608 | B2 | 7/2004 | Lynn |
| 6,761,167 | B1 | 7/2004 | Nadjafizadeh et al. |
| 6,761,168 | B1 | 7/2004 | Nadjafizadeh et al. |
| 6,796,305 | B1 | 9/2004 | Banner et al. |
| 6,804,656 | B1 | 10/2004 | Rosenfeld et al. |
| 6,807,965 | B1 | 10/2004 | Hickle |
| 6,814,074 | B1 | 11/2004 | Nadjafizadeh et al. |
| 6,832,609 | B2 | 12/2004 | Wright et al. |
| 6,837,241 | B2 | 1/2005 | Samzelius |
| 6,845,773 | B2 | 1/2005 | Berthon-Jones et al. |
| 6,860,266 | B2 | 3/2005 | Blike |
| 6,866,040 | B1 | 3/2005 | Bourdon |
| 6,899,101 | B2 | 5/2005 | Haston et al. |
| 6,949,073 | B2 | 9/2005 | Sarel |
| 6,949,133 | B2 | 9/2005 | McCombs et al. |
| 6,960,854 | B2 | 11/2005 | Nadjafizadeh et al. |
| 6,986,347 | B2 | 1/2006 | Hickle |
| 6,990,977 | B1 | 1/2006 | Calluaud et al. |
| 7,017,574 | B2 | 3/2006 | Biondi et al. |
| 7,018,341 | B2 | 3/2006 | Wright et al. |
| 7,036,504 | B2 | 5/2006 | Wallace et al. |
| 7,040,320 | B2 | 5/2006 | Fjeld et al. |
| 7,046,254 | B2 | 5/2006 | Brown et al. |
| 7,051,735 | B2 | 5/2006 | Mechlenburg et al. |
| 7,066,173 | B2 | 6/2006 | Banner et al. |
| 7,073,501 | B2 | 7/2006 | Remmers et al. |
| 7,077,131 | B2 | 7/2006 | Hansen |
| 7,081,091 | B2 | 7/2006 | Merrett et al. |
| 7,081,095 | B2 | 7/2006 | Lynn et al. |
| RE39,225 | E | 8/2006 | Isaza et al. |
| 7,086,399 | B2 | 8/2006 | Makinson et al. |
| 7,089,930 | B2 | 8/2006 | Adams et al. |
| 7,089,937 | B2 | 8/2006 | Berthon-Jones et al. |
| 7,117,438 | B2 | 10/2006 | Wallace et al. |
| 7,201,734 | B2 | 4/2007 | Hickle |
| 7,207,945 | B2 | 4/2007 | Bardy |
| 7,210,478 | B2 | 5/2007 | Banner et al. |
| 7,222,623 | B2 | 5/2007 | DeVries et al. |
| 7,247,154 | B2 | 7/2007 | Hickle |
| 7,256,708 | B2 | 8/2007 | Rosenfeld et al. |
| 7,258,670 | B2 | 8/2007 | Bardy |
| 7,270,126 | B2 | 9/2007 | Wallace et al. |
| 7,307,543 | B2 | 12/2007 | Rosenfeld et al. |
| 7,308,894 | B2 | 12/2007 | Hickle |
| 7,315,825 | B2 | 1/2008 | Rosenfeld et al. |
| 7,321,862 | B2 | 1/2008 | Rosenfeld et al. |
| 7,322,937 | B2 | 1/2008 | Blomberg et al. |
| 7,334,578 | B2 | 2/2008 | Biondi et al. |
| 7,346,846 | B2 | 3/2008 | Rossi, Jr. et al. |
| 7,347,204 | B1 | 3/2008 | Lindsey et al. |
| 7,369,757 | B2 | 5/2008 | Farbarik |
| 7,370,650 | B2 | 5/2008 | Nadjafizadeh et al. |
| 7,374,535 | B2 | 5/2008 | Schoenberg et al. |
| 7,395,216 | B2 | 7/2008 | Rosenfeld et al. |
| 7,398,115 | B2 | 7/2008 | Lynn |
| 7,428,902 | B2 | 9/2008 | Du et al. |
| 7,433,827 | B2 | 10/2008 | Rosenfeld et al. |
| 7,454,359 | B2 | 11/2008 | Rosenfeld et al. |
| 7,454,360 | B2 | 11/2008 | Rosenfeld et al. |
| 7,460,959 | B2 | 12/2008 | Jafari |
| 7,467,094 | B2 | 12/2008 | Rosenfeld et al. |
| 7,475,019 | B2 | 1/2009 | Rosenfeld et al. |
| 7,487,773 | B2 | 2/2009 | Li |
| 7,495,546 | B2 | 2/2009 | Lintell et al. |
| 7,520,279 | B2 | 4/2009 | Berthon-Jones |
| 7,556,038 | B2 | 7/2009 | Kirby et al. |
| 7,561,912 | B2 | 7/2009 | Schatz et al. |
| 7,562,657 | B2 | 7/2009 | Blanch et al. |
| 7,565,905 | B2 | 7/2009 | Hickle |
| 7,591,830 | B2 | 9/2009 | Rutter |
| 7,650,291 | B2 | 1/2010 | Rosenfeld et al. |
| 7,654,802 | B2 | 2/2010 | Crawford, Jr. et al. |
| 7,681,571 | B2 | 3/2010 | Makinson et al. |
| 7,694,677 | B2 | 4/2010 | Tang |
| 7,698,156 | B2 | 4/2010 | Martucci et al. |
| 7,708,015 | B2 | 5/2010 | Seeger et al. |
| 7,717,112 | B2 | 5/2010 | Sun et al. |
| 7,717,113 | B2 | 5/2010 | Andrieux |

(56) References Cited

U.S. PATENT DOCUMENTS

| | | |
|---|---|---|
| D618,356 S | 6/2010 | Ross |
| 7,778,851 B2 | 8/2010 | Schoenberg et al. |
| 7,779,834 B2 | 8/2010 | Calluaud et al. |
| 7,784,461 B2 | 8/2010 | Figueiredo et al. |
| 7,802,571 B2 | 9/2010 | Tehrani |
| 7,819,815 B2 | 10/2010 | Younes |
| 7,823,588 B2 | 11/2010 | Hansen |
| 7,831,450 B2 | 11/2010 | Schoenberg et al. |
| 7,855,716 B2 | 12/2010 | McCreary et al. |
| D632,796 S | 2/2011 | Ross et al. |
| D632,797 S | 2/2011 | Ross et al. |
| 7,886,231 B2 | 2/2011 | Hopermann |
| 7,886,739 B2 | 2/2011 | Soliman |
| 7,891,354 B2 | 2/2011 | Farbarik |
| 7,893,560 B2 | 2/2011 | Carter |
| D638,852 S | 5/2011 | Skidmore et al. |
| 7,984,714 B2 | 7/2011 | Hausmann et al. |
| D643,535 S | 8/2011 | Ross et al. |
| 7,992,557 B2 | 8/2011 | Nadjafizadeh et al. |
| 8,001,967 B2 | 8/2011 | Wallace et al. |
| 8,002,711 B2 | 8/2011 | Wood et al. |
| D645,158 S | 9/2011 | Sanchez et al. |
| 8,021,310 B2 | 9/2011 | Sanborn et al. |
| D649,157 S | 11/2011 | Skidmore et al. |
| D652,521 S | 1/2012 | Ross et al. |
| D652,936 S | 1/2012 | Ross et al. |
| D653,749 S | 2/2012 | Winter et al. |
| 8,113,062 B2 | 2/2012 | Graboi et al. |
| D655,405 S | 3/2012 | Winter et al. |
| D655,809 S | 3/2012 | Winter et al. |
| D656,237 S | 3/2012 | Sanchez et al. |
| 8,181,648 B2 | 5/2012 | Perine et al. |
| 8,210,173 B2 | 7/2012 | Vandine |
| 8,210,174 B2 | 7/2012 | Farbarik |
| 8,224,636 B2 | 7/2012 | Kundert |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 8,757,153 B2 * | 6/2014 | Milne et al. ............... 128/204.23 |
| 2001/0004893 A1 | 6/2001 | Biondi et al. |
| 2001/0027791 A1 | 10/2001 | Wallace et al. |
| 2001/0035186 A1 | 11/2001 | Hill |
| 2002/0023644 A1 | 2/2002 | Berthon-Jones |
| 2002/0026941 A1 | 3/2002 | Biondi et al. |
| 2002/0117173 A1 | 8/2002 | Lynn et al. |
| 2002/0153006 A1 | 10/2002 | Zimlich et al. |
| 2002/0153009 A1 | 10/2002 | Chornyj et al. |
| 2002/0177758 A1 | 11/2002 | Schoenberg et al. |
| 2003/0036687 A1 | 2/2003 | Schoenberg et al. |
| 2003/0106553 A1 | 6/2003 | Vanderveen |
| 2003/0121519 A1 | 7/2003 | Estes et al. |
| 2003/0140928 A1 | 7/2003 | Bui et al. |
| 2003/0141981 A1 | 7/2003 | Bui et al. |
| 2003/0153818 A1 | 8/2003 | Bocionek et al. |
| 2003/0158466 A1 | 8/2003 | Lynn et al. |
| 2003/0176804 A1 | 9/2003 | Melker |
| 2003/0188748 A1 | 10/2003 | Sinderby et al. |
| 2003/0230308 A1 | 12/2003 | Linden |
| 2004/0003814 A1 | 1/2004 | Banner et al. |
| 2004/0041828 A1 | 3/2004 | Zellhoefer |
| 2004/0050387 A1 | 3/2004 | Younes |
| 2004/0121767 A1 | 6/2004 | Simpson et al. |
| 2004/0149282 A1 | 8/2004 | Hickle |
| 2004/0167804 A1 | 8/2004 | Simpson et al. |
| 2004/0172302 A1 | 9/2004 | Martucci et al. |
| 2004/0236240 A1 | 11/2004 | Kraus et al. |
| 2004/0244807 A1 | 12/2004 | Sun et al. |
| 2005/0016534 A1 | 1/2005 | Ost |
| 2005/0039127 A1 | 2/2005 | Davis |
| 2005/0039748 A1 | 2/2005 | Andrieux |
| 2005/0043969 A1 | 2/2005 | Sarel |
| 2005/0055242 A1 | 3/2005 | Bello et al. |
| 2005/0065817 A1 | 3/2005 | Mihai et al. |
| 2005/0112325 A1 | 5/2005 | Hickle |
| 2005/0121035 A1 | 6/2005 | Martin |
| 2005/0124866 A1 | 6/2005 | Elaz et al. |
| 2005/0133024 A1 | 6/2005 | Coifman |
| 2005/0139212 A1 | 6/2005 | Bourdon |
| 2005/0188991 A1 | 9/2005 | Sun et al. |
| 2005/0204310 A1 | 9/2005 | De Zwart et al. |
| 2006/0009708 A1 | 1/2006 | Rapoport et al. |
| 2006/0060198 A1 | 3/2006 | Aylsworth et al. |
| 2006/0085229 A9 | 4/2006 | Rosenfeld et al. |
| 2006/0089543 A1 | 4/2006 | Kim et al. |
| 2006/0112959 A1 | 6/2006 | Mechlenburg et al. |
| 2006/0122869 A9 | 6/2006 | Rosenfeld et al. |
| 2006/0135878 A1 | 6/2006 | Wright et al. |
| 2006/0142815 A1 | 6/2006 | Tehrani et al. |
| 2006/0144144 A1 | 7/2006 | Seto |
| 2006/0144397 A1 | 7/2006 | Wallace et al. |
| 2006/0155206 A1 | 7/2006 | Lynn |
| 2006/0155207 A1 | 7/2006 | Lynn et al. |
| 2006/0161071 A1 | 7/2006 | Lynn et al. |
| 2006/0161459 A9 | 7/2006 | Rosenfeld et al. |
| 2006/0178591 A1 | 8/2006 | Hempfling |
| 2006/0189880 A1 | 8/2006 | Lynn et al. |
| 2006/0195041 A1 | 8/2006 | Lynn et al. |
| 2006/0201505 A1 | 9/2006 | Remmers et al. |
| 2006/0201506 A1 | 9/2006 | Makinson et al. |
| 2006/0235324 A1 | 10/2006 | Lynn |
| 2006/0237015 A1 | 10/2006 | Berthon-Jones et al. |
| 2006/0243275 A1 | 11/2006 | Ruckdeschel et al. |
| 2006/0249148 A1 | 11/2006 | Younes |
| 2006/0249149 A1 | 11/2006 | Meier et al. |
| 2006/0249151 A1 | 11/2006 | Gambone |
| 2006/0271409 A1 | 11/2006 | Rosenfeld et al. |
| 2006/0276701 A1 | 12/2006 | Ray |
| 2006/0294464 A1 | 12/2006 | Tokimoto et al. |
| 2007/0000494 A1 | 1/2007 | Banner et al. |
| 2007/0017510 A1 | 1/2007 | Riedo |
| 2007/0017515 A1 | 1/2007 | Wallace et al. |
| 2007/0028921 A1 | 2/2007 | Banner et al. |
| 2007/0050715 A1 | 3/2007 | Behar |
| 2007/0066961 A1 | 3/2007 | Rutter |
| 2007/0077200 A1 | 4/2007 | Baker |
| 2007/0093721 A1 | 4/2007 | Lynn et al. |
| 2007/0129647 A1 | 6/2007 | Lynn |
| 2007/0149860 A1 | 6/2007 | Lynn et al. |
| 2007/0163579 A1 | 7/2007 | Li et al. |
| 2007/0167853 A1 | 7/2007 | Melker et al. |
| 2007/0173702 A1 | 7/2007 | Dlugos et al. |
| 2007/0191688 A1 | 8/2007 | Lynn |
| 2007/0191697 A1 | 8/2007 | Lynn et al. |
| 2007/0199566 A1 | 8/2007 | Be'eri |
| 2007/0203415 A1 | 8/2007 | Bardy |
| 2007/0203422 A1 | 8/2007 | Bardy |
| 2007/0203423 A1 | 8/2007 | Bardy |
| 2007/0203448 A1 | 8/2007 | Melker et al. |
| 2007/0213658 A1 | 9/2007 | Hickle |
| 2007/0227537 A1 | 10/2007 | Bemister et al. |
| 2007/0232867 A1 | 10/2007 | Hansmann |
| 2007/0232951 A1 | 10/2007 | Euliano et al. |
| 2007/0272242 A1 | 11/2007 | Sanborn et al. |
| 2007/0284361 A1 | 12/2007 | Nadjafizadeh et al. |
| 2008/0000479 A1 | 1/2008 | Elaz et al. |
| 2008/0017189 A1 | 1/2008 | Ruckdeschel et al. |
| 2008/0021379 A1 | 1/2008 | Hickle |
| 2008/0029097 A1 | 2/2008 | Schatzl |
| 2008/0035145 A1 | 2/2008 | Adams et al. |
| 2008/0041380 A1 | 2/2008 | Wallace et al. |
| 2008/0053441 A1 | 3/2008 | Gottlib et al. |
| 2008/0066752 A1 | 3/2008 | Baker et al. |
| 2008/0072896 A1 | 3/2008 | Setzer et al. |
| 2008/0072900 A1 | 3/2008 | Kenyon et al. |
| 2008/0072902 A1 | 3/2008 | Setzer et al. |
| 2008/0077033 A1 | 3/2008 | Figueiredo et al. |
| 2008/0078390 A1 | 4/2008 | Milne et al. |
| 2008/0081974 A1 | 4/2008 | Pav |
| 2008/0083644 A1 | 4/2008 | Janbakhsh et al. |
| 2008/0086691 A1 | 4/2008 | Hopermann |
| 2008/0091117 A1 | 4/2008 | Choncholas et al. |

(56) References Cited

U.S. PATENT DOCUMENTS

| | | |
|---|---|---|
| 2008/0092043 A1 | 4/2008 | Trethewey |
| 2008/0092894 A1 | 4/2008 | Nicolazzi et al. |
| 2008/0097234 A1 | 4/2008 | Nicolazzi et al. |
| 2008/0110461 A1 | 5/2008 | Mulqueeny et al. |
| 2008/0110462 A1 | 5/2008 | Chekal et al. |
| 2008/0183095 A1 | 7/2008 | Austin et al. |
| 2008/0200775 A1 | 8/2008 | Lynn |
| 2008/0200819 A1 | 8/2008 | Lynn et al. |
| 2008/0230065 A1 | 9/2008 | Heinonen |
| 2008/0236582 A1 | 10/2008 | Tehrani |
| 2008/0276939 A1 | 11/2008 | Tiedje |
| 2008/0283061 A1 | 11/2008 | Tiedje |
| 2008/0308105 A1 | 12/2008 | Alder et al. |
| 2008/0314385 A1 | 12/2008 | Brunner et al. |
| 2009/0020120 A1 | 1/2009 | Schatzl et al. |
| 2009/0078258 A1 | 3/2009 | Bowman et al. |
| 2009/0107502 A1 | 4/2009 | Younes |
| 2009/0139522 A1 | 6/2009 | Thomson et al. |
| 2009/0143694 A1 | 6/2009 | Krauss et al. |
| 2009/0149723 A1 | 6/2009 | Krauss et al. |
| 2009/0165795 A1 | 7/2009 | Nadjafizadeh et al. |
| 2009/0171176 A1 | 7/2009 | Andersohn |
| 2009/0171226 A1 | 7/2009 | Campbell et al. |
| 2009/0188502 A1 | 7/2009 | Tiedje |
| 2009/0199855 A1 | 8/2009 | Davenport |
| 2009/0205661 A1 | 8/2009 | Stephenson et al. |
| 2009/0205663 A1 | 8/2009 | Vandine et al. |
| 2009/0221926 A1 | 9/2009 | Younes |
| 2009/0241952 A1 | 10/2009 | Nicolazzi et al. |
| 2009/0241953 A1 | 10/2009 | Vandine et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0247891 A1 | 10/2009 | Wood |
| 2009/0259135 A1 | 10/2009 | Stasz |
| 2009/0270752 A1 | 10/2009 | Coifman |
| 2009/0275811 A1 | 11/2009 | Schatz et al. |
| 2009/0293877 A1 | 12/2009 | Blanch et al. |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |
| 2009/0308394 A1 | 12/2009 | Levi |
| 2009/0314290 A1 | 12/2009 | Hickle |
| 2010/0008466 A1 | 1/2010 | Balakin |
| 2010/0011307 A1 | 1/2010 | Desfossez et al. |
| 2010/0024820 A1 | 2/2010 | Bourdon |
| 2010/0030091 A1 | 2/2010 | Fine |
| 2010/0037895 A1 | 2/2010 | Berthon-Jones et al. |
| 2010/0051026 A1 | 3/2010 | Graboi |
| 2010/0051029 A1 | 3/2010 | Jafari et al. |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0078017 A1 | 4/2010 | Andrieux et al. |
| 2010/0078019 A1 | 4/2010 | Rittner et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0083968 A1 | 4/2010 | Wondka et al. |
| 2010/0108064 A1 | 5/2010 | Blackwell et al. |
| 2010/0139660 A1 | 6/2010 | Adahan |
| 2010/0145165 A1 | 6/2010 | Merry |
| 2010/0147303 A1 | 6/2010 | Jafari et al. |
| 2010/0186744 A1 | 7/2010 | Andrieux |
| 2010/0192094 A1 | 7/2010 | Jeha et al. |
| 2010/0198289 A1 | 8/2010 | Kameli et al. |
| 2010/0199015 A1 | 8/2010 | Martucci et al. |
| 2010/0212675 A1 | 8/2010 | Walling et al. |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0222693 A1 | 9/2010 | Eriksen et al. |
| 2010/0236555 A1 | 9/2010 | Jafari et al. |
| 2010/0242961 A1 | 9/2010 | Mougel et al. |
| 2010/0262035 A1 | 10/2010 | Subramanian |
| 2010/0282251 A1 | 11/2010 | Calluaud et al. |
| 2010/0282259 A1 | 11/2010 | Figueiredo et al. |
| 2010/0288283 A1 | 11/2010 | Campbell et al. |
| 2010/0292544 A1 | 11/2010 | Sherman et al. |
| 2010/0300446 A1 | 12/2010 | Nicolazzi et al. |
| 2010/0324438 A1 | 12/2010 | Ni et al. |
| 2010/0331715 A1 | 12/2010 | Addison et al. |
| 2011/0004489 A1 | 1/2011 | Schoenberg et al. |
| 2011/0009763 A1 | 1/2011 | Levitsky et al. |
| 2011/0011400 A1 | 1/2011 | Gentner et al. |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |
| 2011/0041847 A1 | 2/2011 | Cosic |
| 2011/0041849 A1 | 2/2011 | Chen et al. |
| 2011/0041850 A1 | 2/2011 | Vandine et al. |
| 2011/0067698 A1 | 3/2011 | Zheng et al. |
| 2011/0092839 A1 | 4/2011 | Alshaer et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132361 A1 | 6/2011 | Sanchez |
| 2011/0132362 A1 | 6/2011 | Sanchez |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0154241 A1 | 6/2011 | Skidmore et al. |
| 2011/0168177 A1 | 7/2011 | Connor |
| 2011/0175728 A1 | 7/2011 | Baker, Jr. |
| 2011/0196251 A1 | 8/2011 | Jourdain et al. |
| 2011/0197884 A1 | 8/2011 | Duff et al. |
| 2011/0208082 A1 | 8/2011 | Madaus et al. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0230780 A1 | 9/2011 | Sanborn et al. |
| 2011/0249006 A1 | 10/2011 | Wallace et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |
| 2011/0265793 A1 | 11/2011 | Haveri |
| 2011/0271960 A1 | 11/2011 | Milne et al. |
| 2011/0273299 A1 | 11/2011 | Milne et al. |
| 2011/0288431 A1 | 11/2011 | Alshaer et al. |
| 2011/0313263 A1 | 12/2011 | Wood et al. |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0016252 A1 | 1/2012 | Melker et al. |
| 2012/0029317 A1 | 2/2012 | Doyle et al. |
| 2012/0029362 A1 | 2/2012 | Patangay et al. |
| 2012/0030611 A1 | 2/2012 | Skidmore |
| 2012/0037159 A1 | 2/2012 | Mulqueeny et al. |

(56) References Cited

U.S. PATENT DOCUMENTS

| | | |
|---|---|---|
| 2012/0060841 A1 | 3/2012 | Crawford, Jr. et al. |
| 2012/0071729 A1 | 3/2012 | Doyle et al. |
| 2012/0090611 A1 | 4/2012 | Graboi et al. |
| 2012/0096381 A1 | 4/2012 | Milne et al. |
| 2012/0101399 A1 | 4/2012 | Henderson |
| 2012/0123219 A1 | 5/2012 | Georgiev et al. |
| 2012/0133519 A1 | 5/2012 | Milne et al. |
| 2012/0136222 A1 | 5/2012 | Doyle et al. |
| 2012/0136270 A1 | 5/2012 | Leuthardt et al. |
| 2012/0137249 A1 | 5/2012 | Milne et al. |
| 2012/0137250 A1 | 5/2012 | Milne et al. |
| 2012/0167885 A1 | 7/2012 | Masic et al. |
| 2012/0185792 A1 | 7/2012 | Kimm et al. |
| 2012/0197578 A1 | 8/2012 | Vig et al. |
| 2012/0197580 A1 | 8/2012 | Vij et al. |
| 2012/0211008 A1 | 8/2012 | Perine et al. |
| 2012/0216809 A1 | 8/2012 | Milne et al. |
| 2012/0216810 A1 | 8/2012 | Jafari et al. |
| 2012/0216811 A1 | 8/2012 | Kimm et al. |
| 2012/0226444 A1 | 9/2012 | Milne et al. |
| 2012/0247471 A1 | 10/2012 | Masic et al. |
| 2012/0272960 A1 | 11/2012 | Milne |
| 2012/0272961 A1 | 11/2012 | Masic et al. |
| 2012/0272962 A1 | 11/2012 | Doyle et al. |
| 2012/0277616 A1 | 11/2012 | Sanborn et al. |
| 2012/0279501 A1 | 11/2012 | Wallace et al. |
| 2012/0304995 A1 | 12/2012 | Kauc |
| 2013/0000644 A1 | 1/2013 | Thiessen |
| 2013/0006133 A1 | 1/2013 | Doyle et al. |
| 2013/0006134 A1 | 1/2013 | Doyle et al. |
| 2013/0025596 A1 | 1/2013 | Jafari et al. |
| 2013/0025597 A1 | 1/2013 | Doyle et al. |
| 2013/0047989 A1 | 2/2013 | Vandine et al. |
| 2013/0053717 A1 | 2/2013 | Vandine et al. |
| 2013/0074844 A1 | 3/2013 | Kimm et al. |
| 2013/0081536 A1 | 4/2013 | Crawford, Jr. et al. |
| 2013/0104896 A1 | 5/2013 | Kimm et al. |
| 2013/0146055 A1 | 6/2013 | Jafari et al. |
| 2013/0167842 A1 | 7/2013 | Jafari et al. |
| 2013/0167843 A1 | 7/2013 | Kimm et al. |
| 2013/0192599 A1 | 8/2013 | Nakai et al. |
| 2013/0220324 A1 | 8/2013 | Jafari et al. |
| 2013/0255682 A1 | 10/2013 | Jafari et al. |
| 2013/0255685 A1 | 10/2013 | Jafari et al. |

FOREIGN PATENT DOCUMENTS

| | | |
|---|---|---|
| WO | WO 98/41267 | 9/1998 |
| WO | WO 98/41269 | 9/1998 |
| WO | WO 98/41270 | 9/1998 |
| WO | WO 98/41271 | 9/1998 |
| WO | WO 9853732 | 12/1998 |
| WO | WO 99/62403 | 12/1999 |
| WO | WO 00/45882 | 8/2000 |
| WO | WO 0079466 | 12/2000 |
| WO | WO 01/00264 | 1/2001 |
| WO | WO 01/00265 | 1/2001 |
| WO | WO 02/45566 | 6/2002 |
| WO | WO 02/095200 | 11/2002 |
| WO | WO 03/053503 | 7/2003 |
| WO | WO 03/102850 | 12/2003 |
| WO | WO 2004/030509 | 4/2004 |
| WO | WO 2004/069095 | 8/2004 |
| WO | WO 2004/070546 | 8/2004 |
| WO | WO 2004/070548 | 8/2004 |
| WO | WO 2004/070549 | 8/2004 |
| WO | WO 2004/070556 | 8/2004 |
| WO | WO 2004/070557 | 8/2004 |
| WO | WO 2004/070562 | 8/2004 |
| WO | WO 2004/070994 | 8/2004 |
| WO | WO 2004/070995 | 8/2004 |
| WO | WO 2004/082751 | 9/2004 |
| WO | WO 2005/050525 | 6/2005 |
| WO | WO 2005/051177 | 6/2005 |
| WO | WO 2006/012205 | 2/2006 |
| WO | WO 2007/050435 | 5/2007 |
| WO | WO 2007/085110 | 8/2007 |
| WO | WO 2007145948 | 12/2007 |
| WO | WO 2008/021222 | 2/2008 |
| WO | WO 2010/011928 | 1/2010 |

OTHER PUBLICATIONS

U.S. Appl. No. 12/775,565, Office Action mailed Oct. 30, 2012, 11 pgs.
U.S. Appl. No. 12/826,828, Office Action mailed Nov. 2, 2012, 17 pgs.
U.S. Appl. No. 12/826,847, Office Action mailed Nov. 2, 2012, 16 pgs.
U.S. Appl. No. 12/827,075, Office Action mailed Nov. 9, 2012, 16 pgs.
U.S. Appl. No. 12/827,130, Office Action mailed Nov. 9, 2012, 16 pgs.
U.S. Appl. No. 12/775,550, Advisory Action mailed Apr. 12, 2013, 3 pgs.
U.S. Appl. No. 12/775,565, Advisory Action mailed Apr. 9, 2013, 3 pgs.
U.S. Appl. No. 12/827,130, Office Action mailed May 8, 2013, 15 pgs.
U.S. Appl. No. 12/827,075, Office Action mailed Apr. 23, 2013, 17 pgs.
U.S. Appl. No. 12/826,847, Office Action mailed Apr. 24, 2013, 14 pgs.
U.S. Appl. No. 12/826,828, Office Action mailed Apr. 24, 2013, 15 pgs.
U.S. Appl. No. 12/955,422, Office Action mailed Apr. 23, 2013, 27 pgs.
U.S. Appl. No. 13/035,974, Office Action mailed Mar. 29, 2013, 14 pgs.
7200 Series Ventilator, Options, and Accessories: Operator's Manual. Nellcor Puritan Bennett, Part No. 22300 A, Sep. 1990, pp. 1-196.
7200 Ventilatory System: Addendum/Errata. Nellcor Puritan Bennett, Part No. 4-023576-00, Rev. A, Apr. 1988, pp. 1-32.
800 Operator's and Technical Reference Manual. Series Ventilator System, Nellcor Puritan Bennett, Part No. 4-070088-00, Rev. L, Aug. 2010, pp. 1-476.
840 Operator's and Technical Reference Manual. Ventilator System, Nellcor Puritan Bennett, Part No. 4-075609-00, Rev. G, Oct. 2006, pp. 1-424.
Egan's Fundamentals of Respiratory Care (2003) 8th Edition, Editors Robert L. Wilkins, James K. Stoller and Craig L. Scanlan, p. 996.
Mechanical Ventilation: Physiological and Clinical Applications (2006) 4th Edition, Editors Susan P. Pilbeam and J.M. Cairo, pp. 46-47, 144, 158-160, 168-171, 178-181, 195-202, 222-225, 373-376.
Puritan Bennett 840 Ventilator System SMARTER Breath Delivery information sheet by tyco Healthcare, undated, 1 page.
Sassoon, Catherine, MD., "Triggering of the Ventilator in Patient-Ventilator Interactions", Respiratory Care, Jan. 2011, vol. 56, No. 1, pp. 39-51.
The ARDSNET. "Ventilation with Lower Tidal Volumes as Compared with Traditional Tidal Volumes For Acute Lung Injury and the Acute Respiratory Distress Syndrome," New England Journal of Medicine, vol. 342 No. 18, May 4, 2000, pp. 1301-1308.
Thille, A., et al. "Patient-Ventilator Asynchrony During Assisted Mechanical Ventilation," Intensive Care Med. (2006) 32:1515-1522.
Tobin, M. "Principles and Practices of Mechanical Ventilation," Second Ed. McGraw Hill 2006. p. 1062.
U.S. Appl. No. 13/544,462 entitled "Systems and Methods for Missed Breath Detection and Indication", filed Jul. 9, 2012, 47 pgs.
U.S. Appl. No. 12/775,550, Office Action mailed Feb. 14, 2013, 32 pgs.
U.S. Appl. No. 12/775,565, Office Action mailed Feb. 14, 2013, 10 pgs.
U.S. Appl. No. 12/955,523, Office Action mailed Feb. 5, 2013, 8 pgs.
U.S. Appl. No. 12/955,422, Notice of Allowance mailed Oct. 8, 2013, 13 pgs.

(56) References Cited

OTHER PUBLICATIONS

U.S. Appl. No. 12/775,565, Office Action mailed Jun. 13, 2013, 8 pgs.
U.S. Appl. No. 12/955,523, Notice of Allowance mailed Jul. 15, 2013, 8 pgs.
Anzueto, A. et al., "Effects of prolonged controlled mechanical ventilation on diaphragmatic function in healthy adult baboons", *Crit Care Med*. 1997; 25(7): 1187-1190.
Chao, David C. et al., "Patient-ventilator trigger asynchrony in prolonged mechanical ventilation", *Chest*. 1997;112(6):1592-1599.
De Wit, Marjolein et al., "Ineffective triggering predicts increased duration of mechanical ventilation", *Crit Care Med*. 2009;37(10): 2740-2745.
De Wit, Marjolein, "Monitoring of patient ventilator interaction at the bedside", *Respiratory Care*. 2011;56(1):61-68.
Epstein, S.K., "Optimizing patient-ventilator synchrony", *Semin Respir Crit Care Med*. 2001;22(2):137-152.
Epstein, Scott K., "How often does patient-ventilator asynchrony occur and what are the consequences?", *Respiratory Care*. 2011;56:25-35.
Fabry, Ben et al., "An analysis of desynchronization between the spontaneously breathing patient and ventilator during inspiratory pressure support", *Chest*. 1995;107(5):1387-1394.
Hermans, Greet et al., "Increased duration of mechanical ventilation is associated with decreased diaphragmatic force: a prospective observational study", *Crit Care*, 2010;14:R127, pp. 1-10.
Nava, S. et al., "Patient ventilator interaction and inspiratory effort during pressure support ventilation in patients with different pathologies", *Eur Respir J*. 1997;10(1):177-183.
Pohlman, Mark C. et al., "Excessive tidal volume from breath stacking during lung-protective ventilation for acute lung injury", *Crit Care Med*. 2008;36(11):3019-3023.
Sassoon, Catherine, "Triggering of the ventilator in patient-ventilator interactions", *Respiratory Care*. 2011;56(1):39-51.
Siegel, Mark, MD, "Management of agitation in the intensive care unit", *Clin. Chest Med*. 2003; 24(4): 713-725.
Varon, Joseph et al., "Prevalence of patient ventilator asynchrony in critically ill patients", *Chest*. 1994; 106(2suppl):141S-144S. [Abstract].
Vignaux, Laurence et al., "Patient-ventilator asynchrony during non-invasive ventilation for acute respiratory failure: a multicenter study", *Intensive Care Med*. 2009;35(5):840-846.
Xirouchaki, N. et al., "Proportional assist ventilation with load-adjustable gain factors in critically ill patients: comparison with pressure support", *Int Care Med*. 2008; 34: 2026-2034.
U.S. Appl. No. 12/775,550, Office Action mailed Jul. 18, 2013, 37 pgs.
U.S. Appl. No. 12/775,565, Notice of Allowance mailed Sep. 18, 2013, 6 pgs.
U.S. Appl. No. 12/826,828, Notice of Allowance mailed Aug. 6, 2013, 4 pgs.
U.S. Appl. No. 12/826,847, Notice of Allowance mailed Aug. 5, 2013, 3 pgs.
U.S. Appl. No. 12/827,075, Notice of Allowance mailed Aug. 6, 2013, 3 pgs.
U.S. Appl. No. 12/827,130, Notice of Allowance mailed Aug. 8, 2013, 4 pgs.
U.S. Appl. No. 12/903,358, Office Action mailed Aug. 19, 2013, 15 pgs.
U.S. Appl. No. 12/955,368, Office Action mailed Aug. 2, 2013, 12 pgs.
U.S. Appl. No. 13/035,974, Office Action mailed Sep. 23, 2013, 14 pgs.

* cited by examiner

VENTILATOR-INITIATED PROMPT OR SETTING REGARDING DETECTION OF ASYNCHRONY DURING VENTILATION

A ventilator is a device that mechanically helps patients breathe by replacing some or all of the muscular effort required to inflate and deflate the lungs. In recent years, there has been an accelerated trend towards an integrated clinical environment. That is, medical devices are becoming increasingly integrated with communication, computing, and control technologies. As a result, modern ventilatory equipment has become increasingly complex, providing for detection and evaluation of a myriad of ventilatory parameters. However, due to the sheer magnitude of available ventilatory data, many clinicians may not readily assess and evaluate the diverse ventilatory data to detect certain patient conditions and/or changes in patient conditions, such as ventilator asynchrony. For example, extended periods of asynchrony can increase the amount of time patient needs to be ventilated by the ventilator.

Indeed, clinicians and patients may greatly benefit from ventilator notifications when evaluation of various ventilatory data is indicative of certain patient conditions, changes in patient conditions, effectiveness of ventilatory therapy, or otherwise.

Ventilator-Initiated Prompt or Setting Regarding Detection of Asynchrony During Ventilation of a Patient This disclosure describes systems and methods for monitoring and evaluating ventilatory parameters, analyzing ventilatory data associated with those parameters, and providing useful notifications and/or recommendations to clinicians. Modern ventilators monitor, evaluate, and graphically represent a myriad of ventilatory parameters. However, many clinicians may not easily identify or recognize data patterns and correlations indicative of certain patient conditions, changes in patient condition, and/or effectiveness of ventilatory treatment. Further, clinicians may not readily determine appropriate ventilatory adjustments that may address certain patient conditions and/or the effectiveness of ventilatory treatment. Specifically, clinicians may not readily detect or recognize the presence of asynchrony. According to embodiments, a ventilator may be configured to monitor and evaluate diverse ventilatory parameters to detect an asynchrony and may issue notifications and recommendations suitable for a patient to the clinician when asynchrony is implicated. The suitable notifications and recommendations may further be provided in a hierarchical format such that the clinician may selectively access summarized and/or detailed information regarding the presence of asynchrony. In more automated systems, recommendations may be automatically implemented.

According to embodiments, ventilator-implemented methods for detecting asynchrony are provided. The methods include collecting data associated with ventilatory parameters and processing the collected ventilatory parameter data based on background trigger type, wherein processing the collected ventilatory parameter data includes deriving ventilatory parameter data from the collected ventilatory parameter data based on a background trigger type. In some embodiments, the methods include determining that an asynchrony is implicated upon detecting that the processed ventilatory data breaches the one or more predetermined thresholds. When asynchrony is implicated, the methods include issuing a smart prompt.

According to further embodiments, a ventilatory system for issuing a smart prompt when asynchrony is implicated during ventilation of a patient is provided based on a background trigger type. An appropriate notification message and an appropriate recommendation message may be determined and either or both of the appropriate notification message and the appropriate recommendation message may be displayed.

According to further embodiments, a graphical user interface for displaying one or more smart prompts corresponding to a detected condition is provided. The graphical user interface includes at least one window and one or more elements within the at least one window comprising at least one smart prompt element for communicating information regarding the detected condition based on a background trigger type, wherein the detected condition is asynchrony.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the claims.

BRIEF DESCRIPTION OF THE DRAWINGS

The following drawing figures, which form a part of this application, are illustrative of described technology and are not meant to limit the scope of the claims in any manner, which scope shall be based on the claims appended hereto.

DETAILED DESCRIPTION

Although the techniques introduced above and discussed in detail below may be implemented for a variety of medical devices, the present disclosure will discuss the implementation of these techniques for use in a mechanical ventilator system. The reader will understand that the technology described in the context of a ventilator system could be adapted for use with other therapeutic equipment for alerting and advising clinicians regarding detected patient conditions.

This disclosure describes systems and methods for monitoring and evaluating ventilatory parameters, analyzing ventilatory data associated with those parameters, and providing useful notifications and/or recommendations to clinicians. Modern ventilators monitor, evaluate, and graphically represent a myriad of ventilatory parameters. However, many clinicians may not easily identify or recognize data patterns and correlations indicative of certain patient conditions, changes in patient condition, and/or effectiveness of ventilatory treatment. Further, clinicians may not readily determine appropriate ventilatory adjustments that may address certain patient conditions and/or the effectiveness of ventilatory treatment. Specifically, clinicians may not readily detect or recognize the presence of asynchrony during ventilation of a patient.

According to embodiments, a ventilator may be configured to monitor and evaluate diverse ventilatory parameters to detect asynchrony and may issue suitable notifications and recommendations to the clinician when asynchrony is implicated. The suitable notifications and recommendations may further be provided in a hierarchical format such that the clinician may selectively access summarized and/or detailed information regarding the presence of asynchrony. In more automated systems, recommendations may be automatically implemented.

Ventilator System

Figure 1:
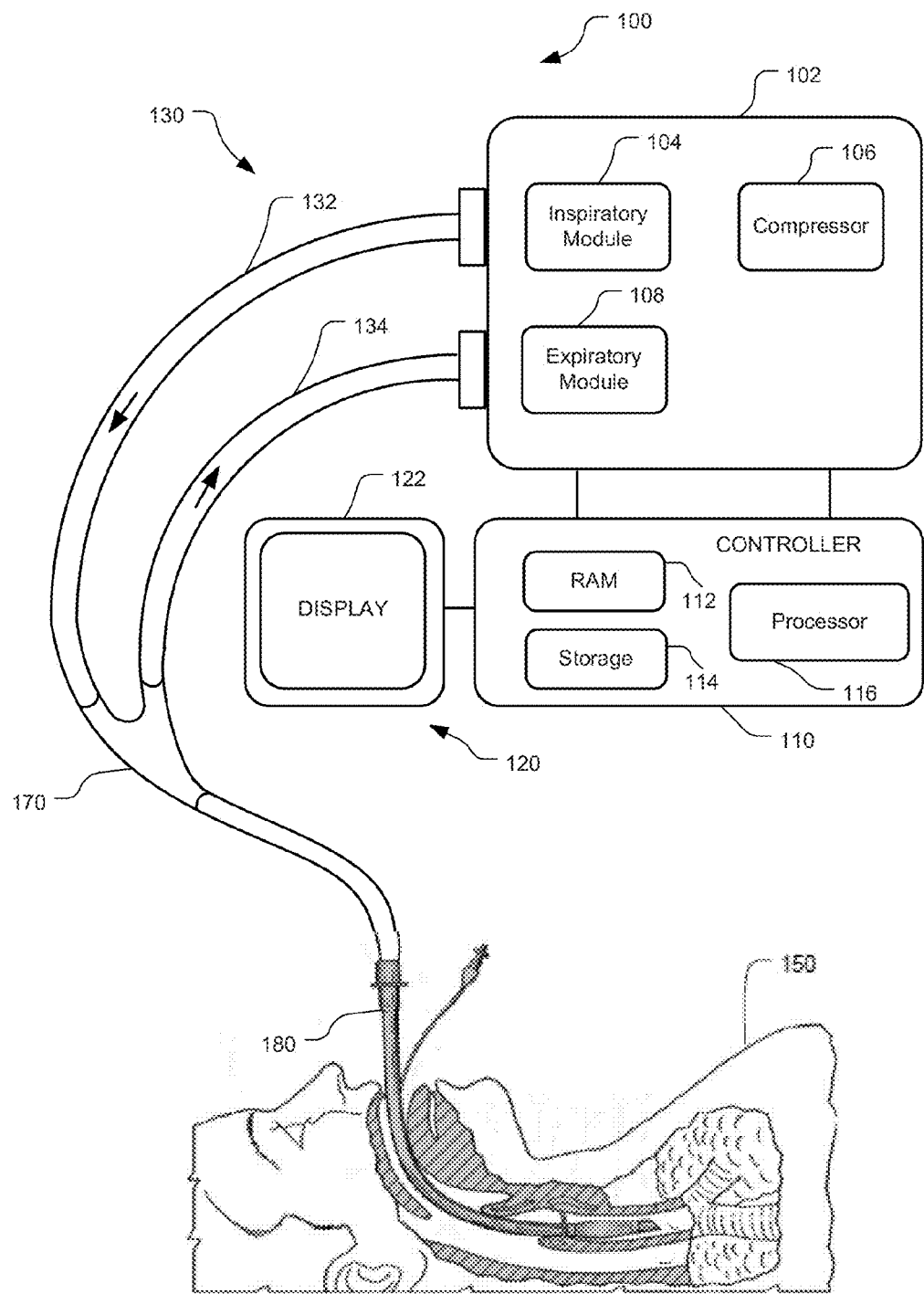
FIG. 1 is a diagram illustrating an embodiment of an exemplary ventilator connected to a human patient.

FIG. 1 is a diagram illustrating an embodiment of an exemplary ventilator 100 connected to a human patient 150. Ventilator 100 includes a pneumatic system 102 (also referred to as a pressure generating system 102) for circulating breathing gases to and from patient 150 via the ventilation tubing system 130, which couples the patient 150 to the pneumatic system 102 via an invasive (e.g., endotracheal tube, as shown) or a non-invasive (e.g., nasal mask) patient interface 180.

Ventilation tubing system 130 (or patient circuit 130) may be a two-limb (shown) or a one-limb circuit for carrying gases to and from the patient 150. In a two-limb embodiment, a fitting, typically referred to as a "wye-fitting" 170, may be provided to couple a patient interface 180 (as shown, an endotracheal tube) to an inspiratory limb 132 and an expiratory limb 134 of the ventilation tubing system 130.

Pneumatic system 102 may be configured in a variety of ways. In the present example, pneumatic system 102 includes an expiratory module 108 coupled with the expiratory limb 134 and an inspiratory module 104 coupled with the inspiratory limb 132. Compressor 106 or other source(s) of pressurized gases (e.g., air, oxygen, and/or helium) is coupled with inspiratory module 104 to provide a gas source for ventilatory support via inspiratory limb 132.

The pneumatic system 102 may include a variety of other components, including mixing modules, valves, sensors, tubing, accumulators, filters, etc. Controller 110 is operatively coupled with pneumatic system 102, signal measurement and acquisition systems, and an operator interface 120 that may enable an operator to interact with the ventilator 100 (e.g., change ventilator settings, select operational modes, breath types, view monitored parameters, etc.). Controller 110 may include memory 112, one or more processors 116, storage 114, and/or other components of the type commonly found in command and control computing devices. In the depicted example, operator interface 120 includes a display 122 that may be touch-sensitive and/or voice-activated, enabling the display 122 to serve both as an input and output device.

The memory 112 includes non-transitory, computer-readable storage media that stores software that is executed by the processor 116 and which controls the operation of the ventilator 100. In an embodiment, the memory 112 includes one or more solid-state storage devices such as flash memory chips.

In an alternative embodiment, the memory 112 may be mass storage connected to the processor 116 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 116. That is, computer-readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

Communication between components of the ventilatory 100 or between the ventilator 100 and other therapeutic equipment and/or remote monitoring systems may be conducted over a distributed network, as described further herein, via wired or wireless means. Further, the present methods may be configured as a presentation layer built over the TCP/IP protocol. TCP/IP stands for "Transmission Control Protocol/Internet Protocol" and provides a basic communication language for many local networks (such as intranets or extranets) and is the primary communication language for the Internet. Specifically, TCP/IP is a bi-layer protocol that allows for the transmission of data over a network. The higher layer, or TCP layer, divides a message into smaller packets, which are reassembled by a receiving TCP layer into the original message. The lower layer, or IP layer, handles addressing and routing of packets so that they are properly received at a destination.

Ventilator Components

Figure 2A:
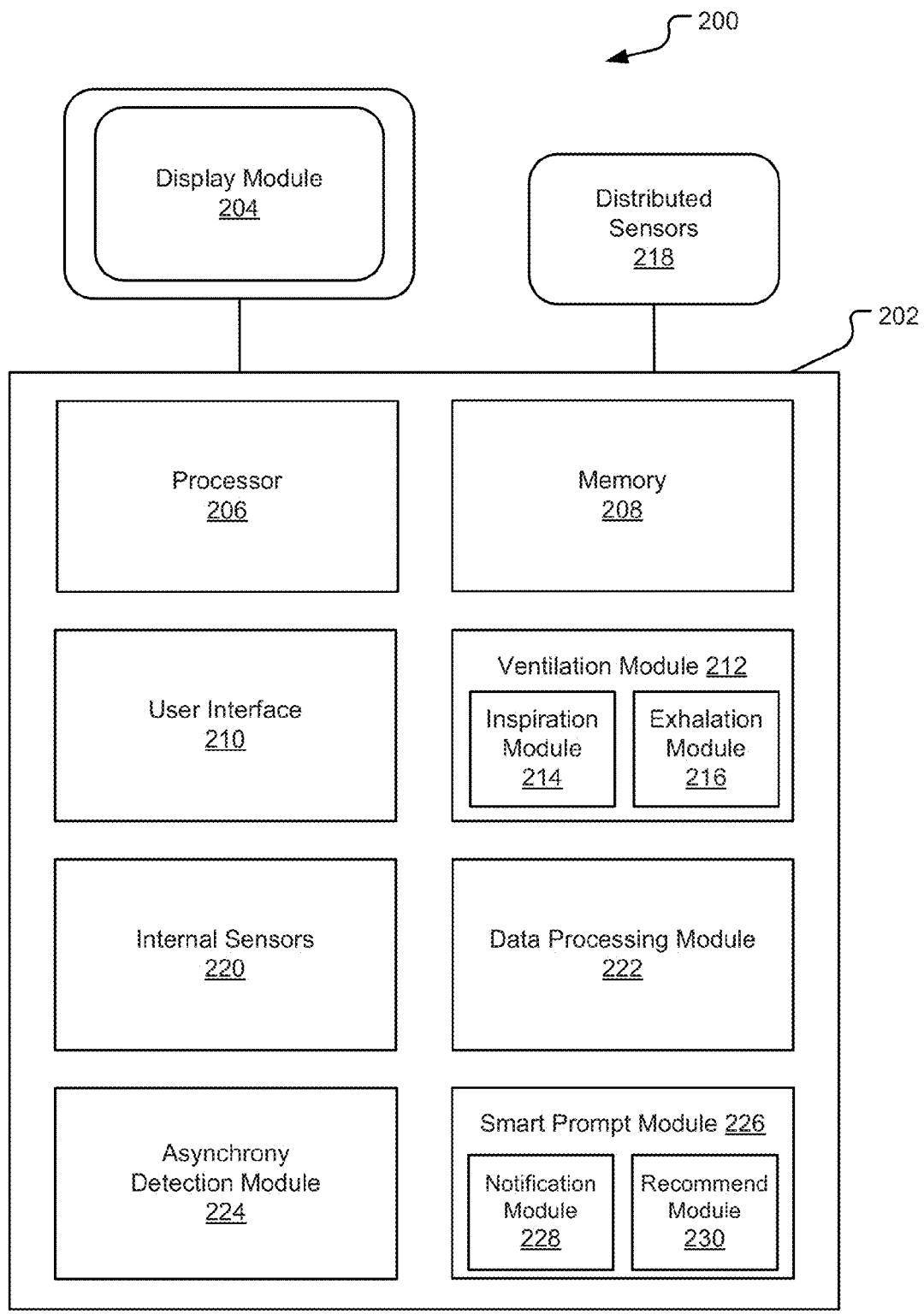
FIG. 2A is a block-diagram illustrating an embodiment of a ventilatory system for monitoring and evaluating ventilatory parameters associated with asynchrony.

FIG. 2A is a block-diagram illustrating an embodiment of a ventilatory system 200 for monitoring and evaluating ventilatory parameters associated with asynchrony. Ventilatory system 200 includes ventilator 202 with its various modules and components.

That is, ventilator 202 may further include, inter alia, memory 208, one or more processors 206, user interface 210, and ventilation module 212 (which may further include an inspiration module 214 and an exhalation module 216). Memory 208 is defined as described above for memory 112. Similarly, the one or more processors 206 are defined as described above for one or more processors 116. Processors 206 may further be configured with a clock whereby elapsed time may be monitored by the ventilatory system 200.

The ventilatory system 200 may also include a display module 204 communicatively coupled to ventilator 202. Display module 204 provides various input screens, for receiving clinician input, and various display screens, for presenting useful information to the clinician. The display module 204 is configured to communicate with user interface 210 and may include a graphical user interface (GUI). The GUI may be an interactive display, e.g., a touch-sensitive screen or otherwise, and may provide various windows (i.e., visual areas) comprising elements for receiving user input and interface command operations and for displaying ventilatory information (e.g., including ventilatory data, alerts, patient information, parameter settings, etc.). The elements may include controls, graphics, charts, tool bars, input fields, smart prompts, etc. Alternatively, other suitable means of communication with the ventilator 202 may be provided, for instance by a wheel, keyboard, mouse, or other suitable interactive device. Thus, user interface 210 may accept commands and input through display module 204. Display module 204 may also provide useful information in the form of various ventilatory data regarding the physical condition of a patient and/or a prescribed respiratory treatment. The useful information may be derived by the ventilator 202, based on data collected by a data processing module 222, and the useful information may be displayed to the clinician in the form of graphs, wave representations, pie graphs, or other suitable forms of graphic display. For example, one or more smart prompts may be displayed on the GUI and/or display module 204 upon detection of an implication of asynchrony by the ventilator. Additionally or alternatively, one or more smart prompts may be communicated to a remote monitoring system coupled via any suitable means to the ventilatory system 200.

Equation of Motion

Ventilation module 212 may oversee ventilation of a patient according to prescribed ventilatory settings. By way of general overview, the basic elements impacting ventilation may be described by the following ventilatory equation (also known as the Equation of Motion):

$$P_m + P_v = V_T/C + R*F$$

Here, $P_m$ is a measure of muscular effort that is equivalent to the pressure generated by the muscles of a patient. If the patient's muscles are inactive, the $P_m$ is equivalent to 0 cm $H_2O$. $P_m$ is calculated using the following equation: $P_m$=elastance×volume+resistance×flow. During inspiration, $P_v$ represents the positive pressure delivered by a ventilator (generally in cm $H_2O$). $V_T$ represents the tidal volume delivered, C refers to the respiratory compliance, R represents the respiratory resistance, and F represents the gas flow during inspiration (generally in liters per min (L/m)). Alternatively, during exhalation, the Equation of Motion may be represented as:

$$P_a + P_t = V_{TE}/C + R*F$$

Here, $P_a$ represents the positive pressure existing in the lungs (generally in cm $H_2O$), $P_t$ represents the transairway pressure, $V_{TE}$ represents the tidal volume exhaled, C refers to the respiratory compliance, R represents the respiratory resistance, and F represents the gas flow during exhalation (generally in liters per min (L/m)).

Pressure

For positive pressure ventilation, pressure at the upper airway opening (e.g., in the patient's mouth) is positive relative to the pressure at the body's surface (i.e., relative to the ambient atmospheric pressure to which the patient's body surface is exposed, about 0 cm $H_2O$). As such, when $P_v$ is zero, i.e., no ventilatory pressure is being delivered, the upper airway opening pressure will be equal to the ambient pressure (i.e., about 0 cm $H_2O$). However, when ventilatory pressure is applied, a pressure gradient is created that allows gases to flow into the airway and ultimately into the lungs of a patient during inspiration (or, inhalation).

According to embodiments, additional pressure measurements may be obtained and evaluated. For example, transairway pressure, $P_t$, which refers to the pressure differential or gradient between the upper airway opening and the alveoli, may also be determined. $P_t$ may be represented mathematically as:

$$P_t = P_{awo} - P_a$$

Where $P_{awo}$ refers to the pressure in the upper airway opening, or mouth, and $P_a$ refers to the pressure within the alveolar space, or the lungs (as described above). $P_t$ may also be represented as follows:

$$P_t = F*R$$

Where F refers to flow and R refers to respiratory resistance, as described below.

Additionally, lung pressure or alveolar pressure, $P_a$, may be measured or derived. For example, $P_a$ may be measured via a distal pressure transducer or other sensor near the lungs and/or the diaphragm. Alternatively, $P_a$ may be estimated by measuring the plateau pressure, $P_{Plat}$, via a proximal pressure transducer or other sensor at or near the airway opening. Plateau pressure, $P_{Plat}$, refers to a slight plateau in pressure that is observed at the end of inspiration when inspiration is held for a period of time, sometimes referred to as an inspiratory hold or pause maneuver, or a breath-hold maneuver. That is, when inspiration is held, pressure inside the alveoli and mouth are equal (i.e., no gas flow). However, as a result of muscular relaxation and elastance of the lungs during the hold period, forces are exerted on the inflated lungs that create a positive pressure. This positive pressure is observed as a plateau in the pressure waveform that is slightly below the peak inspiratory pressure, $P_{Peak}$, prior to initiation of exhalation. As may be appreciated, for accurate measurement of $P_{Plat}$, the patient should be sedated or non-spontaneous (as muscular effort during the inspiratory pause may skew the pressure measurement). Upon determining $P_{Plat}$ based on the pressure waveform or otherwise, $P_{Plat}$ may be used as an estimate of $P_a$ (alveolar pressure).

Flow and Volume

Volume refers to the amount of gas delivered to a patient's lungs, usually in liters (L) or milliliters (ml). Flow refers to a rate of change in volume over time ($F = \Delta V/\Delta t$). Flow is generally expressed in liters per minute (L/m or lpm) or milliliters per minute (mL/m) and, depending on whether gases are flowing into or out of the lungs, flow may be referred to as inspiratory flow or expiratory flow, respectively. According to embodiments, the ventilator may control the rate of delivery of gases to the patient, i.e., inspiratory flow, and may control the rate of release of gases from the patient, i.e., expiratory flow.

As may be appreciated, volume and flow are closely related. That is, where flow is known or regulated, volume may be derived based on elapsed time. Indeed, volume may be derived by integrating the flow waveform. According to embodiments, a tidal volume, $V_T$, may be delivered upon reaching a set inspiratory time ($T_I$) at set inspiratory flow. Alternatively, set $V_T$ and set inspiratory flow may determine the amount of time required for inspiration, i.e., $T_I$.

Respiratory Compliance

Additional ventilatory parameters that may be measured and/or derived may include respiratory compliance and respiratory resistance, which refer to the load against which the patient and/or the ventilator must work to deliver gases to the lungs. Respiratory compliance may be interchangeably referred to herein as compliance. Generally, compliance refers to a relative ease with which something distends and is the inverse of elastance, which refers to the tendency of something to return to its original form after being deformed. As related to ventilation, compliance refers to the lung volume achieved for a given amount of delivered pressure ($C = \Delta V/\Delta P$). Increased compliance may be detected when the ventilator measures an increased volume relative to the given amount of delivered pressure. Some lung diseases (e.g., acute respiratory distress syndrome (ARDS)) may decrease compliance and, thus, require increased pressure to inflate the lungs. Alternatively, other lung diseases may increase compliance, e.g., emphysema, and may require less pressure to inflate the lungs.

Additionally or alternatively, static compliance and dynamic compliance may be calculated. Static compliance, $C_S$, represents compliance impacted by elastic recoil at zero flow (e.g., of the chest wall, patient circuit, and alveoli). As elastic recoil of the chest wall and patient circuit may remain relatively constant, static compliance may generally represent compliance as affected by elastic recoil of the alveoli. As described above, $P_{Plat}$ refers to a slight plateau in pressure that is observed after relaxation of pleural muscles and elastic recoil, i.e., representing pressure delivered to overcome elastic forces. As such, $P_{Plat}$ provides a basis for estimating $C_S$ as follows:

$$C_S = V_T/(P_{Plat} - EEP)$$

Where $V_T$ refers to tidal volume, $P_{Plat}$ refers to plateau pressure, and EEP refers to end-expiratory pressure, or baseline pressure (including PEEP and/or Auto-PEEP). Note that proper calculation of $C_S$ depends on accurate measurement of $V_T$ and $P_{Plat}$.

Dynamic compliance, $C_D$, is measured during airflow and, as such, is impacted by both elastic recoil and airway resistance. Peak inspiratory pressure, $P_{Peak}$, which represents the highest pressure measured during inspiration, i.e., pressure delivered to overcome both elastic and resistive forces to inflate the lungs, is used to calculate $C_D$ as follows:

$$C_D = V_T/(P_{Peak} - EEP)$$

Where $V_T$ refers to tidal volume, $P_{Peak}$ refers to peak inspiratory pressure, and EEP refers to end-expiratory pressure. According to embodiments, ventilatory data may be more readily available for trending compliance of non-triggering patients than of triggering patients.

Respiratory Resistance

Respiratory resistance refers to frictional forces that resist airflow, e.g., due to synthetic structures (e.g., endotracheal tube, expiratory valve, etc.), anatomical structures (e.g., bronchial tree, esophagus, etc.), or viscous tissues of the lungs and adjacent organs. Respiratory resistance may be interchangeably referred to herein as resistance. Resistance is highly dependent on the diameter of the airway. That is, a larger airway diameter entails less resistance and a higher concomitant flow. Alternatively, a smaller airway diameter entails higher resistance and a lower concomitant flow. In fact, decreasing the diameter of the airway results in an exponential increase in resistance (e.g., two-times reduction of diameter increases resistance by sixteen times). As may be appreciated, resistance may also increase due to a restriction of the airway that is the result of, inter alia, increased secretions, bronchial edema, mucous plugs, bronchospasm, and/or kinking of the patient interface (e.g., invasive endotracheal or tracheostomy tubes).

Airway resistance may further be represented mathematically as:

$$R = P_t/F$$

Where $P_t$ refers to the transairway pressure and F refers to the flow. That is, $P_t$ refers to the pressure necessary to overcome resistive forces of the airway. Resistance may be expressed in centimeters of water per liter per second (i.e., cm $H_2O$/L/s).

Pulmonary Time Constant

As discussed above, compliance refers to the lung volume achieved for a given amount of delivered pressure ($C = \Delta V/\Delta P$). That is, stated differently, volume delivered is equivalent to the compliance multiplied by the delivered pressure ($\Delta V = C*\Delta P$). However, as the lungs are not perfectly elastic, a period of time is needed to deliver the volume $\Delta V$ at pressure $\Delta P$. A pulmonary time constant, $\tau$, may represent a time necessary to inflate or exhale a given percentage of the volume at delivered pressure $\Delta P$. The pulmonary time constant, $\tau$, may be calculated by multiplying the respiratory resistance by the respiratory compliance ($\tau = R*C$) for a given patient and $\tau$ is generally represented in seconds, s. The pulmonary time constant associated with exhalation of the given percentage of volume may be termed an expiratory time constant and the pulmonary time constant associated with inhalation of the given percentage of volume may be termed an inspiratory time constant.

According to some embodiments, when expiratory resistance data is available, the pulmonary time constant may be calculated by multiplying expiratory resistance by compliance. According to alternative embodiments, the pulmonary time constant may be calculated based on inspiratory resistance and compliance. According to further embodiments, the expiratory time, $T_E$, should be equal to or greater than three (3) pulmonary time constants to ensure adequate exhalation. That is, for a triggering patient, $T_E$ (e.g., determined by trending $T_E$ or otherwise) should be equal to or greater than 3 pulmonary time constants. For a non-triggering patient, set respiration rate (RR) should yield a $T_E$ that is equal to or greater than 3 pulmonary time constants.

Normal Resistance and Compliance

According to embodiments, normal respiratory resistance and compliance may be determined based on a patient's predicted body weight (PBW) (or ideal body weight (IBW)). That is, according to a standardized protocol or otherwise, patient data may be compiled such that normal respiratory resistance and compliance values and/or ranges of values may be determined and provided to the ventilatory system 200. That is, a manufacturer, clinical facility, clinician, or otherwise, may configure the ventilator with normal respiratory resistance and compliance values and/or ranges of values based on PBWs (or IBWs) of a patient population. Thereafter, during ventilation of a particular patient, respiratory resistance and compliance data may be trended for the patient and compared to normal values and/or ranges of values based on the particular patient's PBW (or IBW). According to embodiments, the ventilator may give an indication to the clinician regarding whether the trended respiratory resistance and compliance data of the particular patient falls into normal ranges. According to some embodiments, data may be more readily available for trending resistance and compliance for non-triggering patients than for triggering patients.

According to further embodiments, a predicted $T_E$ may be determined based on a patient's PBW (or IBW). That is, according to a standardized protocol or otherwise, patient population data may be compiled such that predicted $T_E$ values and/or ranges of values may be determined based on PBWs (or IBWs) of the patient population and provided to the ventilatory system 200. Actual (or trended) $T_E$ for a particular patient may then be compared to the predicted $T_E$. As noted previously, increased resistance and/or compliance may result in an actual $T_E$ that is longer than predicted $T_E$. However, when actual $T_E$ is consistent with predicted $T_E$, this may indicate that resistance and compliance for the particular patient fall into normal ranges.

According to further embodiments, a normal pulmonary time constant, $\tau$, may be determined based on a patient's PBW (or IBW). That is, according to a standardized protocol or otherwise, patient data may be compiled such that normal $\tau$ values and/or ranges of values may be determined based on PBWs (or IBWs) of a patient population and provided to the ventilatory system 200. A calculated τ may be determined for a particular patient by multiplying resistance by compliance (as described above, resistance and compliance data may be more readily available for a non-triggering patient). As the product of resistance and compliance results in τ, increased resistance and/or compliance may result in an elevated τ value. However, when the calculated τ value for the particular patient is consistent with the normal τ value, this may indicate that the resistance and compliance of the particular patient fall into normal ranges.

Inspiration

Ventilation module 212 may further include an inspiration module 214 configured to deliver gases to the patient according to prescribed ventilatory settings. Specifically, inspiration module 214 may correspond to the inspiratory module 104 or may be otherwise coupled to source(s) of pressurized gases (e.g., air, oxygen, and/or helium), and may deliver gases to the patient. Inspiration module 214 may be configured to provide ventilation according to various ventilatory breath types, e.g., via volume-targeted, pressure-targeted, or via any other suitable breath types.

The various ventilator breath types operate in different modes such as mandatory, mixed, and spontaneous modes. In some embodiments, the mode of operation is selected by the clinician. In other embodiments, the mode of operation is automatically determined by the ventilator. During the spontaneous mode of operation, a breath type delivers inspiration and exhalation upon the detection of inspiratory and/or expiratory effort by the patient according to the parameters of the breath type. However, for safety measures, a breath type in a spontaneous mode may deliver inspiration and expiration after a predetermined amount of time passes to insure that the patient receives breathing gas in the event the patient stops making inspiratory and/or expiratory patient efforts. During the mandatory mode of operation, a breath type delivers inspiration and exhalation according to parameters of the breath type regardless of patient inspiratory and expiratory efforts. During the mixed mode of operation, a breath type delivers inspiration and expiration to the patient according to the parameters of the breath type; however, if a patient inspiratory and/or expiratory effort is detected by the breath type during an mixed mode, the breath type will deliver an additional inspiration and/or expiration upon detection according to parameters of the breath type regardless of the next determined timing for delivery of inspiration and/or expiration by the breath type.

Volume ventilation refers to various forms of volume-targeted ventilation that regulate volume delivery to the patient. Different types of volume ventilation are available depending on the specific implementation of volume regulation. For example, for volume-cycled ventilation, an end of inspiration is determined based on monitoring the volume delivered to the patient. Volume ventilation may include volume-control (VC), volume-targeted-pressure-control (VC+), or volume-support (VS) breath types. Volume ventilation may be accomplished by setting a target volume, or prescribed tidal volume, $V_T$, for delivery to the patient. According to embodiments, prescribed $V_T$ and inspiratory time ($T_I$) may be set during ventilation start-up, based on the patient's PBW (or IBW). In this case, flow will be dependent on the prescribed $V_T$ and set $T_I$. Alternatively, prescribed $V_T$ and flow may be set and $T_I$ may result. According to some embodiments, a predicted $T_E$ may be determined based on normal respiratory and compliance values or value ranges based on the patient's PBW (or IBW). Additionally, a RR setting, generally in breaths/min, may be determined and configured. For a non-triggering patient, the set RR controls the timing for each inspiration. For a triggering patient, the RR setting applies if the patient stops triggering for some reason and/or the patient's triggered RR drops below a threshold level.

According to embodiments, during volume ventilation, as volume and flow are regulated by the ventilator, delivered $V_T$, flow waveforms (or flow traces), and volume waveforms may be constant and may not be affected by variations in lung or airway characteristics (e.g., respiratory compliance and/or respiratory resistance). Alternatively, pressure readings may fluctuate based on lung or airway characteristics. According to some embodiments, the ventilator may control the inspiratory flow and then derive volume based on the inspiratory flow and elapsed time. For volume-cycled ventilation, when the derived volume is equal to the prescribed $V_T$, the ventilator may initiate exhalation.

According to alternative embodiments, the inspiration module 214 may provide ventilation via a form of pressure ventilation. Pressure-targeted breath types may be provided by regulating the pressure delivered to the patient in various ways. For example, during pressure-cycled ventilation, an end of inspiration is determined based on monitoring the pressure delivered to the patient. Pressure ventilation may include a pressure-support (PS), a proportional assist (PA), tube compensation (TC), or a pressure-control (PC) breath type, for example. The proportional assist (PA) breath type provides pressure in proportion to the instantaneous patient effort during spontaneous ventilation and is based on the equation of motion. Pressure ventilation may also include various forms of bi-level (BL) pressure ventilation, i.e., pressure ventilation in which the inspiratory positive airway pressure (IPAP) is higher than the expiratory positive airway pressure (EPAP). Specifically, pressure ventilation may be accomplished by setting a target or prescribed pressure for delivery to the patient. During pressure ventilation, predicted $T_I$ may be determined based on normal respiratory and compliance values and on the patient's PBW (or IBW). According to some embodiments, a predicted $T_E$ may be determined based on normal respiratory and compliance values and based on the patient's PBW (or IBW). A respiratory rate (RR) setting may also be determined and configured. For a non-triggering patient, the set RR controls the timing for each inspiration. For a triggering patient, the RR setting applies if the patient stops triggering for some reason and/or patient triggering drops below a threshold RR level.

According to embodiments, during pressure ventilation, the ventilator may maintain the same pressure waveform at the mouth, $P_{awo}$, regardless of variations in lung or airway characteristics, e.g., respiratory compliance and/or respiratory resistance. However, the volume and flow waveforms may fluctuate based on lung and airway characteristics. As noted above, pressure delivered to the upper airway creates a pressure gradient that enables gases to flow into a patient's lungs. The pressure from which a ventilator initiates inspiration is termed the end-expiratory pressure (EEP) or "baseline" pressure. This pressure may be atmospheric pressure (about 0 cm $H_2O$), also referred to as zero end-expiratory pressure (ZEEP). However, commonly, the baseline pressure may be positive, termed positive end-expiratory pressure (PEEP). Among other things, PEEP may promote higher oxygenation saturation and/or may prevent alveolar collapse during exhalation. Under pressure-cycled ventilation, upon delivering the prescribed pressure the ventilator may initiate exhalation.

According to still other embodiments, a combination of volume and pressure ventilation may be delivered to a patient, e.g., volume-targeted-pressure-control (VC+) breath type. In particular, VC+ may provide benefits of setting a target $V_T$, while also allowing for monitoring variations in flow. In other embodiments, a positive feedback ventilation is delivered to the patient, e.g., a diaphragmatic electromyography adjusted (DEA) breath type, or an IE Sync breath type (IE Sync is a registered trademark of Nellcor Puritan Bennett, LLC located at 6135 Gunbarrel Avenue in Boulder, Colo. 80301). As will be detailed further below, variations in flow may be indicative of various patient conditions. The use of an IE Synch or DEA breath type provides for more sensitive trigger detection for spontaneously breathing patients compared to other utilized breath types.

Exhalation

Ventilation module 212 may further include an exhalation module 216 configured to release gases from the patient's lungs according to prescribed ventilatory settings. Specifically, exhalation module 216 may correspond to expiratory module 108 or may otherwise be associated with and/or controlling an expiratory valve for releasing gases from the patient. By way of general overview, a ventilator may initiate exhalation based on lapse of an inspiratory time setting ($T_I$) or other cycling criteria set by the clinician or derived from ventilator settings (e.g., detecting delivery of prescribed $V_T$ or prescribed pressure based on a reference trajectory). Upon initiating the expiratory phase, exhalation module 216 may allow the patient to exhale by opening an expiratory valve. As such, exhalation is passive, and the direction of airflow, as described above, is governed by the pressure gradient between the patient's lungs (higher pressure) and the ambient surface pressure (lower pressure). Although expiratory flow is passive, it may be regulated by the ventilator based on the size of the expiratory valve opening. In some embodiments, exhalation is regulated based on a selected breath type.

Expiratory time ($T_E$) is the time from the end of inspiration until the patient triggers for a spontaneously breathing patient. The cycle detection for exhalation may be based on a selected trigger type. For a non-triggering patient, the $T_E$ is the time from the end of inspiration until the next inspiration based on the set RR. In some cases, however, the time required to return to the functional residual capacity (FRC) or resting capacity of the lungs is longer than provided by $T_E$ (e.g., because the patient triggers prior to fully exhaling or the set RR is too high for a non-triggering patient). According to embodiments, various ventilatory settings may be adjusted to better match the time to reach FRC with the time available to reach FRC. For example, increasing flow will shorten $T_I$, thereby increasing the amount of time available to reach FRC. Alternatively, $V_T$ may be decreased, resulting in less time required to reach FRC.

As may be further appreciated, at the point of transition between inspiration and exhalation, the direction of airflow may abruptly change from flowing into the lungs to flowing out of the lungs or vice versa depending on the transition. Stated another way, inspiratory flow may be measurable in the ventilatory circuit until $P_{Peak}$ is reached, at which point flow is zero. Thereafter, upon initiation of exhalation, expiratory flow is measurable in the ventilatory circuit until the pressure gradient between the lungs and the body's surface reaches zero (again, resulting in zero flow). However, in some cases, as will be described further herein, expiratory flow may still be positive, i.e., measurable, at the end of exhalation (termed positive end-expiratory flow or positive EEF). In this case, positive EEF is an indication that the pressure gradient has not reached zero or, similarly, that the patient has not completely exhaled. Although a single occurrence of premature inspiration may not warrant concern, repeated detection of positive EEF may be indicative of Auto-PEEP.

Ventilator Synchrony and Patient Triggering

According to some embodiments, the inspiration module 214 and/or the exhalation module 216 may be configured to synchronize ventilation with a spontaneously-breathing, or triggering, patient. That is, the ventilator may be configured to detect patient effort and may initiate a transition from exhalation to inspiration (or from inspiration to exhalation) in response. Triggering refers to the transition from exhalation to inspiration in order to distinguish it from the transition from inspiration to exhalation (referred to as cycling). Ventilation systems, depending on their breath type, may trigger and/or cycle automatically, or in response to a detection of patient effort, or both.

In the medical device field, "patient effort" is a term that can be used to describe many different patient parameters. To be clear, for the purposes of this document, the term "patient effort" shall be used herein to mean a patient's spontaneous attempt to initiate an inspiration or an exhalation as determined by an analysis of pressure, flow, volume, etc. measured by the ventilator. For example, a drop in pressure of greater than a threshold amount may be detected and identified as a single effort of the patient to initiate an inspiration. At times, the phrase "patient inspiratory effort" or "patient expiratory effort" will be used instead of patient effort to remind the reader that what is meant is an attempt by the patient to change the phase of respiratory cycle.

There are several different trigger types or systems and/methods utilized by the ventilator for detecting patient triggers and/or cycles. Once a breath type is selected, the trigger type utilized by the breath type for detecting patient effort may be selected. In some embodiments, the trigger type utilized by the breath type is automatically selected by the ventilator. In other embodiments, the trigger type utilized by the breath type is selected by the operator.

Any suitable type of triggering detection for determining a patient trigger may be utilized by the ventilator, such as nasal detection, diaphragm detection, and/or brain signal detection. Further, the ventilator may detect patient triggering via a pressure-monitoring method, a flow-monitoring method, direct or indirect measurement of neuromuscular signals, or any other suitable method. Internal sensors 220 and/or distributed sensors 218 suitable for this detection may include any suitable sensing device as known by a person of skill in the art for a ventilator. In addition, the sensitivity of the ventilator to changes in pressure and/or flow may be adjusted such that the ventilator may properly detect the patient effort, i.e., the lower the pressure or flow change setting the more sensitive the ventilator may be to patient triggering.

According to embodiments, a pressure-triggering method may involve the ventilator monitoring the circuit pressure, as described above, and detecting a slight drop in circuit pressure. The slight drop in circuit pressure may indicate that the patient's respiratory muscles, $P_m$, are creating a slight negative pressure gradient between the patient's lungs and the airway opening in an effort to inspire. The ventilator may interpret the slight drop in circuit pressure as patient effort and may consequently initiate inspiration by delivering respiratory gases.

Alternatively, the ventilator may detect a flow-triggered event. Specifically, the ventilator may monitor the circuit flow, as described above. If the ventilator detects a slight drop in flow during exhalation, this may indicate, again, that the patient is attempting to inspire. In this case, the ventilator is detecting a drop in bias flow (or baseline flow) attributable to a slight redirection of gases into the patient's lungs (in response to a slightly negative pressure gradient as discussed above). Bias flow refers to a constant flow existing in the circuit during exhalation that enables the ventilator to detect expiratory flow changes and patient triggering. For example, while gases are generally flowing out of the patient's lungs during exhalation, a drop in flow may occur as some gas is redirected and flows into the lungs in response to the slightly negative pressure gradient between the patient's lungs and the body's surface. Thus, when the ventilator detects a slight drop in flow below the bias flow by a predetermined threshold amount (e.g., 2 L/min below bias flow), it may interpret the drop as a patient trigger and may consequently initiate inspiration by delivering respiratory gases.

Further, in some embodiments, the trigger type may be an "active trigger type" or a "background trigger type". The active trigger type determines when to deliver inspiration and/or expiration to the patient during ventilation by the ventilator and the ventilator actively delivers inspiration and/or expiration based on this determination. A background trigger type determines when to deliver inspiration and/or expiration to the patient during ventilation by the ventilator but the ventilator does not actively deliver inspiration and/or expiration based on this determination and is, therefore, merely running in the background. Any trigger type described herein may be an active trigger type or a background trigger type.

Volume-Control Breath Type

In some embodiments, ventilation module 212 may further include an inspiration module 214 configured to deliver gases to the patient according to volume-control (VC). The VC breath type allows a clinician to set a respiratory rate and to select a volume to be administered to a patient during a mandatory breath. When using VC, a clinician sets a desired tidal volume, flow wave form shape, and an inspiratory flow rate or inspiratory time. These variables determine how much volume of gas is delivered to the patient and the duration of inspiration during each mandatory breath inspiratory phase. The mandatory breaths are administered according to the set respiratory rate.

For VC, when the delivered volume is equal to the prescribed tidal volume, the ventilator may initiate exhalation. Exhalation lasts from the time at which prescribed volume is reached until the start of the next ventilator mandated inspiration. This exhalation time is determined by the respiratory rate set by the clinician and any participation above the set rate by the patient. Upon the end of exhalation, another VC mandatory breath is given to the patient.

During VC, delivered volume and flow waveforms may remain constant and may not be affected by variations in lung or airway characteristics. Alternatively, pressure readings may fluctuate based on lung or airway characteristics. According to some embodiments, the ventilator may control the inspiratory flow and then derive volume based on the inspiratory flow and elapsed time.

In some embodiments, VC may also be delivered to a triggering patient. When VC is delivered to a triggering patient, the breath period (i.e. time between breaths) is a function of the frequency at which the patient is triggering breaths. That is, the ventilator will trigger the inhalation based upon the respiratory rate setting or the patient effort. If no patient effort is detected, the ventilator will deliver another mandatory breath at the predetermined respiratory rate. A patient-initiated mandatory (PIM) breath is a control breath that is triggered by the patient during a control mode such as VC or PC.

Volume-Targeted-Pressure-Control Breath Type

In further embodiments, ventilation module 212 may further include an inspiration module 214 configured to deliver gases to the patient using a volume-targeted-pressure-control (VC+) breath type. The VC+ breath type is a combination of volume and pressure control breath types that may be delivered to a patient as a mandatory breath. In particular, VC+ may provide the benefits associated with setting a target tidal volume, while also allowing for variable flow. Variable flow may be helpful in meeting inspiratory flow demands for actively breathing patients.

As may be appreciated, when resistance increases it becomes more difficult to pass gases into and out of the lungs, decreasing flow. For example, when a patient is intubated, i.e., having either an endotracheal or a tracheostomy tube in place, resistance may be increased as a result of the smaller diameter of the tube over a patient's natural airway. In addition, increased resistance may be observed in patients with obstructive disorders, such as COPD, asthma, etc. Higher resistance may necessitate, inter alia, a higher inspiratory time setting for delivering a prescribed pressure or volume of gases, a lower respiratory rate resulting in a higher expiratory time for complete exhalation of gases.

Unlike VC, when the set inspiratory time is reached, the ventilator may initiate exhalation. Exhalation lasts from the end of inspiration until the beginning of the next inspiration. For a non-triggering patient, the expiratory time ($T_E$) is based on the respiratory rate set by the clinician. Upon the end of exhalation, another VC+ mandatory breath is given to the patient.

By controlling target tidal volume and allowing for variable flow, VC+ allows a clinician to maintain the volume while allowing the flow and pressure targets to fluctuate.

Volume-Support Breath Type

In some embodiments, ventilation module 212 may further include an inspiration module 214 configured to deliver gases to the patient according to volume-support (VS) breath type. The VS breath type is utilized in the present disclosure as a spontaneous breath. VS is generally used with a triggering (spontaneously breathing) patient when the patient is ready to be weaned from a ventilator or when the patient cannot do all of the work of breathing on his or her own. When the ventilator senses patient inspiratory effort, the ventilator delivers a set tidal volume during inspiration. The tidal volume may be set and adjusted by the clinician. The patient controls the rate, inspiratory flow, and has some control over the inspiratory time. The ventilator then adjusts the pressure over several breaths to achieve the set tidal volume. When the machine senses a decrease in flow, or inspiration time reaches a predetermined limit, the ventilator determines that inspiration is ending. When delivered as a spontaneous breath, exhalation in VS lasts from a determination that inspiration is ending until the ventilator senses a next patient effort to breath.

Pressure-Control Breath Type

In additional embodiments, ventilation module 212 may further include an inspiration module 214 configured to deliver gases to the patient according to the pressure-control (PC) breath type. PC allows a clinician to select a pressure to be administered to a patient during a mandatory breath. When using the PC breath type, a clinician sets a desired pressure, inspiratory time, and respiratory rate for a patient. These variables determine the pressure of the gas delivered to the patient during each mandatory breath inspiration. The mandatory breaths are administered according to the set respiratory rate.

For the PC breath type, when the inspiratory time is equal to the prescribed inspiratory time, the ventilator may initiate exhalation. Exhalation lasts from the end of inspiration until the next inspiration. Upon the end of exhalation, another PC mandatory breath is given to the patient.

During PC breaths, the ventilator may maintain the same pressure waveform at the mouth, regardless of variations in lung or airway characteristics, e.g., respiratory compliance and/or respiratory resistance. However, the volume and flow waveforms may fluctuate based on lung and airway characteristics.

In some embodiments, PC may also be delivered for triggering patients. When PC is delivered with triggering, the breath period (i.e. time between breaths) is a function of the respiratory rate of the patient. The ventilator will trigger the inhalation based upon the respiratory rate setting or the patient's trigger effort, but cycling to exhalation will be based upon elapsed inspiratory time. The inspiratory time is set by the clinician. The inspiratory flow is delivered based upon the pressure setting and patient physiology. Should the patient create an expiratory effort in the middle of the mandatory inspiratory phase, the ventilator will respond by reducing flow. If no patient effort is detected, the ventilator will deliver another mandatory breath at the predetermined respiratory rate.

PC with triggering overcomes some of the problems encountered by other mandatory breath types that use artificially set inspiratory flow rates. For example, if the inspiratory flow is artificially set lower than a patient's demand, the patient will feel starved for flow. This can lead to undesirable effects, including increased work of breathing. In addition, should the patient begin to exhale when using one of the traditional mandatory breath types, the patient's expiratory effort is ignored since the inspiratory flow is mandated by the ventilator settings.

Pressure-Support Breath Type

In further embodiments, ventilation module 212 may further include an inspiration module 214 configured to deliver gases to the patient according to a pressure-support (PS) breath type. PS is a form of assisted ventilation and is utilized in the present disclosure during a spontaneous breath. PS is a patient triggered breath and is typically used when a patient is ready to be weaned from a ventilator or for when patients are breathing spontaneously but cannot do all the work of breathing on their own. When the ventilator senses patient inspiratory effort, the ventilator provides a constant pressure during inspiration. The pressure may be set and adjusted by the clinician. The patient controls the rate, inspiratory flow, and to an extent, the inspiratory time. The ventilator delivers the set pressure and allows the flow to vary. When the machine senses a decrease in flow, or determines that inspiratory time has reached a predetermined limit, the ventilator determines that inspiration is ending. When delivered as a spontaneous breath, exhalation in PS lasts from a determination that inspiration is ending until the ventilator senses a patient effort to breath.

Proportional Assist Breath Type

In mechanical ventilation, a proportional assist (PA) breath type refers to a type of ventilation in which the ventilator acts as an inspiratory amplifier that provides pressure support based on the patient's work of breathing (WOB). The degree of amplification (the "support setting") is set by an operator, for example, as a percentage based on the patient's WOB. In one implementation of a PA breath type, the ventilator may continuously monitor the patient's instantaneous inspiratory flow and instantaneous net lung volume, which are indicators of the patient's inspiratory WOB. These signals, together with ongoing estimates of the patient's lung compliance and lung resistance, allow the ventilator to compute a patient WOB and derive therefrom a target pressure to provide the support that assists the patient's inspiratory muscles to the degree selected by the operator as the support setting.

Various methods are known for calculation of patient WOB and any suitable method may be used. For example, methods exist that calculate patient WOB from sensors attached to the body to detect neural or muscular activity as well as methods that determine a patient WOB based on respiratory flow, respiratory pressure or a combination of both flow and pressure.

In a PA breath type, the patient's work of breathing, the elastic work of breathing component, and/or the resistive WOB component may be estimated by inputting measurements from various internal sensors 220 and/or distributed sensors 218 into the breathing algorithms. Typically, none of the instantaneous inspiratory pressure, the instantaneous flow, or the resulting volume are set by the caregiver. Because the PA breath type harmoniously links the ventilator to the patient, the patient effectively "drives" the ventilator. By appropriately setting the value of the proportionality (% support or support setting) control, the caregiver may effectively partition the total work of breathing between the patient and the ventilator.

Tube Compensation Breath Type

A Tube Compensation (TC) breath type is similar to the PA breath type. The TC breath type delivers breathing gases to a spontaneously-breathing patient with the objective of reducing the patient's work of breathing imposed by an artificial airway. During a TC breath type, the ventilator compensates for the load associated with breathing through an endotracheal or tracheostomy tube. The TC breath type calculates a tube resistance based on the tube type (endotracheal or tracheostomy) and the tube's internal diameter (tube$_{I.D.}$), which are settings input by the clinician. A tube compensation pressure is then calculated by the ventilator during the TC breath type as a function of the patient's monitored flow, the calculated tube resistance, and a percent support setting (also known as support setting) input by the clinician. During inhalation, the ventilator during the TC breath type delivers the tube compensation pressure plus a set PEEP to the patient airway. Upon reaching an expiration sensitivity ($E_{SENS}$) setting (or other cycling criteria), the ventilator during the TC breath type initiates exhalation. As with other pressure-based breath types, the ventilator during the TC breath type does not target a set $V_T$ or flow pattern.

Expiratory Sensitivity

As discussed above, ventilation module 212 may oversee ventilation of a patient according to prescribed ventilatory settings. In one embodiment, the expiratory sensitivity ($E_{SENS}$) is set by a clinician or operator. According to embodiments, $E_{SENS}$ sets the percentage of delivered peak inspiratory flow necessary to terminate inspiration and initiate exhalation. In some embodiments, the clinician or operator determines the $E_{SENS}$ setting, which is adjustable from 1% to 80%. A lower set $E_{SENS}$ increases inspiration time and a higher set $E_{SENS}$ decreases inspiration time. The $E_{SENS}$ setting may be utilized to limit unnecessary expiratory work and to improve patient-ventilator synchrony.

IE Sync Breath Type

The IE Sync breath delivers inspiration and expiration during ventilation of a spontaneously breathing patient based on monitored or estimated intrapleural pressure. The term "intrapleural pressure," as used herein, refers generally to the pressure exerted by the patient's diaphragm on the cavity in the thorax that contains the lungs, or the pleural cavity, and should further represent estimates of the pressure and/or any derivatives thereof. The use of intrapleural pressure is an effective way to determine inspiratory and expiratory patient effort. When a patient makes an effort to breathe, the patient's diaphragm will contract, and decrease the intrapleural pressure in order to draw air (or another substance) into the lungs. Because the contraction of the diaphragm is the effect of patient effort, the intrapleural pressure change is the first and a direct way to determine patient effort, as a pressure/flow change will happen subsequently. Therefore, a trigger detection application that uses intrapleural pressure is more sensitive to patient efforts than a trigger detection application that only uses pressure or flow. Accordingly, the IE Sync breath type promotes patient-ventilator synchrony. The improved synchrony provided by the IE Sync breath type minimizes patient discomfort.

The triggering described above based on intrapleural pressure as utilized by the IE Sync breath type is an additional trigger type. Accordingly, this IE Sync trigger type (or intrapleural pressure trigger type) may be an active trigger type (i.e., when utilized during the IE Sync breath type to deliver ventilation) or a background trigger type (when utilized in background).

Intrapleural pressure is estimated by the IE Sync algorithm according to any suitable method either known or discovered in the future. The intrapleural pressure estimates and their associated values can be utilized to monitor ventilation in all modes. In some embodiments, the IE Sync breath type derives intrapleural pressure readings from other data and measurements according to mathematical operations or otherwise. For example, an algorithm that estimates how the patient's intrapleural pressure is changing in real-time or quasi-real based on measured pressure and flow may be used. In one embodiment, an algorithm utilizes measured pressure, inlet flow, and outlet flow to determine intrapleural pressure. In some embodiments, the measured pressure and flow are derived from data taken by internal sensors 220 and distributed sensors 218. An example algorithm for determining intrapleural pressure is described in U.S. patent application Ser. No. 12/980,583 filed Dec. 29, 2010. Accordingly, U.S. patent application Ser. No. 12/980,583 filed on Dec. 29, 2010, is incorporated herein by reference in its entirety.

Diaphragmatic Electromyography Adjust Breath Type

The DEA breath delivers inspiration and expiration during ventilation of a spontaneously breathing patient based on monitored neural respiratory output for the diaphragm, which is monitored with an electromyograph. The neural respiratory output, which the act of breathing depends on, is the result of a rhythmic discharge from the center of brain. The discharge is carried to the diaphragm muscles cells via the phrenic nerve causing the diaphragm muscles to contract. The contraction of diaphragm muscles causes the lungs to expand dropping pressure in the airways of lungs to provide an inflow of air into the lungs.

The neural output is the captured electrical activity of the diaphragm (Edi). The Edi is then fed to the ventilator and used by the ventilator to assist the patient's breathing. The Edi curve and its associated values can be utilized to monitor ventilation in all modes. For example, the Edi curve and its associated values may be utilized to determine respiratory drive, volume requirements, effect of a ventilation setting, and gain indications for sedation and weaning.

Because the ventilator and the diaphragm are triggered utilizing the same signal, the mechanical coupling between the ventilator and the diaphragm is almost instantaneous. The Edi signal may be utilized to trigger inspiration and expiration; therefore, the DEA breath type promotes patient-ventilator synchrony. Further, with the DEA breath type the patient's own respiratory demand is utilized to determine the level of assistance helping to provide the correct breathing assistance to the patient. Accordingly, the improved synchrony provided by the DEA breath type minimizes patient discomfort.

The triggering described above based on Edi and utilized by the DEA breath type is an additional trigger type. Accordingly, this DEA trigger type (or Edi trigger type) may be an active trigger type (i.e., when utilized during the DEA breath type to deliver ventilation) or a background trigger type (when utilized in the background).

Ventilator Sensory Devices

The ventilatory system 200 may also include one or more distributed sensors 218 communicatively coupled to ventilator 202. Distributed sensors 218 may communicate with various components of ventilator 202, e.g., ventilation module 212, internal sensors 220, data processing module 222, asynchrony detection module 224, and any other suitable components and/or modules. Distributed sensors 218 may detect changes in ventilatory parameters indicative of asynchrony, for example. Distributed sensors 218 may be placed in any suitable location, e.g., within the ventilatory circuitry or other devices communicatively coupled to the ventilator. For example, sensors may be affixed to the ventilatory tubing or may be imbedded in the tubing itself. According to some embodiments, sensors may be provided at or near the lungs (or diaphragm) for detecting a pressure in the lungs. Additionally or alternatively, sensors may be affixed or imbedded in or near wye-fitting 170 and/or patient interface 180, as described above.

Distributed sensors 218 may further include pressure transducers that may detect changes in circuit pressure (e.g., electromechanical transducers including piezoelectric, variable capacitance, or strain gauge). Distributed sensors 218 may further include various flowmeters for detecting airflow (e.g., differential pressure pneumotachometers). For example, some flowmeters may use obstructions to create a pressure decrease corresponding to the flow across the device (e.g., differential pressure pneumotachometers) and other flowmeters may use turbines such that flow may be determined based on the rate of turbine rotation (e.g., turbine flowmeters). Alternatively, sensors may utilize optical or ultrasound techniques for measuring changes in ventilatory parameters. A patient's blood parameters or concentrations of expired gases may also be monitored by sensors to detect physiological changes that may be used as indicators to study physiological effects of ventilation, wherein the results of such studies may be used for diagnostic or therapeutic purposes. Indeed, any distributed sensory device useful for monitoring changes in measurable parameters during ventilatory treatment may be employed in accordance with embodiments described herein.

Ventilator 202 may further include one or more internal sensors 220. Similar to distributed sensors 218, internal sensors 220 may communicate with various components of ventilator 202, e.g., ventilation module 212, internal sensors 220, data processing module 222, asynchrony detection module 224, and any other suitable components and/or modules. Internal sensors 220 may employ any suitable sensory or derivative technique for monitoring one or more parameters associated with the ventilation of a patient. However, the one or more internal sensors 220 may be placed in any suitable internal location, such as, within the ventilatory circuitry or within components or modules of ventilator 202. For example, sensors may be coupled to the inspiratory and/or expiratory modules for detecting changes in, for example, circuit pressure and/or flow. Specifically, internal sensors 220 may include pressure transducers and flowmeters for measuring changes in circuit pressure and airflow. Additionally or alternatively, internal sensors 220 may utilize optical or ultrasound techniques for measuring changes in ventilatory parameters. For example, a patient's expired gases may be monitored by internal sensors 220 to detect physiological changes indicative of the patient's condition and/or treatment, for example. Indeed, internal sensors 220 may employ any suitable mechanism for monitoring parameters of interest in accordance with embodiments described herein.

As should be appreciated, with reference to the Equation of Motion, ventilatory parameters are highly interrelated and, according to embodiments, may be either directly or indirectly monitored. That is, parameters may be directly monitored by one or more sensors, as described above, or may be indirectly monitored by derivation according to the Equation of Motion.

Ventilatory Data

Ventilator 202 may further include a data processing module 222. As noted above, distributed sensors 218 and internal sensors 220 may collect data regarding various ventilatory parameters. Ventilator data refers to any ventilatory parameter or setting. A ventilatory parameter refers to any factor, characteristic, or measurement associated with the ventilation of a patient, whether monitored by the ventilator or by any other device. A ventilatory setting refers to any factor, characteristic, or measurement that is set by the ventilator and/or operator. Sensors may further transmit collected data to the data processing module 222 and, according to embodiments, the data processing module 222 may be configured to collect data regarding some ventilatory parameters, to derive data regarding other ventilatory parameters, and to graphically represent collected and derived data to the clinician and/or other modules of the ventilatory system 200. Some collected, derived, and/or graphically represented data may be indicative of asynchrony. For example, data regarding expiratory time, exhaled tidal volume, inspiratory time setting ($T_I$), etc., may be collected, derived, and/or graphically represented by data processing module 222.

Flow Data

For example, according to embodiments, data processing module 222 may be configured to monitor inspiratory and expiratory flow. Flow may be measured by any appropriate, internal or distributed device or sensor within the ventilatory system 200. As described above, flowmeters may be employed by the ventilatory system 200 to detect circuit flow. However, any suitable device either known or developed in the future may be used for detecting airflow in the ventilatory circuit.

Data processing module 222 may be further configured to plot monitored flow data graphically via any suitable means. For example, according to embodiments, flow data may be plotted versus time (flow waveform), versus volume (flow-volume loop), or versus any other suitable parameter as may be useful to a clinician. According to embodiments, flow may be plotted such that each breath may be independently identified. Further, flow may be plotted such that inspiratory flow and expiratory flow may be independently identified, e.g., inspiratory flow may be represented in one color and expiratory flow may be represented in another color. According to additional embodiments, flow waveforms and flow-volume loops, for example, may be represented alongside additional graphical representations, e.g., representations of volume, pressure, etc., such that clinicians may substantially simultaneously visualize a variety of ventilatory parameters associated with each breath.

As may be appreciated, flow decreases as resistance increases, making it more difficult to pass gases into and out of the lungs (i.e., $F=P_l/R$). For example, when a patient is intubated, i.e., having either an endotracheal or a tracheostomy tube in place, resistance may be increased as a result of the smaller diameter of the tube over a patient's natural airway. In addition, increased resistance may be observed in patients with obstructive disorders, such as COPD, asthma, etc. Higher resistance may necessitate, inter alia, a higher inspiratory time setting ($T_I$) for delivering a prescribed pressure or volume of gases, a higher flow setting for delivering prescribed pressure or volume, a lower respiratory rate resulting in a higher expiratory time ($T_E$) for complete exhalation of gases, etc.

Specifically, changes in flow may be detected by evaluating various flow data. For example, by evaluating FV loops, as described above, an increase in resistance may be detected over a number of breaths. That is, upon comparing consecutive FV loops, the expiratory plot for each FV loop may reflect a progressive reduction in expiratory flow (i.e., a smaller FV loop), indicative of increasing resistance.

Pressure Data

According to embodiments, data processing module 222 may be configured to monitor pressure. Pressure may be measured by any appropriate, internal or distributed device or sensor within the ventilatory system 200. For example, pressure may be monitored by proximal electromechanical transducers connected near the airway opening (e.g., on the inspiratory limb, expiratory limb, at the patient interface, etc.). Alternatively, pressure may be monitored distally, at or near the lungs and/or diaphragm of the patient.

For example, $P_{Peak}$ and/or $P_{Plat}$ (estimating $P_a$) may be measured proximally (e.g., at or near the airway opening) via single-point pressure measurements. According to embodiments, $P_{plat}$ (estimating $P_a$) may be measured during an inspiratory pause maneuver (e.g., expiratory and inspiratory valves are closed briefly at the end of inspiration for measuring the $P_{Plat}$ at zero flow). According to other embodiments, circuit pressure may be measured during an expiratory pause maneuver (e.g., expiratory and inspiratory valves are closed briefly at the end of exhalation for measuring EEP at zero flow).

Data processing module 222 may be further configured to plot monitored pressure data graphically via any suitable means. For example, according to embodiments, pressure data may be plotted versus time (pressure waveform), versus volume (pressure-volume loop or PV loop), or versus any other suitable parameter as may be useful to a clinician. According to embodiments, pressure may be plotted such that each breath may be independently identified. Further, pressure may be plotted such that inspiratory pressure and expiratory pressure may be independently identified, e.g., inspiratory pressure may be represented in one color and expiratory pressure may be represented in another color. According to additional embodiments, pressure waveforms and PV loops, for example, may be represented alongside additional graphical representations, e.g., representations of volume, flow, etc., such that a clinician may substantially simultaneously visualize a variety of parameters associated with each breath.

According to embodiments, PV loops may provide useful clinical and diagnostic information to clinicians regarding the respiratory resistance or compliance of a patient. Specifically, upon comparing PV loops from successive breaths, an increase in resistance may be detected when successive PV loops shorten and widen over time. That is, at constant pressure, less volume is delivered to the lungs when resistance is increasing, resulting in a shorter, wider PV loop. According to alternative embodiments, a PV loop may provide a visual representation, in the area between the inspiratory plot of pressure vs. volume and the expiratory plot of pressure vs. volume, which is indicative of respiratory compliance. Further, PV loops may be compared to one another to determine whether compliance has changed. Additionally or alternatively, optimal compliance may be determined. That is, optimal compliance may correspond to the dynamic compliance determined from a PV loop during a recruitment maneuver, for example.

According to additional embodiments, PV curves may be used to compare $C_S$ and $C_D$ over a number of breaths. For example, a first PV curve may be plotted for $C_S$ (based on $P_{Plat}$ less EEP) and a second PV curve may be plotted for $C_D$ (based on $P_{Peak}$ less EEP). Under normal conditions, $C_S$ and $C_D$ curves may be very similar, with the $C_D$ curve mimicking the $C_S$ curve but shifted to the right (i.e., plotted at higher pressure). However, in some cases the $C_D$ curve may flatten out and shift to the right relative to the $C_S$ curve. This graphical representation may illustrate increasing $P_t$, and thus increasing R, which may be due to mucous plugging or bronchospasm, for example. In other cases, both the $C_D$ curve and the $C_S$ curves may flatten out and shift to the right. This graphical representation may illustrate an increase in $P_{Peak}$ and $P_{Plat}$ without an increase in $P_t$, and thus may implicate a decrease in lung compliance, which may be due to tension pneumothorax, atelectasis, pulmonary edema, pneumonia, bronchial intubation, etc.

As may be further appreciated, relationships between resistance, static compliance, dynamic compliance, and various pressure readings may give indications of patient condition. For example, when $C_S$ increases, $C_D$ increases and, similarly, when R increases, $C_D$ increases. Additionally, as discussed previously, $P_t$ represents the difference in pressure attributable to resistive forces over elastic forces. Thus, where $P_{Peak}$ and $P_t$ are increasing with constant $V_T$ delivery, R is increasing (i.e., where $P_{Peak}$ is increasing without a concomitant increase in $P_{Plat}$). Where $P_t$ is roughly constant, but where $P_{Peak}$ and $P_{Plat}$ are increasing with a constant $V_T$ delivery, $C_S$ is increasing.

Volume Data

According to embodiments, data processing module 222 may be configured to derive volume via any suitable means. For example, as described above, during volume ventilation, a prescribed $V_T$ may be set for delivery to the patient. The actual volume delivered may be derived by monitoring the inspiratory flow over time (i.e., V=F*T). Stated differently, integration of flow over time will yield volume. According to embodiments, $V_T$ is completely delivered upon reaching $T_I$. Similarly, the expiratory flow may be monitored such that expired tidal volume ($V_{TE}$) may be derived. That is, under ordinary conditions, upon reaching the $T_E$, the prescribed $V_T$ delivered should be completely exhaled and FRC should be reached. However, under some conditions $T_E$ is inadequate for complete exhalation and FRC is not reached.

Data processing module 222 may be further configured to plot derived volume data graphically via any suitable means. For example, according to embodiments, volume data may be plotted versus time (volume waveform), versus flow (flow-volume loop or FV loop), or versus any other suitable parameter as may be useful to a clinician. According to embodiments, volume may be plotted such that each breath may be independently identified. Further, volume may be plotted such that prescribed $V_T$ and $V_{TE}$ may be independently identified, e.g., prescribed $V_T$ may be represented in one color and $V_{TE}$ may be represented in another color. According to additional embodiments, volume waveforms and FV loops, for example, may be represented alongside additional graphical representations, e.g., representations of pressure, flow, etc., such that a clinician may substantially simultaneously visualize a variety of parameters associated with each breath.

Disconnection of the Patient Ventilator Circuit

According to embodiments, data processing module 222 may be configured to determine if the ventilation tubing system 130 or patient circuit has become disconnected from the patient or the ventilator during ventilation. Data processing module 222 determines that a patient circuit is disconnected by any suitable means. In some embodiments, data processing module 222 determines that the patient circuit is disconnected by evaluating data, such as exhaled pressure and/or exhaled volume. In further embodiments, data processing module 222 determines if the patient circuit is disconnected by determining if a disconnect alarm has been executed. A disconnect alarm is executed when the ventilation tubing system is disconnected from the patient and/or the ventilator. If the disconnect alarm has been executed, then data processing module 222 determines that the patient circuit is disconnected. If the disconnect alarm has not been executed, then data processing module 222 determines that the patient circuit is connected.

Breath Type

According to embodiments, data processing module 222 is configured to identify the breath type. In some embodiments, data processing module 222 is configured to identify the active trigger type utilized by the breath type and/or the background trigger type utilized in the background. Data processing module 222 determines the breath type and/or trigger type by any suitable systems or methods. In some embodiments, data processing module 222 determines the breath type and/or trigger type based on clinician or operator input and/or selection. In further embodiments, data processing module 222 determines the breath type and/or trigger type based on ventilator selection of the breath type and/or trigger type. For example, some breath types include VC, PC, VC+, PS, PA, IE Sync, DEA, TC, and VS.

Asynchrony Detection

A recent study suggests that clinicians are able to detect less than one-third of patient efforts that do not result in the delivery of a breath, or missed breaths.[1] Further, this study has shown that the rate of correct detection decreases as the prevalence of missed breaths increases. Considering that missed breaths may occur in up to 80% of mechanically ventilated patients, systems and methods for better detection of asynchrony are needed. While operating a ventilator, it is desirable to detect, limit, or preferably eliminate, asynchrony.

[1] Colombo, D., Cammarota, G., Alemani, M., Carenzo, L., Barra, F., Vaschetto, R., et al. (2011). Efficacy of ventilator waveforms observation in detecting patient-ventilator asynchrony. *Critical Care Medicine*, p. 3.

Figure 2B:
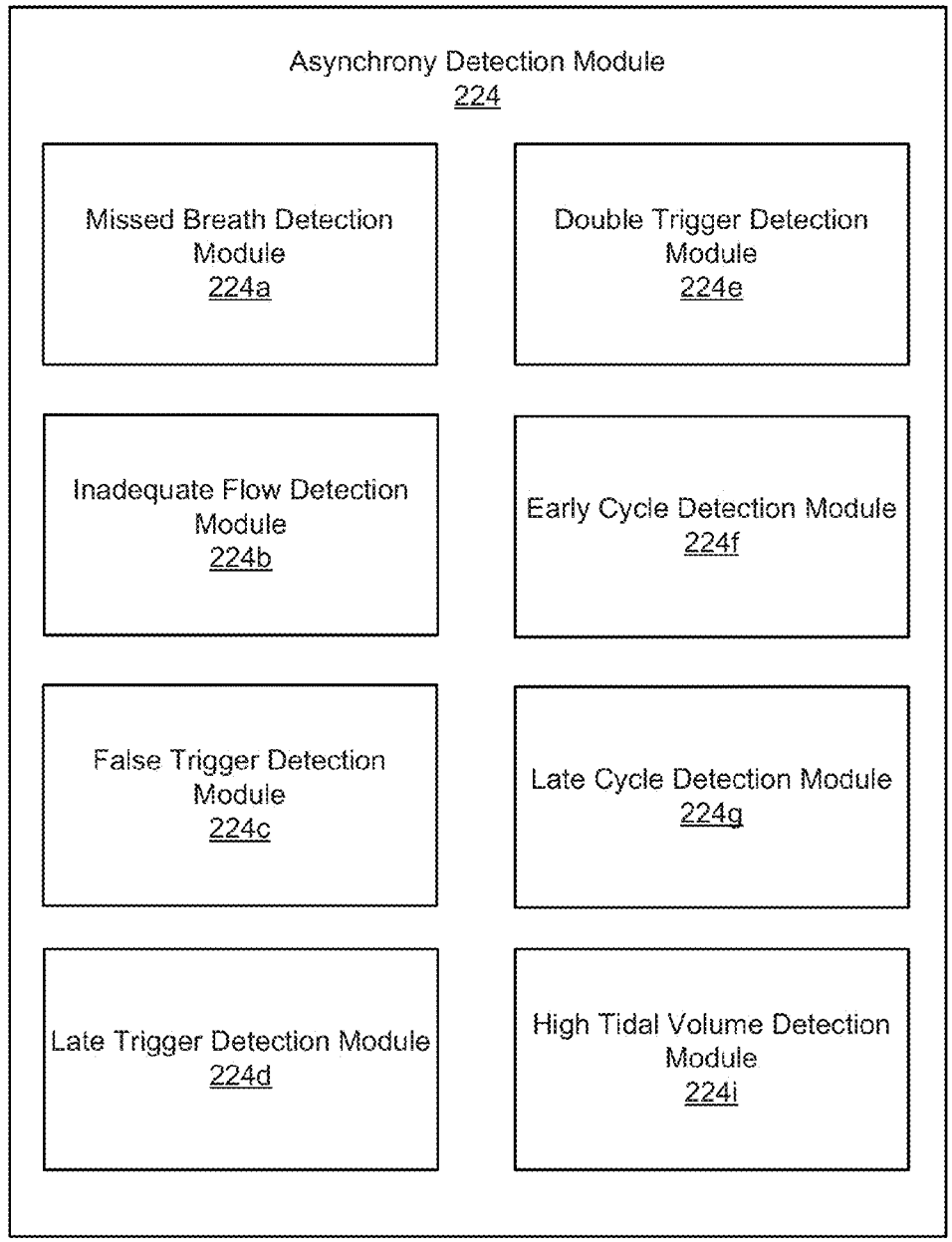
FIG. 2B is a block-diagram illustrating an embodiment of the asynchrony detection module shown in FIG. 2A.

Accordingly, ventilator 202 may further include asynchrony module 224. Asynchrony is detected by the asynchrony module 224 when a missed breath, false trigger, late trigger, early cycle, late cycle, double trigger, inadequate flow, and/or high tidal volume is detected. As illustrated in FIG. 2B, the asynchrony module includes a missed breath detection module 224a, a false trigger detection module 224c, a late trigger detection module 224d, an early cycle detection module 224f, a late cycle detection module 224g, a double trigger detection module 224e, an inadequate flow detection module 224b, and/or a high tidal volume detection module 224i for detecting these various asynchrony conditions. In some embodiments, the detection of one type of asynchrony can cause or lead to the detection of another type of asynchrony. The asynchrony module 224 receives and analyzes data gathered by or data derived from data gathered by internal sensors 220 and/or distributed sensors 218. The asynchrony module 224 utilizes the received data in combination with data regarding detected triggers from an active and/or background trigger type.

Missed Breath Detection

Ventilator 202 may further include a missed breath detection module 224a. A missed breath, as used herein, is a patient inspiratory effort that does not result in the delivery of a breath by the ventilator. A missed breath occurs when the ventilator does not detect a patient inspiratory and/or expiratory effort. The ventilator may not detect the inspiratory and/or expiratory effort because the trigger threshold is set too high and/or because the inspiratory and/or expiratory effort is below the minimum trigger detection level for the active trigger type. Accordingly, missed breaths can lead to patient discomfort, patient fatigue, and/or extended ventilation time.

The type of triggering detection utilized by the ventilator is determined by the selected trigger type. Accordingly, different trigger types will detect patient inspiratory and/or expiratory efforts or triggers/cycles differently. Accordingly, the missed breath detection module 224a determines missed breaths by monitoring for patient inspiratory and/or expiratory efforts or patient triggers/cycles with an active trigger type and with a background trigger type. If a first patient effort detected by the background trigger type correlates to a second patient effort detected by the active trigger type, then the detected patient efforts are considered to have been generated by the same patient effort and a missed breath is not detected. The first patient effort and the second patient effort may correlate if recorded at the same time or within a reasonable and expected time delay, such as 400 milliseconds (ms) or less for a neonate and 1 second or less for an adult. The amount of time varies based on the patient's PBW, the type of ventilator utilized, and the set trigger type. For example, the time varies based on whether an adult, child, neonate, male, or female is being ventilated by the ventilator. Accordingly, the time delay listed above is exemplary only and will vary based on the patient, ventilator, and/or trigger type. As discussed above, any inspiratory patient effort detected by the active trigger type results in the delivery of a breath.

In some embodiments, the missed breath detection module 224a detects a missed breath when a first detected patient effort by the background trigger type does not correlate with a detected patient effort by the active trigger type. As discussed above, the first patient effort and the second patient effort may correlate if recorded at the same time or within a reasonable and expected time delay, such as 400 ms or less for a neonate and 1 second or less for an adult. If the detected inspiratory patient efforts by the background trigger type and the active trigger type do not correlate, then a missed breath is detected. In an embodiment, an equation or mathematical operation is used to determine if the first detected patient effort correlates with the second detected patient effort. In some embodiments, the active trigger type is utilized during a VC, VS, VC+, PS, PC, PA, TC, DEA, or IE Sync breath type. In some embodiments, the active trigger type is a flow monitoring type, a pressure monitoring type, a nasal detection type, an Edi type (or DEA type), and/or a intrapleural pressure type (or IE Synch type). In other embodiments, the background trigger type is a flow monitoring type, a pressure monitoring type, a nasal detection type, an Edi type (or DEA type), and/or a intraplueral pressure type (or IE Sync type).

In further embodiments, the missed breath detection module 224a detects a missed breath when an inspiratory patient effort and an expiratory patient effort are detected by a background trigger type before an inspiratory patient effort is detected by the active trigger type. As discussed above, any inspiratory patient effort detected by the active trigger type results in the delivery of a breath.

In further embodiments, the missed breath detection module 224a determines a missed breath when an expiratory patient effort and patient inspiratory patient effort is detected by a background trigger type before an expiratory patient effort is detected by the active trigger type. As discussed above, any expiratory patient effort detected by the active trigger type results in the delivery of expiration.

In other embodiments, the missed breath detection module 224a determines the number of missed breaths (also known as a missed breath metric) by utilizing at least one counter. During these embodiments, the ventilator updates a counter with a sum of the detected patient inspiratory and/or expiratory efforts by the background trigger type and a sum of the detected patient inspiratory and/or expiratory efforts by the active trigger type. In these embodiments, the counter subtracts any patient inspiratory and/or expiratory efforts determined by the active trigger type and adds any patient efforts determined by the background trigger type in the counter to determine the number of missed breaths. In some embodiments, the number of missed breaths is referred to as a missed breath metric. In another embodiment a mathematical model or algorithm is used to calculate how patient inspiratory and/or expiratory efforts are detected with the background and active trigger type to update at least one counter. In an embodiment, the at least one counter is reset after a predetermined amount of time or breaths, or in response to clinician input.

In another embodiment, at least two counters are used. In an embodiment with at least two counters, the first counter is updated with a sum of the detected patient inspiratory and/or expiratory efforts by the background trigger type and a second counter is updated with a sum of the detected patient inspiratory and/or expiratory efforts by the active trigger types. In embodiments with at least two counters, the missed breath detection module 224a performs an algorithm or mathematical operation, such as subtracting the count of the second counter from the count of the first counter to calculate the number of missed breaths or a missed breaths metric. In some embodiments, the value of a counter represents a missed breath metric and no further algorithm or mathematical operation is needed to calculate the missed breaths metric. The number of missed breaths or the missed breaths metric may be calculated according to any suitable method.

False Trigger Detection

Ventilator 202 may further include a false trigger detection module 224c. A false trigger, as used herein, occurs when the ventilator delivers inspiration prior to the detection of a patient inspiratory effort by a background trigger type. As used herein the term "prior" refers to an event that occurs more than 5 ms before a referenced event. The false trigger may be from some anomalous condition that is interpreted by the ventilator breath type as an inspiratory patient effort. Because of the short expiratory time, the false trigger and early delivered inspiration may come before the patient has the chance to fully exhale and may cause gas-trapping in the lungs. Accordingly, false triggering can lead to patient discomfort and/or an increase in the length of ventilation time.

As discussed above, the type of triggering detection utilized by the ventilator is determined by the selected trigger type. Accordingly, different trigger types will detect patient inspiratory efforts or triggers differently. Therefore, the false trigger detection module 224c determines false triggers by monitoring for patient inspiratory efforts or patient triggers with an active trigger type and with a background trigger type. If a first patient effort detected by the background trigger type is within 60 milliseconds for a neonate and 100 ms for an adult before a second patient effort is detected by the active trigger type, then the detected patient efforts are considered to have been generated by the same patient effort and close enough to each other to be a reasonable time delay so a false trigger is not detected. However, this threshold may vary based on the patient, trigger type, and type of ventilator utilized. Accordingly, in some embodiments, if a first patient effort detected by the background trigger type is within 10 ms, 20 ms, 30 ms, 40 ms, 50 ms, 70 ms, 80 ms, 90 ms, 110 ms, 120 ms, 130 ms, 140 ms, 150 ms, 160 ms, 170 ms, 180 ms, 190 ms, or 200 ms before a second patient effort is detected by the active trigger type, then the detected patient efforts are considered to have been generated by the same patient effort and close enough to each other to be a reasonable time delay so a false trigger is not detected. Alternatively, if a first patient effort detected by the background trigger type is more than 60 milliseconds for a neonate and 100 ms for an adult before the second patient effort is detected by the active trigger type, then the detected patient efforts are considered to have been generated by the same patient effort and far enough away from each other to not be considered a reasonable time delay so a false trigger is detected. In some embodiments, the active trigger type is utilized during a VC, VS, VC+, PS, PC, PA, TC, DEA, or IE Sync breath type. In some embodiments, the active trigger type is a flow monitoring type, a pressure monitoring type, a nasal detection type, an Edi type (or DEA type), and/or a intraplueral pressure type (or IE Synch type). In other embodiments, the background trigger type is a flow monitoring type, a pressure monitoring type, a nasal detection type, an Edi type (or DEA type), and/or a intraplueral pressure type (or IE Sync type).

In other embodiments, the false trigger detection module 224c determines the number of false triggers (also referred to as a false trigger metric) by utilizing at least one counter. During these embodiments, the ventilator updates at least one counter every time a false trigger is detected. In some embodiments, the at least one counter is reset after a predetermined amount of time, after a predetermined number of breaths, or in response to clinician input.

Late Trigger Detection

Ventilator 202 may further include a late trigger detection module 224d. A late trigger, as used herein, occurs when the ventilator delivers inspiration after the detection of a patient inspiratory effort by the background trigger type. As used herein the term "after" refers to an event that occurs more than 5 ms after a referenced event. The late trigger may occur when the trigger threshold is set too high. Therefore, the trigger may not be detected at the initial inspiratory effort and instead is not detected until a continuation of the patient's inspiratory effort reaches above the set threshold. Because of the long expiratory time, the next breaths may come after the patient desires the breath. Accordingly, a late trigger can lead to patient discomfort, patient fatigue, hypercapnia, and/or hypoxemia.

As discussed above, the type of triggering detection utilized by the ventilator is determined by the selected trigger type. Accordingly, different trigger types will detect patient inspiratory efforts or triggers differently. Therefore, the late trigger detection module 224d determines false triggers by monitoring for patient inspiratory efforts or patient triggers with an active trigger type and with a background trigger type. If a first patient effort detected by the background trigger type is within 60 milliseconds for a neonate and 100 ms for an adult after a second patient effort is detected by the active trigger type, then the detected patient efforts are considered to have been generated by the same patient effort and close enough to each other to be a reasonable time delay so a late trigger is not detected. However, this threshold may vary based on the patient, trigger type, and type of ventilator utilized. Accordingly, in some embodiments, if a first patient effort detected by the background trigger type is within 10 ms, 20 ms, 30 ms, 40 ms, or 50 ms, 70 ms, 80 ms, 90 ms, 110 ms, 120 ms, 130 ms, 140 ms, 150 ms, 160 ms, 170 ms, 180 ms, 190 ms, or 200 ms after a second patient effort is detected by the active trigger type, then the detected patient efforts are considered to have been generated by the same patient effort and close enough to each other to be a reasonable time delay so a late trigger is not detected. As discussed above, any inspiratory patient effort detected by the active trigger type results in the delivery of inspiration. However, if a first patient effort detected by the background trigger type is more than 60 milliseconds for a neonate and 100 ms for an adult after the second patient effort is detected by the active trigger type, then the detected patient efforts are considered to have been generated by the same patient effort and far enough from each other to not be a reasonable time delay so a late trigger is detected. In some embodiments, the active trigger type is utilized during a VC, VS, VC+, PS, PC, PA, TC, DEA, or IE Sync breath type. In some embodiments, the active trigger type is a flow monitoring type, a pressure monitoring type, a nasal detection type, an Edi type (or DEA type), and/or a intraplueral pressure type (or IE Synch type). In other embodiments, the background trigger type is a flow monitoring type, a pressure monitoring type, a nasal detection type, an Edi type (or DEA type), and/or a intraplueral pressure type (or IE Sync type).

In other embodiments, the late trigger detection module 224d determines the number of late triggers (also referred to as a late trigger metric) by utilizing at least one counter. During these embodiments, the ventilator updates at least one counter every time a late trigger is detected. In some embodiments, the at least one counter is reset after a predetermined amount of time, after a predetermined number of breaths, or in response to clinician input.

In further embodiments, the late trigger detection module 224a detects a late trigger when an inspiratory patient effort is detected by a background trigger type at least 60 ms for a neonate and 100 ms for an adult before an inspiratory patient effort is detected by the active trigger type and before an expiratory patient effort is detected by the background trigger type. As discussed above, any inspiratory patient effort detected by the active trigger type results in the delivery of a breath.

Early Cycle Detection

Ventilator 202 may further include an early cycle detection module 224f. An early cycle, as used herein, occurs when the ventilator delivers expiration prior to the detection of a patient expiratory effort by the background trigger type. The early cycle may be from some anomalous condition that is interpreted by the ventilator breath type as an expiratory patient effort. Because of the short inspiratory time, the early cycle and early delivered expiration may come before the patient has the chance to fully inhale preventing the patient from receiving the amount of oxygen desired. Accordingly, an early cycle can lead to patient discomfort, patient fatigue, hypercapnia, and/or hypoxemia.

Similar systems and methods as describe above for trigger detection may be utilized for cycle detection. The type of cycling detection utilized by the ventilator is determined by the selected trigger type. Accordingly, different trigger types will detect patient expiratory efforts or cycles differently. Therefore, the early cycle detection module 224f determines early cycles by monitoring for patient expiratory efforts or patient triggers with an active trigger type and with a background trigger type. If a first patient expiratory effort detected by the background trigger type is within 60 milliseconds for a neonate and 100 ms for an adult before a second patient expiratory effort is detected by the active trigger type, then the detected patient efforts are considered to be close enough to each other to be a reasonable time delay so an early cycle is not detected. However, this threshold may vary based on the patient, trigger type, and type of ventilator utilized. Accordingly, in some embodiments, if a first expiratory patient effort detected by the background trigger type is within 10 ms, 20 ms, 30 ms, 40 ms, or 50 ms, 70 ms, 80 ms, 90 ms, 110 ms, 120 ms, 130 ms, 140 ms, 150 ms, 160 ms, 170 ms, 180 ms, 190 ms, or 200 ms before a second expiratory patient effort is detected by the active trigger type, then the detected patient efforts are considered to be close enough to each other to be a reasonable time delay so an early cycle is not detected. As discussed above, any expiratory patient effort detected by the active trigger type results in the delivery of expiration. However, if a first expiratory patient effort detected by the background trigger type is more than 60 milliseconds for a neonate and 100 ms for an adult before the second patient effort is detected by the active trigger type, then the detected patient efforts are considered to have been generated by the same patient effort and an early cycle is detected. In some embodiments, the active trigger type is utilized during a VC, VS, VC+, PS, PC, PA, TC, DEA, or IE Sync breath type. In some embodiments, the active trigger type is a flow monitoring type, a pressure monitoring type, a nasal detection type, an Edi type (or DEA type), and/or a intraplueral pressure type (or IE Synch type). In other embodiments, the background trigger type is a flow monitoring type, a pressure monitoring type, a nasal detection type, an Edi type (or DEA type), and/or a intraplueral pressure type (or IE Sync type).

In other embodiments, the early cycle detection module 224f determines the number of early cycles or an early cycle metric by utilizing at least one counter. During these embodiments, the ventilator updates at least one counter every time an early cycle is detected. In some embodiments, the at least one counter is reset before a predetermined amount of time, before a predetermined number of breaths, or in response to clinician input.

Late Cycle Detection

Ventilator 202 may further include a late cycle detection module 224g. A late cycle, as used herein, occurs when the ventilator delivers expiration after the detection of a patient expiratory effort by a background trigger type. The late cycle may occur when the cycle threshold is set too high. Therefore, the cycle may not be detected at the initial expiratory effort and instead is not detected until a continuation of the patient's expiratory effort reaches above the set threshold. Because of the long inspiratory time or low $E_{SENS}$, the patient may inhale too much gas causing gas-trapping in the lungs. Accordingly, late cycling can lead to patient discomfort.

Similar systems and methods as describe above for trigger detection may be utilized for cycle detection. The type of cycling detection utilized by the ventilator is determined by the selected trigger type. Accordingly, different trigger types will detect patient expiratory efforts or cycles differently. Therefore, the late cycle detection module 224g determines late cycles by monitoring for patient expiratory efforts or patient cycles with an active trigger type and with a background trigger type. If a first patient effort detected by the background trigger type is within 60 milliseconds for a neonate and 100 ms for an adult after a second patient effort is detected by the active trigger type, then the detected patient efforts are considered to have been generated by the same patient effort and to be close enough to each other to be a reasonable time delay so a late cycle is not detected. However, this threshold may vary based on the patient, trigger type, and type of ventilator utilized. Accordingly, in some embodiments, if a first expiratory patient effort detected by the background trigger type is within 10 ms, 20 ms, 30 ms, 40 ms, or 50 ms, 70 ms, 80 ms, 90 ms, 110 ms, 120 ms, 130 ms, 140 ms, 150 ms, 160 ms, 170 ms, 180 ms, 190 ms, or 200 ms after a second expiratory patient effort is detected by the active trigger type, then the detected patient efforts are considered to have been generated by the same patient effort and considered to be close enough to each other to be a reasonable time delay so a late cycle is not detected. As discussed above, any expiratory patient effort detected by the active trigger type results in the delivery of expiration. However, if a first patient effort detected by the background trigger type is more than 60 milliseconds for a neonate and 100 ms for an adult after the second patient effort is detected by the active trigger type, then the detected patient efforts are considered to have been generated by the same patient effort and to be far enough from each other to not be a reasonable time delay so a late cycle is detected. In some embodiments, the active trigger type is utilized during a VC, VS, VC+, PS, PC, PA, TC, DEA, or IE Sync breath type. In some embodiments, the active trigger type is a flow monitoring type, a pressure monitoring type, a nasal detection type, an Edi type (or DEA type), and/or a intraplueral pressure type (or IE Synch type). In other embodiments, the background trigger type is a flow monitoring type, a pressure monitoring type, a nasal detection type, an Edi type (or DEA type), and/or a intraplueral pressure type (or IE Sync type).

In further embodiments, the late cycle detection module 224g determines a late cycle when an expiratory patient effort is detected by a background trigger type at least 60 ms for a neonate and 100 ms for an adult before an expiratory patient effort is detected by the active trigger type and before an inspiratory patient effort is detected by the background trigger type. As discussed above, any expiratory patient effort detected by the active trigger type results in the delivery of expiration.

In other embodiments, the late cycle detection module 224g determines the number of late cycles or a late cycle metric by utilizing at least one counter. During these embodiments, the ventilator updates at least one counter every time a late cycle is detected. In some embodiments, the at least one counter is reset after a predetermined amount of time, after a predetermined number of breaths, or in response to clinician input.

In other embodiments, the late cycle detection module 224g determines a late cycles or a long inspiration time. In embodiments, the late cycle detection module 224g detects a late cycle when the long inspiratory time is longer than a predetermined threshold, which is based on a patient's body weight or predicted body weight. For example, a normal inspiratory time for most adults is about 800 ms to 1000 ms. However, the appropriate inspiration time varies for neonates, children, because their respiratory rates are considerably different from most normal adults. Accordingly, the predetermined threshold varies based on the predicted body weight (or age) of the patient. For example, during ventilation of a neonate, the predetermined long inspiratory time threshold is 500 ms. In some embodiments, during ventilation of a child, the predetermined long inspiratory time threshold is 750 ms. In some embodiments, the late cycle detection module 224g detects a late cycle when the inspiratory time is 1000 ms or higher. In other embodiments, the late cycle detection module 224g detects a late cycle when the inspiratory time is 500 ms or higher. In further embodiments, the late cycle detection module 224g detects a late cycle when the inspiratory time is at 750 ms or higher. In additional embodiments, the late cycle detection module 224g detects a late cycle when the inspiratory time is 850 ms or higher. In some embodiments, the late cycle detection module 224g detects a late cycle when the inspiratory time is 900 ms or higher. In other embodiments, the late cycle detection module 224g detects a late cycle when the inspiratory time is 400 ms or higher. In other embodiments, the late cycle detection module 224g detects a late cycle when the inspiratory time is 700 ms or higher.

The thresholds listed above are just one example list of possible conditions that could be used to indicate a long inspiration time and therefore a late cycle. Any suitable list of conditions for determining the occurrence of a long inspiration time and late cycle may be utilized.

Double Trigger Detection

Double triggering is a term that refers to a set of instances in which a ventilator delivers two breaths in response to what is, in fact, a single patient effort. A double trigger occurs when the ventilator delivers two or more ventilator cycles separated by a very short expiratory time, with at least one breath being triggered by the patient. Typically, the first cycle is patient triggered and the second breath is triggered by either a continuation of the patient's inspiratory effort or from some anomalous condition that is interpreted by the ventilator as a second patient effort. Because of the short expiratory time, the additional breaths may come before the patient has the chance to fully exhale and may cause gas-trapping in the lungs. Accordingly, double triggering can lead to patient discomfort and/or an increase in the length of ventilation time.

According to some embodiments, double trigger detection module 224e may detect double triggering when a double trigger has occurred at least three times within the last 60 seconds. According to further embodiments, double trigger detection module 224e may detect double triggering when more than 30% of the patient-initiated mandatory breaths have a double trigger within the last 180 seconds. According to additional embodiments, double trigger detection module 224e may detect double triggering when more than 10% of the patient-initiated mandatory breaths have a double trigger within the last 60 seconds. The double trigger detection module 224e may begin the evaluation at the beginning of each patient-initiated breath.

In some embodiments, double trigger detection module 224e detects a double trigger when one or more of the following conditions are met:
1. expiratory time for a patient-initiated mandatory breath is less than 240 milliseconds (ms);
2. the exhaled tidal volume associated with the expiratory period is less than 10% of the delivered tidal volume of the prior inspiratory period;
3. no disconnect alarm is detected.

In further embodiments, condition number 1, listed above, may refer to any suitable expiratory time threshold. For example, in an alternative embodiment the expiratory time threshold is an expiratory time of less than 230 ms, 220 ms, 210 ms, 200 ms, or 190 ms depending upon the type of ventilator, patient, breath type, ventilator parameters, ventilator settings, and/or ventilator modes, etc. Condition number 3 listed above, is considered a "threshold" in the present disclosure and in the listed claims. Further, the detection of any yes/no "condition" is considered a "threshold" in the present disclosure and in the listed claims. In an embodiment of the double triggering detection system, all three of the above conditions must be present for the double trigger detection module 224e to detect a double trigger.

In some embodiments, conditions 1 and 2 are detected by the ventilator based on the triggering of an active trigger type. In other embodiments, conditions 1 and 2 are detected by the ventilator based on the triggering of a background trigger type. In alternative embodiments, conditions 1 and 2 are detected by the ventilator based on the triggering of either an active trigger type or a background trigger type.

The three thresholds listed above are just one example list of possible conditions that could be used to indicate double triggering. Any suitable list of conditions for determining the occurrence of double triggering may be utilized. For example, other suitable conditions/thresholds that may be utilized to determine that double triggering is implicated include a determination that the patient circuit has not become disconnected, an analysis of pressure during exhalation, a comparison of the estimated patient's neural inspiratory time to inspiratory time delivered by the ventilator, an analysis of end tidal carbon dioxide ($ETCO_2$), an analysis of volumetric carbon dioxide ($VCO_2$), a determination that the expired volume is less than 50% of the delivered volume, a determination that monitored PEEP is a negative number for one second or less during the inspiratory effort, and an analysis of a ratio of inspiratory to expiratory time (I:E ratio).

Inadequate Flow Detection

Ventilator 202 may further include an inadequate flow detection module 224b. Inadequate flow is detected when a patient is receiving less flow than desired by the patient during ventilation. Inadequate flow occurs when a flow rate is set too low, a peak flow rate is set too low, and/or the flow pattern does not match that of the patient's effort. Accordingly, inadequate flow can lead to patient discomfort, patient fatigue, hypercapnia, and/or hypoxemia.

According to embodiments, inadequate flow occurs as a result of various patient conditions and/or inappropriate ventilator settings. Thus, according to embodiments, inadequate flow detection module 224b evaluates various ventilatory parameter data and ventilatory settings based on one or more predetermined thresholds to detect the presence of inadequate flow. For example, inadequate flow detection module 224b may evaluate circuit pressure, mean airway pressure, etc., and may compare the evaluated parameters to one or more predetermined thresholds. In order to prevent unnecessary alarms, prompts, notifications, and/or recommendations, thresholds and conditions are utilized by the inadequate flow detection module 224b to determine when inadequate flow has occurred with sufficient frequency to warrant notification of the operator. For example, in some embodiments, an inadequate flow that occurs in one breath in isolation from any other breaths with an inadequate flow will not be considered enough to warrant an occurrence of inadequate flow by the inadequate flow detection module 224b. As used herein any threshold, condition, setting, parameter, and/or frequency that are "predetermined" may be input or selected by the operator and/or may be set or selected by the ventilator.

In embodiments, the inadequate flow detection module 224b detects an inadequate flow when one or more predetermined thresholds are breached at a predetermined frequency. In some embodiments, the inadequate flow detection module 224b detects an inadequate flow when one or more predetermined thresholds are breached at least three times within a predetermined amount of time. In alternative embodiments, the inadequate flow detection module 224b detects an inadequate flow when one or more predetermined thresholds are breached by more than 30% of the PIM breaths within a predetermined amount of time. In some embodiments, the inadequate flow detection module 224b detects an inadequate flow when one or more predetermined thresholds are breached in more than 10% of the PIM breaths within a predetermined amount of time. The predetermined amount of time may be any suitable range of time for determining if an inadequate flow has occurred, such as a time ranging from 30 seconds to 240 seconds. The frequency thresholds disclosed above are exemplary and do not limit the disclosure. Any suitable frequency threshold for determining that the patient is receiving an inadequate flow during ventilation may be utilized.

According to some embodiments, inadequate flow detection module 224b detects an inadequate flow when a mean airway pressure for a PIM breath is below the set PEEP. In some embodiments, the mean airway pressure is compared to a predetermined pressure. For example, the predetermined pressure may be PEEP plus 1 cm $H_2O$, or PEEP minus 2 cm $H_2O$. The "mean airway pressure" referred to herein for a PIM breath is calculated between the beginning of inspiration and a point where a predetermined amount of tidal volume (e.g., 30%) has been delivered or a predetermined proportion of the inspiration time has expired in the PIM breath. According to embodiments, inadequate flow detection module 224b detects an inadequate flow when more than three PIM breaths within the previous 60 seconds exhibit a mean airway pressure for a PIM breath below the set PEEP and the expiratory time is greater than a predetermined amount of time. According to further embodiments, inadequate flow detection module 224b detects an inadequate flow when more than 30% of the PIM breaths within the previous 180 seconds exhibit a mean airway pressure for a PIM breath below the set PEEP and the expiratory time is greater than a predetermined amount of time. In one embodiment, the inadequate flow detection module 224b begins the evaluation at the end of exhalation for each PIM breath.

In some embodiments, inadequate flow detection module 224b detects an inadequate flow when one or more of the following conditions are met for PIM breath:
1. the amount of pressure delivered when a predetermined amount of tidal volume has been delivered or a predetermined proportion of an inspiration time has expired in the PIM breath is less than the set PEEP; and
2. the amount of mean airway pressure for the PIM breath is less than the set PEEP.

Upon detecting one or more of the above conditions, the inadequate flow detection module 224b may also ensure that at least one of the following two conditions is met:
3. expiratory time for a PIM breath is greater than a predetermined amount of time;
4. the ventilation tubing system status is connected; and
5. no disconnect alarm is detected.

The confirmation conditions (3, 4, and 5) listed above confirm that the above pressure conditions (1 and 2) are the result of an inadequate flow, instead of another underlying condition. For example, if a disconnect alarm or the tubing status is disconnected, then the above pressure conditions (1 and 2) are the result of a disconnected patient circuit and not the result of an inadequate flow. Accordingly, the ventilator will not issue a prompt for inadequate flow if these conditions are not met. In an alternative example, if the expiratory time is less than a predetermined amount, then the above pressure conditions (1 and 2) are most likely the result of double triggering. Accordingly, the ventilator will not issue a prompt for inadequate flow, since the pressure condition was not caused by inadequate flow.

In further embodiments, condition number 3, listed above, refers to any suitable expiratory time threshold. For example, in an alternative embodiment the expiratory time threshold is an expiratory time of greater than 190 ms, 200 ms, 210 ms, 220 ms, 230 ms, or 250 ms depending upon the type of ventilator, patient, breath type, ventilator parameters, ventilator settings, and/or ventilator modes, etc. In further embodiments, the predetermined tidal volume, listed above, refers to any suitable amount of tidal volume during a PIM breath for measuring pressure during ventilation to determine inadequate flow during ventilation, such as 10%, 20%, 30%, 40% and 50%. In some embodiments, the predetermined proportion of the inspiration listed above, refers to any suitable proportion of the inspiration time during a PIM breath for measuring pressure during ventilation to determine inadequate flow during ventilation, such as 10%, 20%, 30%, 40% and 50% of the total amount of inspiration time. The ventilation tubing system status is: (1) connected when the ventilation tubing system is connected to the patient and the ventilator; and (2) disconnected when the ventilation tubing system is not connected to the patient and/or the ventilator. Condition number 4 and condition number 5 listed above, are considered a "threshold" in the present disclosure and in the listed claims. Further, the detection of any yes/no "condition" is considered a "threshold" in the present disclosure and in the listed claims.

In some embodiments, conditions 1, 2, and 3 are detected by the ventilator based on the triggering of an active trigger type. In other embodiments, conditions 1, 2, and 3 are detected by the ventilator based on the triggering of a background trigger type. In alternative embodiments, conditions 1, 2, and 3 are detected by the ventilator based on the triggering of either an active trigger type or a background trigger type.

The thresholds listed above are just one example list of possible conditions that could be used to indicate an inadequate flow. Any suitable list of conditions for determining the occurrence of an inadequate flow may be utilized. For example, other suitable conditions/thresholds that may be utilized to determine that an inadequate flow is implicated include a comparison of the patient flow (i.e., the flow at the connection to the patient) with the flow delivered by the ventilator and a comparison of the pressure to a predetermined acceptable profile.

In other embodiments, the inadequate flow detection module 224b detects inadequate flow when there is a mismatch flow. A mismatch flow occurs when a patient during a volume control ventilation attempts to pull more flow than provided by the fixed flow rate during inspiration and changes the delivered flow rate. The inadequate flow detection module 224b detects a mismatch flow when one or more predetermined thresholds are breached at a predetermined frequency as discussed above. According to some embodiments, inadequate flow detection module 224b detects a mismatch flow when a derivative of the pressure-time curve changes from a positive slope to a negative slope at a predetermined frequency. In some embodiments, inadequate flow detection module 224b detects a mismatch flow when the derivative of the pressure-time curve for the pressure-time curve rises at a rate above a predetermined threshold at the predetermined frequency. For example, the inadequate flow detection module 224b detects a mismatch flow when the pressure-time curve rises at a rate of at least 10 mum at the predetermined frequency. In some embodiments, the derivative of the pressure-time curve for the pressure-time curve rises at a rate of at least 50 ml/m at the predetermined frequency. In further embodiments, the derivative of the pressure-time curve for the pressure-time curve rises at a rate of at least 100 ml/m at the predetermined frequency.

In alternative embodiments, an inadequate flow is detected by detecting a change in a derivative of $P_m$ exceeding a predetermined threshold at a predetermined frequency by a ventilator utilizing an active and/or a background trigger type, such as IE Sync. In some embodiments, the predetermined threshold is change of at least 30%. In alternative embodiments, an inadequate flow is detected by detecting an increase in Edi exceeding a predetermined threshold at a predetermined frequency by a background trigger type, such as the DEA trigger type. In some embodiments, the predetermined threshold is an increase of Edi of at least 15-20 microvolts. In some embodiments, both the IE Sync and the DEA trigger types are running in background to determine a flow mismatch.

According to embodiments, inadequate flow detection module 224b detects a flow mismatch when more than three PIM breaths within the previous 60 seconds exhibit a change from a positive slope to a negative slope in the derivative of the pressure-time curve, a rise in the derivative of the pressure-time curve that is above a predetermine threshold, a change in a derivative of $P_m$ exceeding a predetermined threshold, and/or an increase in Edi exceeding a predetermined threshold. According to further embodiments, inadequate flow detection module 224b detects a flow mismatch when more than 30% of the PIM breaths within the previous 180 seconds exhibit a change from a positive slope to a negative slope in the derivative of the pressure-time curve, a rise in the derivative of the pressure-time curve that is above a predetermine threshold, a change in a derivative of $P_m$ exceeding a predetermined threshold and/or an increase in Edi exceeding a predetermined threshold. In one embodiment, the inadequate flow detection module 224b begins the evaluation at the end of exhalation for each PIM breath.

The thresholds listed above are just one example list of possible conditions that could be used to indicate a flow mismatch, which causes an inadequate flow. Any suitable list of conditions for determining the occurrence of a flow mismatch may be utilized. For example, other suitable conditions/thresholds that may be utilized to determine that a flow mismatch is implicated include a comparison of the patient flow (i.e., the flow at the connection to the patient) with the flow delivered by the ventilator and a comparison of the flow to a predetermined acceptable profile.

High Tidal Volume

Ventilator 202 may further include a high tidal volume detection module 224i. High tidal volume is caused by an inappropriate tidal volume setting, by an inappropriate inspiratory pressure setting, and by missed breaths and/or late triggers. Accordingly, a high tidal volume occurs when a tidal volume is set too high, an inspiratory time is set too long, and/or when the double triggers occur. Accordingly, a high tidal volume can lead to patient discomfort, hyperinflation, and/or barotrauma. However, a high tidal volume may occur as a result of various patient conditions and/or inappropriate ventilator settings. Thus, according to embodiments, the high tidal volume detection module 224i evaluates various ventilatory parameter data and ventilatory settings based on the detected patient efforts of an active and/or background trigger type and compares them to on one or more predetermined thresholds to detect the presence of a high tidal volume.

In embodiments, the high tidal volume detection module 224i detects a high tidal volume when the tidal volume is above a predetermined threshold, which is based on a patient's body weight or predicted body weight. For example, a normal tidal volume for most adults is about 4 to 5 ml per kg. However, the appropriate tidal volume varies for neonates, children, and obese individuals because their weight is considerably different from most normal adults. Accordingly, the predetermined threshold varies based on the weight of the patient. For example, during ventilation of a neonate, the predetermined tidal volume threshold is 0.50 ml per kg or higher. In some embodiments, during ventilation of a child, the predetermine tidal volume threshold is 1 ml per kg or higher. In some embodiments, the high tidal volume detection module 224i detects a high tidal volume when the tidal volume is at 6 ml per kg or higher. In other embodiments, the high tidal volume detection module 224i detects a high tidal volume when the tidal volume is at 7 ml per kg or higher. In further embodiments, the high tidal volume detection module 224i detects a high tidal volume when the tidal volume is at 8 ml per kg or higher. In additional embodiments, the high tidal volume detection module 224i detects a high tidal volume when the tidal volume is at 9 ml per kg or higher. In some embodiments, the high tidal volume detection module 224i detects a high tidal volume when the tidal volume is at 10 ml per kg or higher. In other embodiments, the high tidal volume detection module 224i detects a high tidal volume when the tidal volume is at 11 ml per kg or higher. In other embodiments, the high tidal volume detection module 224i detects a high tidal volume when the tidal volume is at 12 ml per kg or higher. In some embodiments, a tidal volume of 12 ml per kg or higher occurs from stacked breaths based on double triggers.

The thresholds listed above are just one example list of possible conditions that could be used to indicate a high tidal volume. Any suitable list of conditions for determining the occurrence of a high tidal volume may be utilized.

Smart-Prompt Generation

Ventilator 202 may further include a prompt such as a smart prompt module 226. As may be appreciated, multiple ventilatory parameters may be monitored and evaluated in order to detect an implication of asynchrony. In addition, when asynchrony is implicated, many clinicians may not be aware of adjustments to ventilatory parameters that may reduce or eliminate asynchrony. As such, upon detection of asynchrony, the smart prompt module 226 may be configured to notify the clinician that asynchrony is implicated and/or to provide recommendations to the clinician for mitigating asynchrony. For example, smart prompt module 226 may be configured to notify the clinician by displaying a smart prompt on display module 204 and/or within a window of the GUI. According to additional embodiments, the smart prompt is communicated to and/or displayed on a remote monitoring system communicatively coupled to ventilatory system 200. According to alternative embodiments, the smart prompt is any audio and/or visual notification. Alternatively, in an automated embodiment, the smart prompt module 226 communicates with a ventilator control system so that the recommendation may be automatically implemented to mitigate asynchrony.

In order to accomplish the various aspects of the notification and/or recommendation message display, the smart prompt module 226 may communicate with various other components and/or modules. For instance, smart prompt module 226 may be in communication with data processing module 222, asynchrony detection module 224, or any other suitable module or component of the ventilatory system 200. That is, smart prompt module 226 may receive an indication that asynchrony has been implicated by any suitable means. In addition, smart prompt module 226 may receive information regarding one or more parameters that implicated the presence of asynchrony and information regarding the patient's ventilatory settings and treatment. Further, according to some embodiments, the smart prompt module 226 may have access to a patient's diagnostic information (e.g., regarding whether the patient has ARDS, COPD, asthma, emphysema, or any other disease, disorder, or condition).

Smart prompt module 226 may further comprise additional modules for making notifications and/or recommendations to a clinician regarding the presence of asynchrony. For example, according to embodiments, smart prompt module 226 includes a notification module 228 and a recommendation module 230. For instance, smart prompts may be provided according to a hierarchical structure such that a notification message and/or a recommendation message may be initially presented in summarized form and, upon clinician selection, an additional detailed notification and/or recommendation message may be displayed. According to alternative embodiments, a notification message is initially presented and, upon clinician selection, a recommendation message may be displayed. Alternatively or additionally, the notification message may be simultaneously displayed with the recommendation message in any suitable format or configuration.

Specifically, according to embodiments, the notification message alerts the clinician as to the detection of a patient condition, a change in patient condition, or an effectiveness of ventilatory treatment. For example, the notification message may alert the clinician that asynchrony has been detected and the type of asynchrony detected. The type of asynchrony detected may include a missed breath, an early cycle, a flow mismatch, a late cycle, an false trigger, an inadequate flow, a late trigger, a high tidal volume, a double trigger, and a long inspiratory time. The notification message may further alert the clinician regarding the particular ventilatory parameter(s) that implicated asynchrony (e.g., low trigger sensitivity resulted in a missed breath, etc.)

Additionally, according to embodiments, the recommendation message provides various suggestions to the clinician for addressing a detected condition. That is, if asynchrony has been detected, the recommendation message may suggest that the clinician consider changing to a different breath type, such as IE Synch or DEA. According to additional embodiments, the recommendation message may be based on the particular ventilatory parameter(s) (e.g., expiratory sensitivity, electrical activity of the diaphragm, tidal volume, etc.) that implicated asynchrony. Additionally or alternatively, the recommendation message may be based on current ventilatory settings (e.g., breath type) such that suggestions are directed to a particular patient's treatment. Additionally or alternatively, the recommendation message may be based on a diagnosis and/or other patient attributes. Further still, the recommendation message may include a primary recommendation message and a secondary recommendation message.

As described above, smart prompt module 226 may also be configured with notification module 228 and recommendation module 230. The notification module 228 may be in communication with data processing module 222, asynchrony detection module 224, or any other suitable module to receive an indication that asynchrony has been detected. Notification module 228 may be responsible for generating a notification message via any suitable means. For example, the notification message may be provided as a tab, banner, dialog box, or other similar type of display. Further, the notification messages may be provided along a border of the graphical user interface, near an alarm display or bar, or in any other suitable location. A shape and size of the notification message may further be optimized for easy viewing with minimal interference to other ventilatory displays. The notification message may be further configured with a combination of icons and text such that the clinician may readily identify the message as a notification message.

The recommendation module 230 may be responsible for generating one or more recommendation messages via any suitable means. The one or more recommendation messages may provide suggestions and information regarding addressing a detected condition and may be accessible from the notification message. For example, the one or more recommendation messages may identify the parameters that implicated the detected condition, may provide suggestions for adjusting one or more ventilatory parameters to address the detected condition, may provide suggestions for checking ventilatory equipment or patient position, or may provide other helpful information. Specifically, the one or more recommendation messages may provide suggestions and information regarding asynchrony.

According to embodiments, based on the particular parameters that implicated asynchrony, the recommendation module 230 provides suggestions for addressing asynchrony. In some embodiments, the recommendation module 230 provides suggestions for addressing asynchrony based on the type of asynchrony detected. That is, if asynchrony is implicated, the one or more recommendation messages may include suggestions or recommendations for the following:

switching to different breath type, such as PA, PS, IE Sync, DEA, TC, VC, VS, and etc.;
    increasing or decreasing trigger sensitivity;
    increasing or decreasing expiratory sensitivity;
    changing the wave form or flow pattern;
    changing tidal volume;
    changing flow rate;
    changing rise time;
    changing inspiration time;
    changing the inspiration pressure; and
    any other suitable suggestion or recommendation.

According to still other embodiments, the recommendation message includes a primary message and a secondary message. That is, a primary message may provide notification of the condition detected and/or suggestions that are specifically targeted to the detected condition based on the particular parameters that implicated the condition. Alternatively, the primary message may provide suggestions that may provide a higher likelihood of mitigating the detected condition. The secondary message may provide more general suggestions and/or information that may aid the clinician in further addressing and/or mitigating the detected condition. For example, the primary message may provide a specific suggestion for adjusting a particular parameter to mitigate the detected condition (e.g., consider increasing trigger sensitivity). Alternatively, the secondary message may provide general suggestions for addressing the detected condition.

Additionally or alternatively, the one or more recommendation messages may also be based on a secondary condition or current ventilator settings for the patient and/or the type of asynchrony detected. For example, if asynchrony was implicated during a VC breath type by detecting a missed breath, where the patient's current ventilator settings includes auto PEEP (also known as intrinsic PEEP or PEEPi), then the one or more recommendation messages may suggest that the clinician increase the set PEEP level. Further in this example, a secondary recommendation message may suggest if the tidal volume is high, decreasing the respiration rate or lowering the pressure/tidal volume instead of changing the set PEEP level.

The detection of a missed breath, false trigger, late trigger, early cycle, or late cycle in addition to auto PEEP as described above informs the ventilator that the active breath type is not responding correctly to patient efforts because of an improper PEEPi. Accordingly, in some embodiments, this information is utilized in a notification message and/or recommendation message to the clinician (e.g., increase $T_I$ by decreasing $E_{SENS}$). In an alternative embodiment, the ventilator automatically adjusts the $T_I$ based on the detected missed breath, false trigger, late trigger, early cycle, or late cycle and breach of PEEPi.

TABLE 1

Recommendation messages based on breath type, secondary conditions, detection method, and/or type of asynchrony detected.

| Breath Type | Detection Method | Type of Asynchrony | Secondary Condition and/or Ventilator Settings | Notification Message | Primary Recommendation Message | Secondary Recommendation Message |
|---|---|---|---|---|---|---|
| VC | Monitoring airway pressure (pressure signal derivative) | Inadequate Flow | Descending ramp flow pattern | Asynchrony detected (inadequate flow detected) | Consider increasing the flow rate and/or changing the flow pattern to square | Consider changing to a pressure targeted breath type such as PA, PS, or PC. |
| VC | Monitoring airway pressure (pressure signal derivative) | Inadequate Flow | Flow pattern set to square | Asynchrony detected (inadequate flow detected) | Consider increasing the flow rate | Consider changing to a pressure targeted breath type such as PA, PS, or PC. |
| VC | IE Sync monitoring as a background trigger type | Missed Breath | No Auto PEEP and inspiration time in normal range based on PBW | Asynchrony (missed breaths detected) | Consider increasing trigger sensitivity | OR, consider changing trigger type |
| VC | IE Sync monitoring as a background trigger type | Missed Breath | Auto PEEP and/or long inspiration time | Asynchrony (missed breaths detected) | Consider decreasing inspiratory time | N/A |
| VC | IE Sync monitoring as a background trigger type | Missed Breath | Auto PEEP | Asynchrony (missed breaths detected) | Consider increasing PEEP | OR consider decreasing respiration rate and/or tidal volume |
| VC | IE Sync monitoring as a background trigger type | Late Trigger | No Auto PEEP and inspiration time in normal range based on PBW | Asynchrony detected (late trigger detected) | Consider increasing trigger sensitivity | OR, consider changing trigger type |
| VC | IE Sync monitoring as a background trigger type | Late Trigger | Auto PEEP and long inspiration time | Asynchrony detected (late trigger detected) | Consider shortening inspiratory time | OR consider decreasing tidal volume |
| VC | IE Sync monitoring as a background trigger type | Late Trigger | Auto PEEP | Asynchrony detected (late trigger detected) | Consider increasing PEEP | OR consider decreasing respiration and/or tidal volume |
| VC | IE Sync monitoring as a background trigger type | False trigger | N/A | Asynchrony detected (false trigger detected) | Consider decreasing trigger sensitivity | OR, consider changing trigger type |
| VC | IE Sync monitoring as a background trigger type and leak compensation monitoring | False trigger | Leak present | Asynchrony detected (false trigger detected) | Consider enabling leak compensation | N/A |
| VC | IE Sync monitoring as a background trigger type and exhalation time monitoring | Double Trigger | Tidal volume is less than 6 mL/kg and exhalation time is normal | Asynchrony detected (double trigger detected) | Consider increasing tidal volume to 7 mL/kg or 8 mL/kg | N/A |
| VC | IE Sync monitoring as a background trigger type, exhalation time monitoring, | Double Trigger | No inadequate flow detected and inspiration time in | Asynchrony detected (double trigger detected) | Consider decreasing flow rate | OR, consider changing to a spontaneous breath type |

TABLE 1-continued

Recommendation messages based on breath type, secondary conditions, detection method, and/or type of asynchrony detected.

| Breath Type | Detection Method | Type of Asynchrony | Secondary Condition and/or Ventilator Settings | Notification Message | Primary Recommendation Message | Secondary Recommendation Message |
|---|---|---|---|---|---|---|
| | and respiratory rate monitoring | | normal range based on PBW and respiration rate | | | |
| VC | IE Sync monitoring as a background trigger type | Long Inspiration Time | Descending ramp flow patter | Asynchrony detected (long inspiration time detected) | Consider increasing flow rate | OR, consider changing the flow pattern to square |
| VC | IE Sync monitoring as a background trigger type | Long Inspiration Time | Square flow pattern | Asynchrony detected (long inspiration time detected) | Consider increasing flow rate | N/A |
| PS | IE Sync monitoring as a background trigger type and Leak compensation monitoring | Late Cycle | Leak present | Asynchrony (late cycle detected) | Consider enabling leak compensation | OR, consider increasing expiration sensitivity |
| PS | IE Sync monitoring as a background trigger type and/or inspiration time as a function of PBW monitoring | Early Cycle | N/A | Asynchrony (early cycle detected) | Consider increasing expiration sensitivity | N/A |
| PS | Monitoring airway pressure (pressure signal derivative) | Inadequate Flow | Low rise time setting | Asynchrony detected (inadequate flow detected) | Consider increasing rise time | N/A |
| PS | IE Sync monitoring as a background trigger type | Missed Breath | Auto PEEP and long inspiration time | Asynchrony (missed breaths detected) | Consider increasing expiration sensitivity | N/A |
| PS | IE Sync monitoring as a background trigger type | Missed Breath | N/A | Asynchrony (missed breaths detected) | Consider decreasing trigger sensitivity | N/A |
| PS | IE Sync monitoring as a background trigger type | Missed Breath | High tidal volume for PBW | Asynchrony (missed breaths detected) | Consider decreasing the pressure support setting | N/A |
| PS | IE Sync monitoring as a background trigger type | Double Trigger | High expiration sensitivity | Asynchrony detected (double trigger detected) | Consider decreasing expiration sensitivity | N/A |
| PS | Monitoring inspiration time as a function of PBW, exhalation time, and exhalation tidal volume, | Double Trigger | High expiration sensitivity and short exhalation time | Asynchrony detected (double trigger detected) | Consider decreasing expiration sensitivity | N/A |
| PC | IE Sync monitoring as a background trigger type | Late Cycle | N/A | Asynchrony (late cycle detected) | Consider decreasing inspiration time | OR, consider switching to a spontaneous breath type |

TABLE 1-continued

Recommendation messages based on breath type, secondary conditions, detection method, and/or type of asynchrony detected.

| Breath Type | Detection Method | Type of Asynchrony | Secondary Condition and/or Ventilator Settings | Notification Message | Primary Recommendation Message | Secondary Recommendation Message |
|---|---|---|---|---|---|---|
| PC | IE Sync monitoring as a background trigger type | Early Cycle | N/A | Asynchrony (early cycle detected) | Consider increasing inspiration time | OR, consider switching to a spontaneous breath type |
| PC | Monitoring airway pressure (pressure signal derivative) | Inadequate Flow | Low rise time setting | Asynchrony detected (inadequate flow detected) | Consider increasing rise time | N/A |
| PC | IE Sync monitoring as a background trigger type | Missed Breath | No Auto PEEP and inspiration time is in normal range based PBW | Asynchrony (missed breaths detected) | Consider increasing trigger sensitivity | OR, consider changing the trigger type |
| PC | IE Sync monitoring as a background trigger type | Missed Breath | Tidal Volume too large for PBW | Asynchrony (missed breaths detected) | Consider decreasing inspiration pressure | N/A |
| PC | IE Sync monitoring as a background trigger type, inspiration time monitoring, and respiration rate monitoring | Missed Breath | Auto PEEP, respiration rate, and inspiration time too long for PBW | Asynchrony (missed breaths detected) | Consider decreasing inspiration time | N/A |
| PC | IE Sync monitoring as a background trigger type | Missed Breath | Auto PEEP | Asynchrony (missed breaths detected) | Consider increasing PEEP | OR consider decreasing respiration rate if exhalation volume is high or consider decreasing inspiration time |
| PC | IE Sync monitoring as a background trigger type and respiration rate monitoring | Double Trigger | Inspiration time is too short for PBW | Asynchrony detected (double trigger detected) | Consider increasing inspiration time | N/A |
| TC | IE Sync monitoring as a background trigger type | Late Cycle | N/A | Asynchrony (late cycle detected) | Consider increasing expiration sensitivity | N/A |
| TC | IE Sync monitoring as a background trigger type | Early Cycle | N/A | Asynchrony (early cycle detected) | Consider decreasing expiration sensitivity | N/A |
| PA | IE Sync monitoring as a background trigger type | Late Cycle | N/A | Asynchrony (late cycle detected) | Consider increasing expiration sensitivity | OR, consider decreasing support setting if greater than 80% |
| PA | IE Sync monitoring as a background trigger type | Early Cycle | N/A | Asynchrony (early cycle detected) | Consider decreasing expiration sensitivity | N/A |
| VC+ | IE Sync monitoring as a background trigger type | Late Cycle | N/A | Asynchrony (late cycle detected) | Consider decreasing inspiration time | OR, consider switching to a spontaneous breath type |
| VC+ | IE Sync monitoring as a background trigger type | Early Cycle | N/A | Asynchrony (early cycle detected) | Consider increasing inspiration time | OR, consider switching to a spontaneous breath type |

TABLE 1-continued

Recommendation messages based on breath type, secondary conditions, detection method, and/or type of asynchrony detected.

| Breath Type | Detection Method | Type of Asynchrony | Secondary Condition and/or Ventilator Settings | Notification Message | Primary Recommendation Message | Secondary Recommendation Message |
|---|---|---|---|---|---|---|
| VC+ | Monitoring airway pressure (pressure signal derivative) | Inadequate Flow | Low rise time setting | Asynchrony detected (inadequate flow detected) | Consider increasing rise time | N/A |
| VC+ | IE Sync monitoring as a background trigger type | Missed Breath | No Auto PEEP and inspiration time is in normal range based PBW | Asynchrony (missed breaths detected) | Consider increasing trigger sensitivity | OR, consider changing the trigger type |
| VC+ | IE Sync monitoring as a background trigger type | Missed Breath | Tidal Volume too large for PBW | Asynchrony (missed breaths detected) | Consider decreasing tidal volume | N/A |
| VC+ | IE Sync monitoring as a background trigger type, inspiration time monitoring, and respiration rate monitoring | Missed Breath | Auto PEEP, respiration rate, and inspiration time too long for PBW | Asynchrony (missed breaths detected) | Consider decreasing inspiration time | N/A |
| VC+ | IE Sync monitoring as a background trigger type | Missed Breath | Auto PEEP | Asynchrony (missed breaths detected) | Consider increasing PEEP | OR consider decreasing respiration rate if exhalation volume is high or consider decreasing inspiration time |
| VC+ | IE Sync monitoring as a background trigger type and respiration rate monitoring | Double Trigger | Inspiration time is too short for PBW | Asynchrony detected (double trigger detected) | Consider increasing inspiration time | N/A |
| VS | IE Sync monitoring as a background trigger type and Leak compensation monitoring | Late Cycle | Leak present | Asynchrony (late cycle detected) | Consider enabling leak compensation | OR, consider increasing expiration sensitivity |
| VS | IE Sync monitoring as a background trigger type and/or inspiration time as a function of PBW monitoring | Early Cycle | N/A | Asynchrony (early cycle detected) | Consider increasing expiration sensitivity | N/A |
| VS | Monitoring airway pressure (pressure signal derivative) | Inadequate Flow | Low rise time setting | Asynchrony detected (inadequate flow detected) | Consider increasing rise time | N/A |
| VS | IE Sync monitoring as a background trigger type | Missed Breath | Auto PEEP and long inspiration time | Asynchrony (missed breaths detected) | Consider increasing expiration sensitivity | N/A |

TABLE 1-continued

Recommendation messages based on breath type, secondary conditions, detection method, and/or type of asynchrony detected.

| Breath Type | Detection Method | Type of Asynchrony | Secondary Condition and/or Ventilator Settings | Notification Message | Primary Recommendation Message | Secondary Recommendation Message |
|---|---|---|---|---|---|---|
| VS | IE Sync monitoring as a background trigger type | Missed Breath | N/A | Asynchrony (missed breaths detected) | Consider decreasing trigger sensitivity | N/A |
| VS | IE Sync monitoring as a background trigger type | Missed Breath | High tidal volume for PBW | Asynchrony (missed breaths detected) | Consider decreasing the tidal volume setting | N/A |
| VS | IE Sync monitoring as a background trigger type | Double Trigger | High expiration sensitivity | Asynchrony detected (double trigger detected) | Consider decreasing expiration sensitivity | N/A |
| VS | Monitoring inspiration time as a function of PBW, exhalation time, and exhalation tidal volume, | Double Trigger | High expiration sensitivity and short exhalation time | Asynchrony detected (double trigger detected) | Consider decreasing expiration sensitivity | N/A |

Table 1 below lists various examples of primary and secondary recommendations for various breath types based on the listed additional current ventilator settings and/or on the type of asynchrony detected.

As noted above, according to embodiments, the notification message is associated with a primary prompt and the one or more recommendation messages may be associated with a secondary prompt. That is, a primary prompt may provide an alert that asynchrony has been detected and may further provide one or more potential causes for asynchrony. Alternatively, an alert may be separately provided, indicating that asynchrony was detected, and the primary prompt may provide the one or more potential causes for asynchrony. According to additional or alternative embodiments, the secondary prompt provides the one or more recommendations and/or information that may aid the clinician in further addressing and/or mitigating the detected condition. For example, the secondary prompt may recommend addressing asynchrony by adjusting an alternative parameter, by switching the breath type, and/or etc. Smart prompt module 226 may also be configured such that smart prompts (including alerts, primary prompts, and/or secondary prompts) may be displayed in a partially transparent window or format. The transparency may allow for notification and/or recommendation messages to be displayed such that normal ventilator GUI and respiratory data may be visualized behind the messages. This feature may be particularly useful for displaying detailed messages. As described previously, notification and/or recommendation messages may be displayed in areas of the display screen that are either blank or that cause minimal distraction from the respiratory data and other graphical representations provided by the GUI. However, upon selective expansion of a message, respiratory data and graphs may be at least partially obscured. As a result, translucent display may provide the detailed message such that it is partially transparent. Thus, graphical and other data may be visible behind the detailed alarm message.

Additionally, notification and/or recommendation messages may provide immediate access to the display and/or settings screens associated with the detected condition. For example, an associated parameter settings screen may be accessed from a notification and/or a recommendation message via a hyperlink such that the clinician may address the detected condition as necessary. An associated parameter display screen may also be accessed such that the clinician may view clinical data associated with the detected condition in the form of charts, graphs, or otherwise. That is, according to embodiments, the clinician accesses the ventilatory data that implicated the detected condition for verification purposes. For example, when asynchrony has been implicated, depending on the particular ventilatory parameters that implicated asynchrony, the clinician may be able to access ventilatory settings for addressing asynchrony (e.g., a settings screen for adjusting respiration rate, PEEP, $E_{SENS}$, etc.) and/or to view associated ventilatory parameters that implicated asynchrony (e.g., a graphics screen displaying historical flow waveforms, current tidal volume, and/or waveforms illustrating the asynchrony such as a missed breath or late trigger).

According to embodiments, upon viewing the notification and/or recommendation messages, upon addressing the detected condition by adjusting one or more ventilatory settings or otherwise, or upon manual selection, the notification and/or recommendation messages are cleared from the graphical user interface. According to some embodiments, smart prompt module 226 clears the one or more messages from the graphical user interface if a setting is changed on the ventilator, such as a selected breath type. In further embodiments, smart prompt module 226 clears the one or more messages from the graphical user interface if a ventilator setting change was performed by the operator and a threshold was not breached for a predetermined amount of time or number of breaths. In further embodiments, smart prompt module 226 clears the one or more messages from the graphical user interface if the threshold breach does not occur again during a predetermined amount of time or breaths. In some embodiments, the smart prompt module 226 clears the one or more messages from the graphical user interface upon user selection.

Asynchrony Detection During Ventilation of a Patient

Figure 3:
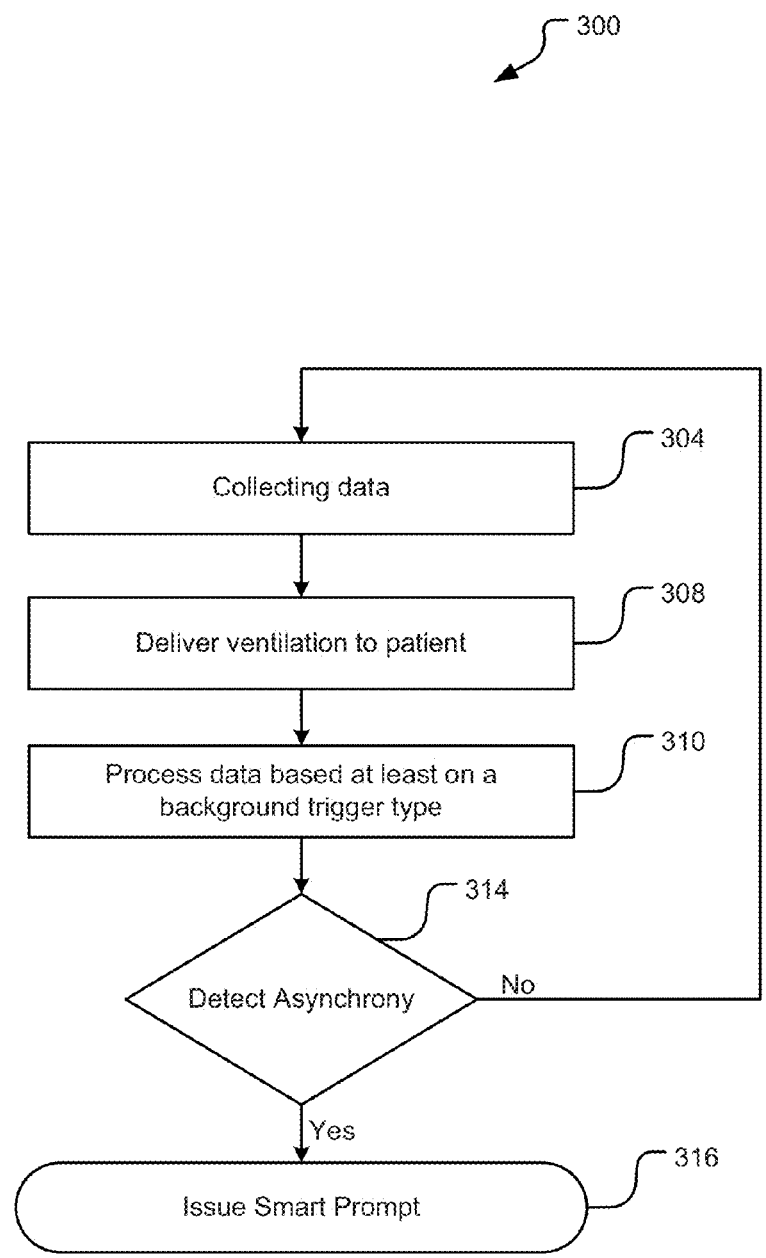
FIG. 3 is a flow chart illustrating an embodiment of a method for detecting an implication of asynchrony.

FIG. 3 is a flow chart illustrating an embodiment of a method 300 for detecting an implication of asynchrony.

As should be appreciated, the particular steps and methods described herein are not exclusive and, as will be understood by those skilled in the art, the particular ordering of steps as described herein is not intended to limit the method, e.g., steps may be performed in differing order, additional steps may be performed, and disclosed steps may be excluded without departing from the spirit of the present methods.

The illustrated embodiment of the method 300 depicts a method for detecting asynchrony during ventilation of a patient. Method 300 begins with collecting data operation 304. Collecting data operation 304 may include receiving data regarding one or more ventilatory settings associated with ventilation of a patient. For example, the ventilator may be configured to provide ventilation to a patient. As such, the ventilatory settings and/or input received may include a prescribed $V_T$, set flow (or peak flow), predicted or ideal body weight (PBW or IBW), $E_{SENS}$, trigger sensitivity, PEEP, etc. Collecting data operation 304 may include receiving data from sensors regarding one or more ventilatory parameters or receiving derived data from a processor. As discussed above, a ventilatory parameter refers to any factor, characteristic, or measurement associated with the ventilation of a patient, whether monitored by the ventilator or by any other device. The collected data may be transmitted by sensors. For example, data regarding flow rate, circuit pressure, flow pattern, inspiratory time setting ($T_I$), etc., may be collected from the sensors, operator interface, and/or processor.

At deliver ventilation operation 308, the ventilator provides ventilation to a patient, as described above. That is, according to embodiments, the ventilator provides ventilation based on the set breath type. For example, during a VC breath type in the mixed mode, the ventilator provides ventilation based on a prescribed $V_T$. In this example, the ventilator may deliver gases to the patient at a set flow at a set RR. When prescribed $V_T$ has been delivered, the ventilator may initiate the expiratory phase unless the ventilator detects a patient trigger or cycle.

While ventilation is being delivered, the ventilator may conduct various data processing operations. For example, at data processing operation 310, the ventilator collects and/or derives various ventilatory parameter data associated with ventilation of the patient based on a background trigger type. For example, as described above, the ventilator may collect data regarding parameters including $T_E$, $V_T$, $T_I$, flow, pressure, etc. Additionally, the ventilator may derive various ventilatory parameter data based on the collected data, e.g., IBW-predicted $T_I$, volume, respiratory resistance, respiratory compliance, detected patient triggers, detected patient cycles, etc. As described previously, measurements for respiratory resistance and/or compliance may be trended continuously for a patient because ventilatory data may be obtained without sedating the patient or otherwise. Additionally, the ventilator may generate various graphical representations of the collected and/or derived ventilatory parameter data, e.g., flow waveforms, pressure waveforms, pressure-volume loops, flow-volume loops, etc.

According to some embodiments, at detect asynchrony operation 314 the ventilator determines whether asynchrony is implicated by evaluating s expiratory time, airway pressure, airway flow, delivered tidal volume, detected patient triggers, detected patient cycles, etc. and comparing the evaluated parameters to one or more predetermined thresholds. In some embodiments, in order to prevent unnecessary alarms, notifications, and/or recommendations, thresholds and conditions are utilized by the detect asynchrony operation 314 to determine when asynchrony has occurred with sufficient frequency to warrant notification of the operator. For example, in some embodiments, asynchrony that occurs in one breath in isolation from any other breath with asynchrony will not be considered enough to warrant an occurrence of asynchrony by detect asynchrony operation 314.

In some embodiments, at detect asynchrony operation 314 the ventilator may determine whether asynchrony is implicated based on a predetermined frequency of occurrence. For example, in one embodiment, the ventilator at detect asynchrony operation 314 determines that asynchrony is implicated when the number of detected inspiration patient efforts by the background trigger type does not equal the number of delivered breaths by the active trigger type, when a detected patient effort (inspiration or expiration) is more than 60 ms away from the corresponding delivered inspiration or expiration by the active trigger type, the pressure-time curve rises at a rate of at least 10 ml/m at the predetermined frequency, detecting an increase in Edi exceeding a predetermined threshold at a predetermined frequency, when a derivative of the pressure-time curve changes from a positive slope to a negative slope at a predetermined frequency, when a change in a derivative of $P_m$ exceeds a predetermined threshold at the predetermined frequency, when inspiration time is too long based on a patient PBW, and/or when tidal volume is too high based on the patient PBW. For example, in another embodiment, the ventilator at detect asynchrony operation 314 determines that asynchrony is implicated when one or more of the following conditions are met:

1. expiratory time for a patient-initiated mandatory breath is less than 240 milliseconds (ms);
2. the exhaled tidal volume associated with the expiratory period is less than 10% of the delivered tidal volume of the prior inspiratory period;
3. no disconnect alarm is detected.

For example, in an additional embodiment, the ventilator at detect asynchrony operation 314 determines that asynchrony is implicated when one or more of the following conditions are met for PIM breath:

1. the amount of pressure delivered when a predetermined amount of tidal volume has been delivered or a predetermined proportion of an inspiration time has expired in the PIM breath is less than the set PEEP; and
2. the amount of mean airway pressure for the PIM breath is less than the set PEEP.

Upon detecting one or more of the above conditions, the ventilator may also ensure that at least one of the following two conditions is met:

3. expiratory time for a PIM breath is greater than a predetermined amount of time;
4. the ventilation tubing system status is connected; and
5. no disconnect alarm is detected.

If asynchrony is implicated, detect asynchrony operation 314 may proceed to issue smart prompt operation 316. If asynchrony is not implicated, the detect asynchrony operation 314 may return to collecting data operation 304. However, in some embodiments, the ventilator continuously performs the collecting data operation 304, the deliver ventilation operation 308, data processing operation 310, and detect asynchrony operation 314.

The thresholds listed above are just one example list of possible conditions that could be used to indicate asynchrony in the detect asynchrony operation 314. Any suitable list of conditions for determining the occurrence of asynchrony may be utilized by the detect asynchrony operation 314. As may be appreciated, the ventilator may determine whether asynchrony is implicated at detect asynchrony operation 314 via any suitable means. Indeed, any of the above described ventilatory parameters may be evaluated according to various thresholds for detecting asynchrony. Further, the disclosure regarding specific ventilatory parameters as they may implicate asynchrony is not intended to be limiting. In fact, any suitable ventilatory parameter may be monitored and evaluated for detecting asynchrony within the spirit of the present disclosure. As such, if asynchrony is implicated via any suitable means, the detect asynchrony operation 314 may proceed to issue smart prompt operation 316.

At issue smart prompt operation 316, the ventilator may alert the clinician via any suitable means that asynchrony has been implicated. For example, according to embodiments, the ventilator may display a smart prompt including a notification message and/or a recommendation message regarding the detection and/or cause of asynchrony on the GUI. According to alternative embodiments, the ventilator may communicate the smart prompt, including the notification message and/or the recommendation message, to a remote monitoring system communicatively coupled to the ventilator. According to alternative embodiments, the issued smart prompt is any visual and/or audio notification.

According to embodiments, the notification message may alert the clinician that asynchrony has been detected and, optionally, may provide information regarding the type of asynchrony and/or any ventilatory parameter(s) that implicated asynchrony. According to additional embodiments, the recommendation message may provide one or more suggestions for mitigating asynchrony. According to further embodiments, the one or more suggestions may be based on the patient's particular ventilatory settings (e.g. breath type, flow pattern, flow rate, etc.) and/or diagnosis. According to some embodiments, the clinician may access one or more parameter settings and/or display screens from the smart prompt via a hyperlink or otherwise for addressing asynchrony. According to additional or alternative embodiments, a clinician may remotely access one or more parameter and/or display screens from the smart prompt via a hyperlink or otherwise for remotely addressing asynchrony.

Smart Prompt Generation Regarding Asynchrony Detection

Figure 4:
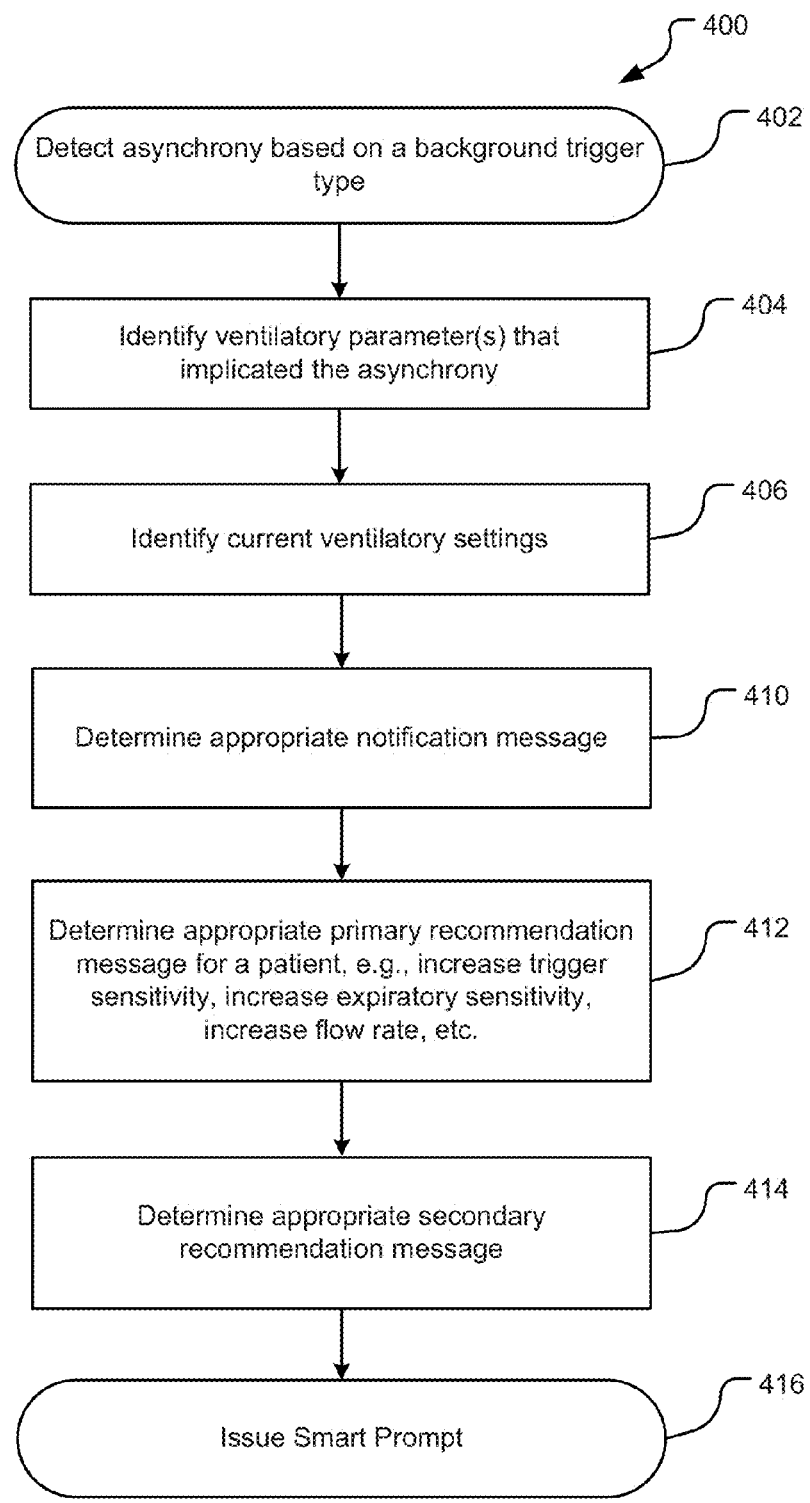
FIG. 4 is a flow chart illustrating an embodiment of a method for issuing a smart prompt upon detecting an implication of asynchrony.

FIG. 4 is a flow chart illustrating an embodiment of a method 400 for issuing a smart prompt upon detecting an implication of asynchrony.

As should be appreciated, the particular steps and methods described herein are not exclusive and, as will be understood by those skilled in the art, the particular ordering of steps as described herein is not intended to limit the method, e.g., steps may be performed in differing order, additional steps may be performed, and disclosed steps may be excluded without departing from the spirit of the present methods.

The illustrated embodiment of the method 400 depicts a method for issuing a smart prompt upon detecting asynchrony during ventilation of a patient. Method 400 begins with detect operation 402, wherein the ventilator detects that asynchrony is implicated based on a background trigger type, as described above in method 300.

At identify ventilatory parameters operation 404, the ventilator may identify one or more ventilatory parameters that implicated asynchrony. In some embodiments, in order to prevent unnecessary alarms, notifications, and/or recommendations, thresholds and conditions are utilized by identify ventilatory parameters operation 404 to determine when asynchrony has occurred with sufficient frequency to warrant notification of the operator. For example, in some embodiments, asynchrony that occurs in a breath in isolation from any other breath with asynchrony will not be considered enough to warrant an occurrence of asynchrony by identify ventilatory parameters operation 404.

For example, the ventilator may recognize that asynchrony was implicated when the number of detected inspiration patient efforts by the background trigger type does not equal the number of delivered breaths by the active trigger type, when a detected patient effort (inspiration or expiration) is more than 60 ms away from the corresponding delivered inspiration or expiration by the active trigger type, the pressure-time curve rises at a rate of at least 10 ml/m at the predetermined frequency, detecting an increase in Edi exceeding a predetermined threshold at a predetermined frequency, when a derivative of the pressure-time curve changes from a positive slope to a negative slope at a predetermined frequency, when a change in a derivative of $P_m$ exceeds a predetermined threshold at the predetermined frequency, when inspiration time is too long based on a patient PBW, and/or when tidal volume is too high based on the patient PBW. For example, in another embodiment, the ventilator at detect asynchrony operation 314 determines that asynchrony is implicated when one or more of the following conditions are met:
1. expiratory time for a patient-initiated mandatory breath is less than 240 milliseconds (ms);
2. the exhaled tidal volume associated with the expiratory period is less than 10% of the delivered tidal volume of the prior inspiratory period;
3. no disconnect alarm is detected.

For example, in an additional embodiment, the ventilator at detect asynchrony operation 314 determines that asynchrony is implicated when one or more of the following conditions are met for PIM breath:
1. the amount of pressure delivered when a predetermined amount of tidal volume has been delivered or a predetermined proportion of an inspiration time has expired in the PIM breath is less than the set PEEP; and
2. the amount of mean airway pressure for the PIM breath is less than the set PEEP.

Upon detecting one or more of the above conditions, the ventilator may also ensure that at least one of the following two conditions is met:
3. expiratory time for a PIM breath is greater than a predetermined amount of time;
4. the ventilation tubing system status is connected; and
5. no disconnect alarm is detected.

The thresholds listed above are just one example list of possible conditions that could be used to indicate asynchrony in the parameters operation 404. Any suitable list of conditions for determining the occurrence of asynchrony may be utilized by the parameters operation 404. As may be appreciated, the ventilator may use information regarding ventilatory parameters that implicated asynchrony in determining an appropriate notification and/or recommendation message of the smart prompt. Based on the parameters that implicated the asynchrony, the ventilator during the parameters operation 404 may further identify the type of asynchrony detected, such as missed breaths, late cycling, early cycling, inadequate flow, mismatch flow, and etc.

At identify settings operation 406, the ventilator may identify one or more current ventilatory settings associated with the ventilatory treatment of the patient. For example, current ventilatory settings may have been received upon initiating ventilation for the patient and may have been determined by the clinician or otherwise (e.g., breath type, oxygenation, PBW or IBW, disease conditions, etc.). For instance, current ventilatory settings associated with ventilation for a patient may include, $V_T$, $T_I$, flow, $E_{SENS}$, flow pattern, IBW-predicted based on $T_I$, etc. As may be appreciated, the ventilator may use information regarding current ventilatory settings in determining an appropriate notification and/or recommendation message of the smart prompt.

At determine operation 410, the ventilator may determine an appropriate notification message. For example, the appropriate notification message may alert the clinician that asynchrony has been implicated and, optionally, may provide information regarding the type of asynchrony and the ventilatory parameter(s) that implicated asynchrony. For example, the appropriate notification may alert the clinician that asynchrony was the result of a missed breath as detected based on the monitoring of patient effort by the IE Sync background trigger type. In another example, the appropriate notification may alert the clinician that asynchrony was the result of a late trigger during ventilation with Auto PEEP. In another example, the appropriate notification may alert the clinician that asynchrony was implicated because a mean airway pressure delivered is less than a set PEEP in more than 10% of the PIM breaths as detected by an IE Sync background trigger type. For example, if asynchrony was detected because of a missed breath, the ventilator may offer one or more notification messages that may include: "Consider increasing trigger sensitivity" or "consider increasing $E_{SENS}$." In alternative embodiments, measured parameters such as mean airway pressure, detected patient efforts, and airway flow may be utilized as the notification message.

At determine operation 412, the ventilator may determine an appropriate primary recommendation message. The appropriate primary recommendation message may provide one or more specific suggestions for mitigating asynchrony. According to some embodiments, in determining the appropriate primary recommendation message, the ventilator may take into consideration the one or more monitored ventilatory parameters that implicated asynchrony and the type of asynchrony detected.

According to other embodiments, in determining an appropriate primary recommendation message the ventilator may take into consideration one or more of the patient's ventilatory settings. For example, if the breath type is volume-control (VC), if the flow pattern is set to square, and if inadequate flow is the type of asynchrony detected, the ventilator may offer one or more recommendation messages that may include: "Consider increasing the flow" or "Consider changing to a pressure targeted breath type." In another example, if the breath type is proportional assist (PA), and if the type of asynchrony detected is a late cycle, the ventilator may offer one or more recommendation messages that may include: "Consider increasing expiratory sensitivity." In another example, if the breath type is pressure control (PC), if the tidal volume too large based on the patient PBW, and if the type of asynchrony detected is a missed breath, the ventilator may offer one or more recommendation messages that may include: "Consider decreasing inspiration pressure." Any of the primary recommendations as discussed above and as displayed in Table 1 above for any breath type may be utilized by method 400.

In some embodiments, at determine operation 414, the ventilator also determines an appropriate secondary recommendation message. The secondary recommendation message may provide one or more general suggestions for mitigating asynchrony. For example, the secondary recommendation message may include: "Consider changing to a spontaneous breath type, Consider changing to a pressure-based breath type; Consider changing trigger type, Consider decreasing respiration rate if the tidal volume is high" The secondary recommendation message may provide additional recommendations for mitigating asynchrony. In further embodiments, the appropriate secondary recommendation message may take into consideration the patient's current ventilatory settings. That is, during a VC breath type, the ventilator may suggest changing to a spontaneous breath type such as PA, PS, IE Synch, DEA, or VS. As known by a person of skill in the art any notification, message, and/or recommendation disclosed herein may suitable for use as a primary and/or secondary recommendation message.

At issue smart prompt operation 416, a smart prompt is issued. A smart prompt is issued when the ventilator alerts the clinician via any suitable means that asynchrony has been implicated. For example, according to embodiments, a smart prompt may include an appropriate notification message and an appropriate recommendation message regarding the presence of asynchrony. Additionally or alternatively, the smart prompt may include an appropriate notification message, an appropriate primary recommendation message, and an appropriate secondary recommendation message. The smart prompt may be displayed via any suitable means, e.g., on the ventilator GUI and/or at a remote monitoring station, such that the clinician is alerted as to the potential presence of asynchrony and offered additional information and/or recommendations for mitigating asynchrony, as described herein.

In some embodiments, a ventilatory system for issuing a smart prompt when asynchrony is implicated during ventilation of a patient is disclosed. The ventilatory system includes: means for collecting data associated with ventilatory parameters; means for processing the collected ventilatory parameter data based on a background trigger type, wherein the step of processing the collected ventilatory parameter data comprises deriving ventilatory parameter data from the collected ventilatory parameter data; means for determining that asynchrony is implicated upon detecting that the processed ventilatory parameter data breaches a received at least one predetermined threshold; and means for issuing a smart prompt when asynchrony is implicated.

In some embodiments, a ventilatory system for issuing a smart prompt when asynchrony is implicated during ventilation of a patient is disclosed. The ventilatory system includes: means for detecting asynchrony based on a background trigger type, means for identifying one or more ventilator parameters that implicated the asynchrony; means for identifying the current ventilator settings, means for determining the appropriate notification message, means for determining the appropriate primary recommendation message for the patient, means for determining the appropriate secondary recommendation for the patient, and means for issuing a smart prompt.

In further embodiments, the means for the medical ventilator are illustrated in FIGS. 1 and 2 and are described in the above descriptions of FIGS. 1 and 2. However, the means described above for FIGS. 1 and 2 and illustrated in FIGS. 1 and 2 are but one example only and are not meant to be limiting.

Ventilator GUI Display of Initial Smart Prompt

Figure 5:
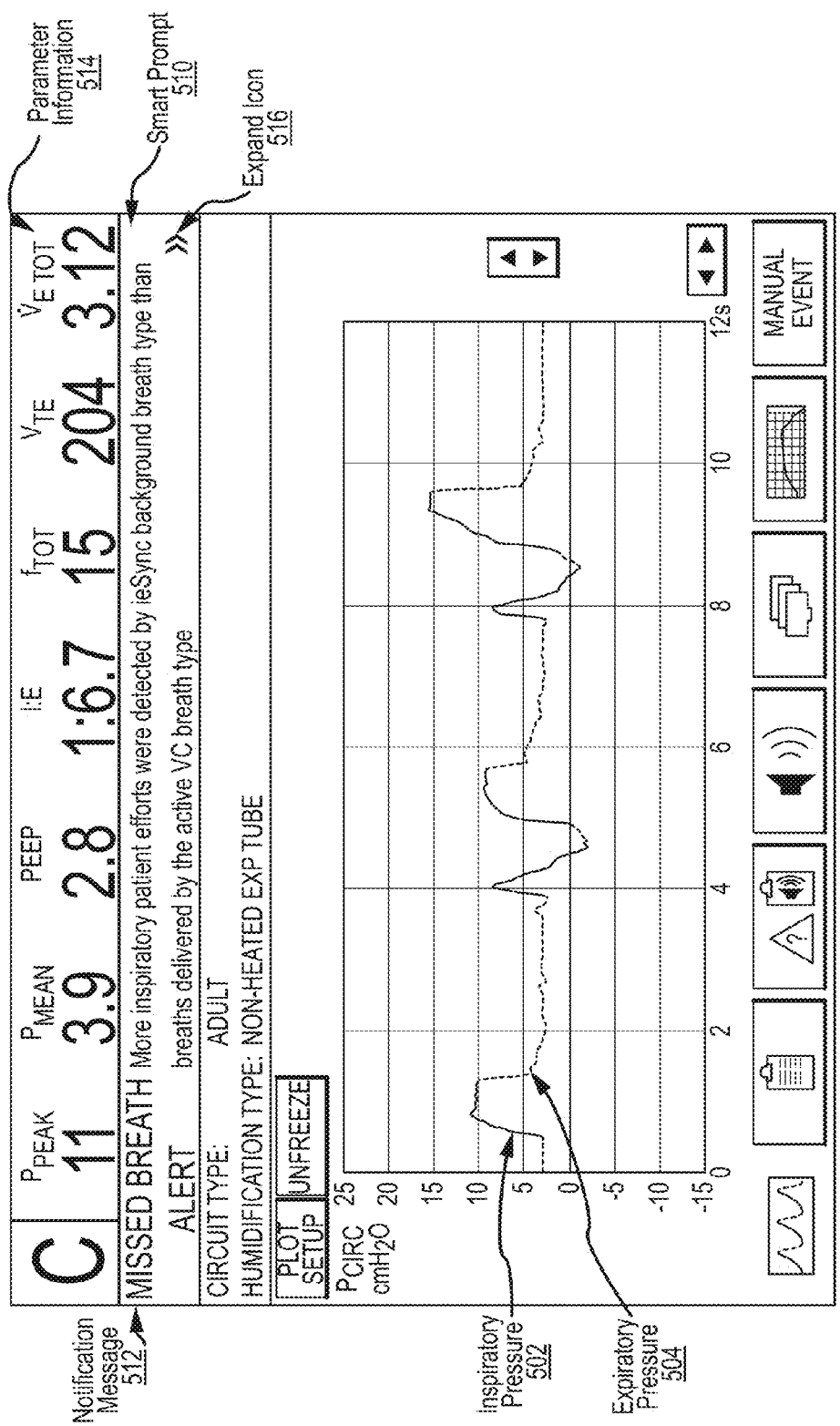
FIG. 5 is an illustration of an embodiment of a graphical user interface displaying a smart prompt having a notification message.

FIG. 5 is an illustration of an embodiment of a graphical user interface 500 displaying a smart prompt having a notification message 512.

Graphical user interface 500 may display various monitored and/or derived data to the clinician during ventilation of a patient. In addition, graphical user interface 500 may display various messages to the clinician (e.g., alarm messages, etc.). Specifically, graphical user interface 500 may display a smart prompt as described herein.

According to embodiments, the ventilator may monitor and evaluate various ventilatory parameters based on one or more predetermined thresholds to detect asynchrony. As illustrated, a pressure waveform may be generated and displayed by the ventilator on graphical user interface 500. As further illustrated, the pressure waveform may be displayed such that pressure during inspiration 502 is represented in a different color (e.g., green) than pressure during expiration 504 (e.g., yellow). In one embodiment, as illustrated, asynchrony 506 occurs when an IE Sync background trigger type detects more inspiration efforts than breaths delivered by the VC breath type. Asynchrony results, in this case, when the patient desires more breaths than are being delivered by the ventilator to the patient.

Upon a determination that asynchrony is implicated, the graphical user interface 500 may display a smart prompt, e.g., smart prompt 510.

According to embodiments, smart prompt 510 may be displayed in any suitable location such that a clinician may be alerted regarding a detected patient condition, but while allowing other ventilatory displays and data to be visualized substantially simultaneously. As illustrated, smart prompt 510 is presented as a bar or banner across an upper region of the graphical user interface 500. However, as previously noted, smart prompt 510 may be displayed as a tab, icon, button, banner, bar, or any other suitable shape or form. Further, smart prompt 510 may be displayed in any suitable location within the graphical user interface 500. For example, smart prompt 510 may be located along any border region of the graphical user interface 500 (e.g., top, bottom, or side borders) (not shown), across an upper region (shown), or in any other suitable location. Further, as described herein, smart prompt 510 may be partially transparent (not shown) such that ventilatory displays and data may be at least partially visible behind smart prompt 510.

Specifically, smart prompt 510 may alert the clinician that asynchrony has been detected, for example by notification message 512. As described herein, notification message 512 may alert the clinician that asynchrony is implicated via any suitable means, e.g., "Missed Breath Alert" (shown), "Asynchrony Alert" (not shown), "Asynchrony Detected" (not shown), "Asynchrony Implicated" (not shown), "Late Cycle Alert" (not shown), "Early Cycle Detected" (not shown), "Late Trigger Implicated" (not shown), "False trigger Alert" (not shown), "Inadequate Flow Detected" (not shown), "Mismatched Breath Implicated" (not shown), "Long Inspiration Alert" (not shown), "Double Trigger Detected" (not shown), "Long Tidal Volume Implicated" (not shown), or etc. Smart prompt 510 may further include information regarding ventilatory parameters that implicated asynchrony. For example, if asynchrony was detected based on more inspiration efforts being detected by the background trigger type than breaths delivered by the active trigger type, then this information may be displayed by the notification message 512 (e.g., "More inspiration patient efforts were detected by the IE Sync background trigger type than breath delivered by the active VC breath type," shown). According to the illustrated embodiment, parameter information 514 is provided along with the notification message 512 in a banner. According to alternative embodiments, in addition to the notification message 512 and the parameter information 514, one or more recommendation messages may be provided in an initial smart prompt banner (not shown). According to other embodiments, rather than providing information regarding ventilatory parameters that implicated asynchrony in the initial smart prompt, this information may be provided within an expanded portion (not shown) of smart prompt 510.

According to embodiments, smart prompt 510 may be expanded to provide additional information and/or recommendations to the clinician regarding a detected patient condition. For example, an expand icon 516 may be provided within a suitable area of the smart prompt 510. According to embodiments, upon selection of the expand icon 516 via any suitable means, the clinician may optionally expand the smart prompt 510 to acquire additional information and/or recommendations for mitigating the detected patient condition. According to further embodiments, smart prompt 510 may include links (not shown) to additional settings and/or display screens of the graphical user interface 500 such that the clinician may easily and quickly mitigate and/or verify the detected condition.

As may be appreciated, the disclosed data, graphics, and smart prompt illustrated in graphical user interface 500 may be arranged in any suitable order or configuration such that information and alerts may be communicated to the clinician in an efficient and orderly manner. The disclosed data, graphics, and smart prompt are not to be understood as an exclusive array, as any number of similar suitable elements may be displayed for the clinician within the spirit of the present disclosure. Further, the disclosed data, graphics, and smart prompt are not to be understood as a necessary array, as any number of the disclosed elements may be appropriately replaced by other suitable elements without departing from the spirit of the present disclosure. The illustrated embodiment of the graphical user interface 500 is provided as an example only, including potentially useful information and alerts that may be provided to the clinician to facilitate communication of detected set asynchrony in an orderly and informative way, as described herein.

Ventilator GUI Display of Expanded Smart Prompt

Figure 6:
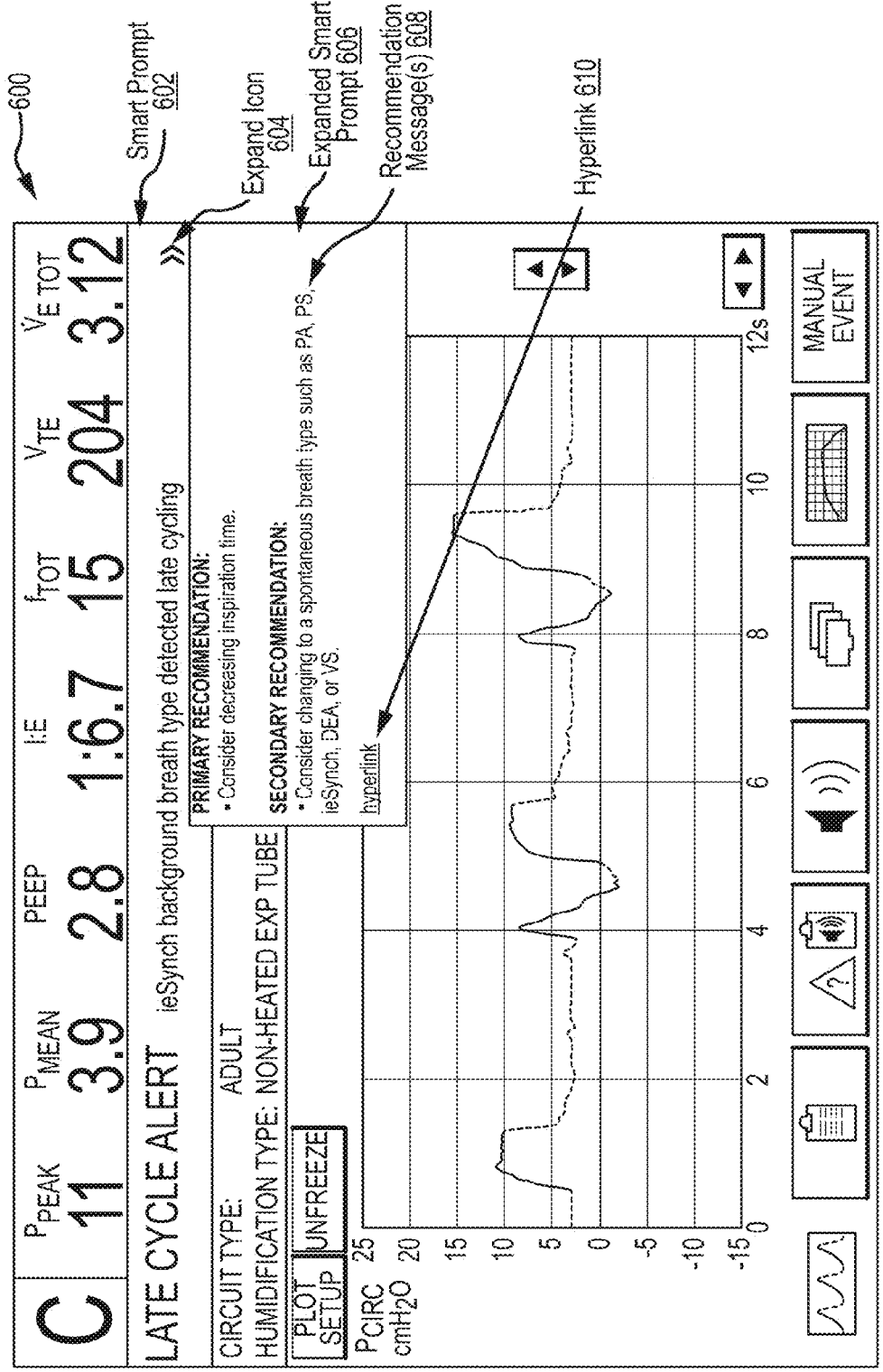
FIG. 6 is an illustration of an embodiment of a graphical user interface displaying an expanded smart prompt having a notification message and one or more recommendation messages.

FIG. 6 is an illustration of an embodiment of a graphical user interface 600 displaying an expanded smart prompt 606 having a notification message and one or more recommendation messages 608.

Graphical user interface 600 may display various monitored and/or derived data to the clinician during ventilation of a patient. In addition, graphical user interface 600 may display an expanded smart prompt 606 including one or more recommendation messages 608 as described herein.

According to embodiments, as described above, an expand icon 604 may be provided within a suitable area of smart prompt 602. Upon selection of the expand icon 604, the clinician may optionally expand smart prompt 602 to acquire additional information and/or recommendations for mitigating the detected patient condition. For example, expanded smart prompt 606 may be provided upon selection of expand icon 604. As described above for smart prompt 510, expanded smart prompt 606 may be displayed as a tab, icon, button, banner, bar, or any other suitable shape or form. Further, expanded smart prompt 606 may be displayed in any suitable location within the graphical user interface 600. For example, expanded smart prompt 606 may be displayed below (shown) smart prompt 602, to a side (not shown) of smart prompt 602, or otherwise logically associated with smart prompt 602. According to other embodiments, an initial smart prompt may be hidden (not shown) upon displaying expanded smart prompt 606. Expanded smart prompt 606 may also be partially transparent (not shown) such that ventilatory displays and data may be at least partially visible behind expanded smart prompt 606.

According to embodiments, expanded smart prompt 606 may comprise additional information (not shown) and/or one or more recommendation messages 608 regarding detected asynchrony. For example, the one or more recommendation messages 608 may include a primary recommendation message and a secondary recommendation message. The primary recommendation message may provide one or more specific suggestions for mitigating asynchrony. For example, if asynchrony was implicated during pressure-control ventilation and if the type of asynchrony detected is a late cycle, then the ventilator may offer one or more primary recommendation messages 608 that may include: "Consider decreasing inspiration time." The secondary recommendation message may provide one or more general suggestions for mitigating asynchrony. For example, the secondary recommendation message may include: "Consider changing to spontaneous breath type such as PA, PS, IE Sync, DEA, or VS."

According to embodiments, expanded smart prompt 606 may also include one or more hyperlinks 610, which may provide immediate access to the display and/or settings screens associated with detected asynchrony. For example, associated parameter settings screens may be accessed from expanded smart prompt 606 via hyperlinks 610 such that the clinician may address detected asynchrony by adjusting one or more parameter settings as necessary. Alternatively, associated parameter display screens may be accessed such that the clinician may view clinical data associated with asynchrony in the form of charts, graphs, or otherwise. That is, according to embodiments, the clinician may access the ventilatory data that implicated asynchrony for verification purposes. For example, when asynchrony has been implicated, depending on the particular ventilatory parameters that implicated asynchrony, the clinician may be able to access associated parameter settings screens for addressing asynchrony (e.g., settings screens for adjusting flow pattern, peak flow rate, breath type, etc.). Additionally or alternatively, the clinician may be able to access and/or view display screens associated with the ventilatory parameters that implicated asynchrony (e.g., a graphics screen displaying historical flow waveforms, volume waveforms, and/or pressure waveforms that give rise to implications of asynchrony).

As may be appreciated, the disclosed smart prompt and recommendation messages 608 illustrated in graphical user interface 600 may be arranged in any suitable order or configuration such that information and alerts may be communicated to the clinician in an efficient and orderly manner. Indeed, the illustrated embodiment of the graphical user interface 600 is provided as an example only, including potentially useful information and recommendations that may be provided to the clinician to facilitate communication of suggestions for mitigating detected asynchrony in an orderly and informative way, as described herein.

Unless otherwise indicated, all numbers expressing measurements, dimensions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. Further, unless otherwise stated, the term "about" shall expressly include "exactly," consistent with the discussions regarding ranges and numerical data. Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 4 percent to about 7 percent" should be interpreted to include not only the explicitly recited values of about 4 percent to about 7 percent, but also include individual values and sub-ranges within the indicated range. Thus, included in this numerical range are individual values such as 4.5, 5.25 and 6 and sub-ranges such as from 4-5, from 5-7, and from 5.5-6.5, etc. This same principle applies to ranges reciting only one numerical value. Furthermore, such an interpretation should apply regardless of the breadth of the range or the characteristics being described.

It will be clear that the systems and methods described herein are well adapted to attain the ends and advantages mentioned as well as those inherent therein. Those skilled in the art will recognize that the methods and systems within this specification may be implemented in many manners and as such is not to be limited by the foregoing exemplified embodiments and examples. In other words, functional elements being performed by a single or multiple components, in various combinations of hardware and software, and individual functions can be distributed among software applications at either the client or server level. In this regard, any number of the features of the different embodiments described herein may be combined into one single embodiment and alternative embodiments having fewer than or more than all of the features herein described are possible.

While various embodiments have been described for purposes of this disclosure, various changes and modifications may be made which are well within the scope of the present disclosure. Numerous other changes may be made which will readily suggest themselves to those skilled in the art and which are encompassed in the spirit of the disclosure and as defined in the appended claims.

What is claimed is:

1. A ventilator-implemented method for detecting asynchrony during ventilation of a patient, the method comprising:
    collecting data associated with ventilatory parameters;
    processing the collected ventilatory parameter data, wherein the step of processing the collected ventilatory parameter data comprises deriving ventilatory parameter data from the collected ventilatory parameter data based at least on a background trigger type;
    determining that an asynchrony is implicated upon detecting that the processed ventilatory parameter data breaches a received at least one predetermined threshold; and
    issuing a smart prompt when the asynchrony is implicated.

2. The method of claim 1, wherein the step of determining asynchrony further requires determining that the processed ventilatory parameter data breaches the received at least one predetermined threshold at a predetermined frequency.

3. The method of claim 1, wherein the processed ventilatory parameter data comprises:
    at least one of airway flow, airway pressure, and neural respiratory output, and wherein the processed ventilatory parameter data comprises:
    at least one of a detected inspiratory trigger and a detected expiratory trigger.

4. The method of claim 1, wherein the background trigger type is an IE Sync trigger type.

5. The method of claim 1, wherein the step of determining that asynchrony is implicated comprises:

receiving the predetermined threshold, the predetermined threshold comprising:
a number of first patient efforts detected by the background trigger type must be equal to a number of second patient efforts detected by an active trigger type in a predetermined amount of time;
determining the number of first patient efforts detected by the background trigger type and determining the number of second patient efforts detected by the active trigger type in the predetermined amount of time; and
determining that the number of first patient efforts detected by the background trigger type is not equal to the number of second patient efforts detected by the active trigger type in the predetermined amount of time.

6. The method of claim 1, wherein the step of determining that asynchrony is implicated comprises:
receiving the predetermined threshold, the predetermined threshold comprising:
a first patient effort detected by the background breath type must occur within 60 milliseconds of a second patient effort detected by an active breath type;
determining when a first patient effort is detected by the background breath type and determining when the second patient effort is detected by the active breath type;
determining that the first patient effort detected by the background breath type is more than 60 milliseconds from the second patient effort detected by the active breath type.

7. The method of claim 1, wherein the step of determining that asynchrony is implicated comprises:
receiving the predetermined threshold, the predetermined threshold comprising:
a first inspiratory patient effort and an expiratory patient effort is detected by the background trigger type before of a second inspiratory patient effort is detected by an active trigger type;
determining when a first inspiratory patient effort and the expiratory patient effort is detected by the background trigger type and determining when the inspiratory second patient effort is detected by the active trigger type;
determining that the first inspiratory patient effort and the expiratory patient effort are detected by the background trigger type before the second patient effort is detected by the active trigger type.

8. The method of claim 7, further comprising:
determining an appropriate recommendation message for the issued smart prompt based at least in part on detecting that the processed ventilatory parameter data breaches the received at least one predetermined threshold.

9. The method of claim 7, further comprising:
identifying one or more ventilatory settings associated with a ventilatory treatment of the patient,
wherein the appropriate recommendation message includes a change to the one or more ventilatory settings, and
wherein the one or more ventilatory settings include at least one of a breath type, an inspiration time, an exhalation time, an inspiratory sensitivity, an expiratory sensitivity, a flow rate, a rise time, a flow pattern, a tidal volume, and an inspiratory pressure.

10. A ventilatory system for issuing a smart prompt when asynchrony is implicated during ventilation of a patient, comprising:
at least one processor; and
at least one memory, communicatively coupled to the at least one processor and containing instructions that, when executed by the at least one processor issue a smart prompt when asynchrony is implicated, the instructions comprising:
detect that asynchrony is implicated for a patient based on a background trigger type;
determine an appropriate notification message;
determine an appropriate recommendation message; and
issue at least one of the appropriate notification message and the appropriate recommendation message.

11. The ventilatory system of claim 10, the instructions further comprising:
determine processed ventilatory parameter data that implicated asynchrony, and
wherein the determine the appropriate notification message is based at least in part on the processed ventilatory parameter data that implicated asynchrony.

12. The ventilatory system of claim 10, wherein the appropriate notification message comprises an alert that asynchrony is implicated and information regarding the processed ventilatory parameter data that implicated asynchrony.

13. The ventilatory system of claim 10, wherein the appropriate recommendation message comprises a primary recommendation message and a secondary recommendation message.

14. The method of claim 10, the instructions further comprising:
determine one or more ventilatory settings associated with a ventilatory treatment of the patient; and
wherein the determine the appropriate recommendation message is based at least in part on evaluating the one or more ventilatory settings.

15. The method of claim 14, wherein the one or more ventilatory settings is a breath type.

16. The ventilatory system of claim 15, wherein the appropriate recommendation message comprises a primary recommendation message and a secondary recommendation message based at least in part on the breath type.

17. The ventilatory system of claim 16, wherein the primary recommendation message comprises one of:
a recommendation to change to a square flow pattern;
a recommendation to switch to a pressure-targeted breath type;
a recommendation to increase flow rate;
a recommendation to increase trigger sensitivity;
a recommendation to change trigger type;
a recommendation to increase expiratory sensitivity;
a recommendation to increase set PEEP;
a recommendation to lower set respiration rate;
a recommendation to decrease trigger sensitivity;
a recommendation to enable leak compensation;
a recommendation to increase inspiration time;
a recommendation to decrease inspiration time;
a recommendation to decrease the support setting;
a recommendation to increase tidal volume;
a recommendation to decrease tidal volume;
a recommendation to increase inspiration pressure;
a recommendation to increase rise time; and
a recommendation to decrease flow rate.

18. The ventilatory system of claim 16, wherein the secondary recommendation message comprises:
a recommendation to change to an IE Sync breath trigger type;
a recommendation to change to a DEA trigger type;
a recommendation to change to an IE Sync breath type;

a recommendation to change to a DEA breath type;
a recommendation to decrease tidal volume;
a recommendation to increase expiration sensitivity;
a recommendation to decrease inspiration time;
a recommendation to decrease a support setting if greater than 80%;
a recommendation to decrease respiration rate;
a recommendation to decrease respiration rate if exhalation volume is high;
a recommendation to change to a spontaneous breath type;
a recommendation to change to a flow pattern to square;
a recommendation to change to a pressure targeted breath type; and
a recommendation to change trigger type.

19. The ventilatory system of claim 10, wherein the determine the appropriate recommendation message comprises: determining if a secondary condition is implicated; and
wherein the determine the appropriate notification message comprises: identifying the type of asynchrony detected, wherein the type of asynchrony is selected from a group including: missed breath, early cycle, flow mismatch, late cycle, false trigger, inadequate flow, late trigger, high tidal volume, double trigger, and long inspiratory time.

20. A graphical user interface for displaying one or more prompts corresponding to a detected condition, a ventilator configured with a computer having a user interface including the graphical user interface for accepting commands and for displaying information, the graphical user interface comprising:
at least one window; and
one or more elements within the at least one window comprising at least one prompt element for communicating information regarding a detected condition based on a background trigger type, wherein the detected condition is asynchrony during ventilation of a patient,
wherein the at least one prompt element further comprises at least one of a notification message and one or more recommendation messages, wherein the notification message comprises one or more alerts associated with a detected implication and cause of asynchrony, and wherein the one or more recommendation messages comprise one or more recommendations for mitigating asynchrony,
wherein the one or more recommendations during a volume-control (VC) breath type comprise one or more of:
consider changing to a square pattern;
consider switching to a pressure-targeted breath type;
consider increasing flow rate;
consider increasing trigger sensitivity;
consider changing trigger type;
consider increasing expiratory sensitivity;
consider increasing set PEEP;
consider lowering set respiration rate;
consider decreasing trigger sensitivity;
consider enabling leak compensation;
consider increasing tidal volume; and
consider decreasing flow rate.

* * * * *